US007303898B2

(12) United States Patent
Hurtado et al.

(10) Patent No.: US 7,303,898 B2
(45) Date of Patent: Dec. 4, 2007

(54) DEFECTIVE SINDBIS VIRAL VECTORS

(75) Inventors: Alicia Hurtado, New York, NY (US); Daniel Meruelo, Scarborough, NY (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 11/392,926

(22) Filed: Mar. 28, 2006

(65) Prior Publication Data

US 2007/0020236 A1 Jan. 25, 2007

Related U.S. Application Data

(60) Provisional application No. 60/755,428, filed on Dec. 30, 2005, provisional application No. 60/666,432, filed on Mar. 29, 2005.

(51) Int. Cl.

| | |
|---|---|
| ***C12N 15/64*** | (2006.01) |
| ***C12N 15/00*** | (2006.01) |
| ***C07H 21/02*** | (2006.01) |
| ***C07H 21/04*** | (2006.01) |

(52) U.S. Cl. .................. 435/91.4; 435/320.1; 536/23.1

(58) Field of Classification Search ............... 435/91.4, 435/320.1; 536/23.1

See application file for complete search history.

(56) References Cited

U.S. PATENT DOCUMENTS

| | | | |
|---|---|---|---|
| 5,091,309 | A | 2/1992 | Schlesinger et al. |
| 5,217,879 | A | 6/1993 | Huang et al. |
| 5,739,026 | A | 4/1998 | Garoff |
| 5,789,245 | A | 8/1998 | Dubensky, Jr. et al. |
| 5,814,482 | A | 9/1998 | Dubensky, Jr. et al. |
| 5,843,723 | A | 12/1998 | Dubensky, Jr. et al. |
| 6,015,686 | A | 1/2000 | Dubensky, Jr. et al. |
| 6,015,694 | A | 1/2000 | Dubensky, Jr. et al. |
| 6,190,666 | B1 | 2/2001 | Garoff et al. |
| 6,224,879 | B1 | 5/2001 | Sjoberg |
| 6,242,259 | B1 | 6/2001 | Polo et al. |
| 6,329,201 | B1 | 12/2001 | Polo et al. |
| 6,342,372 | B1 | 1/2002 | Dubensky, Jr. et al. |
| 6,376,236 | B1 | 4/2002 | Dubensky, Jr. et al. |
| 6,391,632 | B1 | 5/2002 | Dubensky, Jr. et al. |
| 6,426,196 | B1 | 7/2002 | Dubensky, Jr. et al. |
| 6,451,592 | B1 | 9/2002 | Dubensky, Jr. et al. |
| 6,458,560 | B1 | 10/2002 | Dubensky, Jr. et al. |
| 6,465,634 | B1 | 10/2002 | Dubensky, Jr. et al. |
| 6,566,093 | B1 | 5/2003 | Liljestrom et al. |
| 6,592,874 | B2 | 7/2003 | Schlesinger et al. |
| 6,692,750 | B1 | 2/2004 | Sjoberg et al. |
| 6,730,297 | B1 | 5/2004 | Davidson et al. |
| 6,770,283 | B1 | 8/2004 | Garoff et al. |

FOREIGN PATENT DOCUMENTS

| | | |
|---|---|---|
| WO | 99/18226 | 4/1999 |
| WO | 99/18799 | 4/1999 |
| WO | 99/44423 | 9/1999 |
| WO | 00/62735 | 10/2000 |

OTHER PUBLICATIONS

NCBI GenBank Locus SINCG, Version J02363.1, 11703 bp ss-RNA linear VRL Oct. 25, 2000.(9 pages).*

Ying H. et al., Cancer Therapy Using a Self-Replicating RNA Vaccine, Nature Medicine, Jul. 1999, pp. 823-827, vol. 5, No. 7, Nature Publishing Group, New York, USA.

Schlesinger S. et al., "Alphavirus Vectors for Gene Expression and Vaccines", Current Opinion in Biotechnology, Oct. 1999, pp. 434-439, vol. 10, No. 5, London, GB.

Perri, Slyvia et al. "Replicon Vectors Derived from Sindbis Virus and Semliki Forest Virus That Establish Persistent Replication in Host Cells." Journal of Virology, Oct. 2000, pp. 9802-9807, vol. 74, No. 20.

Leitner, Wolfgang W. et al. "Enhancement of Tumor-specific Immune Response With Plasmid DNA Replicon Vectors." Cancer Research, Jan. 1, 2000, pp. 51-55.

Hariharan, Mangala J. et al. "DNA Immunization Againstr Herpes Simplex Virus: Enhanced Efficacy Using a Sindbis Virus-Based Vector." Journal of Virology, Feb. 1998, pp. 950-958, vol. 72, No. 2.

Gardner, Jason P. et al. "Infection of Human Dendritic Cells by a Sindbis Virus Replicon Vector Is Determined by a Single Amino Acid Substitution in the E2 Glycoprotein." Journal of Virology, Dec. 2000, pp. 11849-11857, vol. 74, No. 24.

Polo, John M. et al. "Stable Alphavirus Packaging Cell Lines for Sindbis Virus- and Semliki Forest Virus-Derived Vectors." Proc. Natl. Acad. Sci. USA, Apr. 1999, pp. 4598-4603, vol. 96.

Dubensky, Thomas W., Jr. et al. "Sindbis Virus DNA-Basd Expression Vectors: Utility for In Vitro and In Vivo Gene Transfer." Journal of Virology, Jan. 1996, pp. 508-519, vol. 70, No. 1.

Xiong, Cheng et al. "Sindbis Virus: An Efficient, Broad Host Range Vector for Gene Expression in Animal Cells." Science, Mar. 3, 1989, pp. 1188-1191, vol. 243.

Levis, Robin et al. "Engineered Defecctive Interfering RNAs of Sindbis Virus Express Bacterial Chloramphenicol Acetyltransferase in Avian Cells." Porc. Natl. Acad. Sci. USA, Jul. 1987, pp. 4811-4815, vol. 84.

Murphy A-M et al. "Inhibition of Human Lung Carcinoma Cell Growth by Apoptosis Using Semliki Forest Virus Recombinant Particles." Gene Therapy, 2000, p. 1477-82, vol. 7.

Asselin-Paturel C. et al. "Transfer of the murine IL-12 gene in vivo by a Semiliki Forest virus vector induces B16 tumor regression through inhibition of tumor blood vessel formation monitered by Doppler ultrasonography" Gene Therapy, 1998, p. 615, vol. 5.

(Continued)

*Primary Examiner*—Thaian N. Ton
*Assistant Examiner*—Wu-Cheng Winston Shen
(74) *Attorney, Agent, or Firm*—Darby & Darby P.C.

(57) ABSTRACT

Disclosed herein are new defective Sindbis viral vectors made from wild type Ar-339 Sindbis virus, with differences in replicase and envelope proteins between JT vectors and consensus Sindbis virus sequences, and also between JT and Ar-339 vectors. Also disclosed are plasmids used for the production of the vectors, methods for producing the vectors, methods for treating mammals suffering from tumors and pharmaceutical formulations for use in the treatment methods.

3 Claims, 16 Drawing Sheets

OTHER PUBLICATIONS

Klimp et al. "Activation of Peritoneal Cells Upon in Vivo Transfection with a Recumbinant Alphavirus Expressing GM-CSF." Gene Therapy, Feb. 2000, p. 300-7, vol. 8, No. 4.

Li et al. "Rescue of Sindbis Virus-Specific RNA Replication and Transcription by using Vaccinia Virus Recombinant." J. of Virology, Dec. 1991, p. 6714-23, vol. 65, No. 12.

Cheng et al. "Cancer Immunotherapy using Sindbis Virus Replicon Particles Encoding VP22-Antigen Fusion." Human Gene Therapy, Mar. 1, 2002, p. 553-68, vol. 13, No. 4.

Velders et al. "Eradication of Established Tumors by Vaccination with Venezuelan Equine Encephalitis Virus Replicon Particles Delivering Human Papilomavirus 16 E7 RNA." Cancer Research, Nov. 1, 2001, p. 7861-67, vol. 61, No. 21.

Smerdou et al. "Two-Helper System for Production of Recombinant Semliki Forest Virus Particles." Journal of Virology, vol. 73, No. 2, Feb. 1999, pp. 1092-1098.

Zhang, et al. "Cloning of Human IL-12 p40 and p35 DNA into the Semliki Forest Virus Vector: Expression of IL-12 in Human Tumor Cells." Gene Therapy, 1997, pp. 367-374.

Alemany, et al. "Blood Clearance Rates of Adenovirus Type 5 in Mice." Journal of General Virology, 2000, pp. 2605-2609.

Sung, et al. "TNFa and IFNg Induced by Innate Anti-Adenoviral Immune Responses Inhibit Adenovirus-Mediated Transgene Expression." Molecular Therapy, vol. 3, No. 5, May 2001, pp. 757-767.

Unno, et al. "Oncolytic Viral Therapy for Cervical and Ovarian Cancer Cells by Sindbis Virus AR339 Strain." Clin. Cancer. Res., vol. 11, No. 12, Jun. 15, 2005, pp. 4553-4560.

Pouton, et al. "Key Issues in Non-Viral Gene Delivery." Advanced Drug Delivery Reviews, 2001, pp. 187-203.

Read, et al. "Barriers to Gene Delivery Using Synthetic Vectors." Advances in Genetics, vol. 53, 2005, pp. 19-46.

Higashikawa, et al. "Kinetic Analyses of Stability of Simple and Complex Retorviral Vectors." Virology 280, 2001, pp. 124-131.

DePolo, et al. "The Resistance of Retroviral Vectors Produced from Human Cells to Serum Inactivation In Vivo and In Vitro Is Primate Species Development." Journal of Virology, Aug. 1999, pp. 6708-6714.

Miller, et al. "Targeted Vectors for Gene Therapy." The FASEB Journal, vol. 9, Feb. 1995, pp. 190-199.

Deonarain, "Ligand-Targeted Receiptor-Mediated Vectors for Gene Delivery." Exp. Opin. Ther. Patents, vol. 8, No. 1, 1998, pp. 53-69.

Verma, et al. "Gene Therapy—Promises, Problems and Prospects." Nature, vol. 389, Sep. 18, 1997, pp. 239-242.

Crystal, "Transfer of Genes to Humans: Early Lessons and Obstacles to Success." Science, vol. 270, Oct. 20, 1995, pp. 404-410.

Frolov, et al. "Comparison of the Effects of Sindbis Virus and Sindbis Virus Replicons on Host Cell Protein Synthesis and Cytopathogenicity in BHK Cells." Journal of Virology, vol. 68, No. 3, Mar. 1994, pp. 1721-1727.

* cited by examiner

● Vector A  (n = 5)  (JT-BB/SP6-RhRLuciferase)
■ Vector B  (n = 5)  (SP6-H/JT-RephRLucierase)
▲ Vector C  (n = 5)  (SP6-H/SP6-RhRLuciferase)
▼ Vector D  (n = 5)  (JT-BB/JT-RephRLucierase)
◆ Control   (n = 5)

(Min:30, Max:1000)

Vector A #13,15,16,17

Vector B #18,20,22

Vector C #24,26,27

#15

#22

#27

Open

Organ array

Organ photo

P value (two-tailed) P<0.0001

SEQUENCE LISTING

<160> NUMBER OF SEQ ID NOS: 40

<210> SEQ ID NO 1
<211> LENGTH: 17
<212> TYPE: DNA
<213> ORGANISM: artificial
<220> FEATURE:
<223> OTHER INFORMATION: primer

<400> SEQUENCE: 1
ccccaatgat ccgacca 17

<210> SEQ ID NO 2
<211> LENGTH: 18
<212> TYPE: DNA
<213> ORGANISM: artificial
<220> FEATURE:
<223> OTHER INFORMATION: primer

<400> SEQUENCE: 2
attgacggcg tagtacac 18

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
gtatcaagta ggatccggag 20

<210> SEQ ID NO 4
<211> LENGTH: 27
<212> TYPE: DNA
<213> ORGANISM: artificial
<220> FEATURE:
<223> OTHER INFORMATION: primer

<400> SEQUENCE: 4
aaaacaaatt ttgttgatta ataaaag 27

<210> SEQ ID NO 5
<211> LENGTH: 17
<212> TYPE: DNA
<213> ORGANISM: artificial
<220> FEATURE:
<223> OTHER INFORMATION: primer

<400> SEQUENCE: 5
ccccaatgat ccgacca 17

<210> SEQ ID NO 6
<211> LENGTH: 28
<212> TYPE: DNA
<213> ORGANISM: artificial
<220> FEATURE:
<223> OTHER INFORMATION: primer

<400> SEQUENCE: 6
aaaacaaaat tttgttgatt aataaaag 28

-continued

<210> SEQ ID NO 7
<211> LENGTH: 18
<212> TYPE: DNA
<213> ORGANISM: artificial
<220> FEATURE:
<223> OTHER INFORMATION: primer

<400> SEQUENCE: 7
attgacggcg tagtacac 18

<210> SEQ ID NO 8
<211> LENGTH: 24
<212> TYPE: DNA
<213> ORGANISM: artificial
<220> FEATURE:
<223> OTHER INFORMATION: primer

<400> SEQUENCE: 8
gtaacaagat ctcgtgccgt gaca 24

<210> SEQ ID NO 9
<211> LENGTH: 22
<212> TYPE: DNA
<213> ORGANISM: artificial
<220> FEATURE:
<223> OTHER INFORMATION: primer

<400> SEQUENCE: 9
ggcacgagat cttgttacca gc 22

<210> SEQ ID NO 10
<211> LENGTH: 29
<212> TYPE: DNA
<213> ORGANISM: artificial
<220> FEATURE:
<223> OTHER INFORMATION: primer

<400> SEQUENCE: 10
ctttctttcc taggcacaca gtcattctt 29

<210> SEQ ID NO 11
<211> LENGTH: 25
<212> TYPE: DNA
<213> ORGANISM: artificial
<220> FEATURE:
<223> OTHER INFORMATION: primer

<400> SEQUENCE: 11
gactgtgtgc ctaggaaaga aagtg 25

<210> SEQ ID NO 12
<211> LENGTH: 22
<212> TYPE: DNA
<213> ORGANISM: artificial
<220> FEATURE:
<223> OTHER INFORMATION: primer

<400> SEQUENCE: 12
cacacccagg tcctccaaga tc 22

<210> SEQ ID NO 13
<211> LENGTH: 22
<212> TYPE: DNA
<213> ORGANISM: artificial
<220> FEATURE:
<223> OTHER INFORMATION: primer -continued

<400> SEQUENCE: 13
gcatcattcg acaaaagcca ag 22

<210> SEQ ID NO 14
<211> LENGTH: 30
<212> TYPE: DNA
<213> ORGANISM: artificial
<220> FEATURE:
<223> OTHER INFORMATION: primer

<400> SEQUENCE: 14
ctcttctaga ggtggtggtg ttgtagtatt 30

<210> SEQ ID NO 15
<211> LENGTH: 25
<212> TYPE: DNA
<213> ORGANISM: artificial
<220> FEATURE:
<223> OTHER INFORMATION: primer

<400> SEQUENCE: 15
ggatcccctg aaaaggctgt ttaag 25

<210> SEQ ID NO 16
<211> LENGTH: 23
<212> TYPE: DNA
<213> ORGANISM: artificial
<220> FEATURE:
<223> OTHER INFORMATION: primer

<400> SEQUENCE: 16
tcatgtctga tcaagtccgg tga 23

<210> SEQ ID NO 17
<211> LENGTH: 24
<212> TYPE: DNA
<213> ORGANISM: artificial
<220> FEATURE:
<223> OTHER INFORMATION: primer

<400> SEQUENCE: 17
ggacttgatc agacatgacg acca 24

<210> SEQ ID NO 18
<211> LENGTH: 31
<212> TYPE: DNA
<213> ORGANISM: artificial
<220> FEATURE:
<223> OTHER INFORMATION: primer

<400> SEQUENCE: 18
tttttgaaat gttaaaaaca aaattttgtt g 31

<210> SEQ ID NO 19
<211> LENGTH: 85
<212> TYPE: DNA
<213> ORGANISM: artificial
<220> FEATURE:
<223> OTHER INFORMATION: primer

<400> SEQUENCE: 19
cccacatgtg ggaggctaga gtacttaata cgactcacta taggattgac ggcgtagtac 60
acactattga atcaaacagc cgacc 85

-continued

```
<210> SEQ ID NO 20
<211> LENGTH: 84
<212> TYPE: DNA
<213> ORGANISM: artificial
<220> FEATURE:
<223> OTHER INFORMATION: primer

<400> SEQUENCE: 20

cccacatgtg ggaggctaga gtacatttag gtgacactat agaaattgac ggcgtagtac     60

acactattga atcaaacagc cgac                                            84


<210> SEQ ID NO 21
<211> LENGTH: 80
<212> TYPE: DNA
<213> ORGANISM: artificial
<220> FEATURE:
<223> OTHER INFORMATION: primer

<400> SEQUENCE: 21

ggcgcgcctc tagactagcc taggtatgga agatcttccg cggatccgcc tagtgcaatt     60

ggtcggctgt ttgattcaat                                                 80


<210> SEQ ID NO 22
<211> LENGTH: 85
<212> TYPE: DNA
<213> ORGANISM: artificial
<220> FEATURE:
<223> OTHER INFORMATION: primer

<400> SEQUENCE: 22

aggctagtct agaggcgcgc cgatctcacg tgagcatgcg tttaaactgg gcccaatgtt     60

aacatttcaa aaaaaaaaaa aaaaa                                           85


<210> SEQ ID NO 23
<211> LENGTH: 85
<212> TYPE: DNA
<213> ORGANISM: artificial
<220> FEATURE:
<223> OTHER INFORMATION: primer

<400> SEQUENCE: 23

ggtgatgacg tcctcgaggc ggccgcttaa ttaatttaaa tttttttttt tttttttttt     60

tttttttttt tttttttga aatgt                                            85


<210> SEQ ID NO 24
<211> LENGTH: 17
<212> TYPE: DNA
<213> ORGANISM: artificial
<220> FEATURE:
<223> OTHER INFORMATION: primer

<400> SEQUENCE: 24

atatatatcc cacatgt                                                    17


<210> SEQ ID NO 25
<211> LENGTH: 13
<212> TYPE: DNA
<213> ORGANISM: artificial
<220> FEATURE:
<223> OTHER INFORMATION: primer

<400> SEQUENCE: 25

gcgcgcctct aga                                                        13
```

-continued

<210> SEQ ID NO 26
<211> LENGTH: 16
<212> TYPE: DNA
<213> ORGANISM: artificial
<220> FEATURE:
<223> OTHER INFORMATION: primer

<400> SEQUENCE: 26
aggctagtct agaggc 16

<210> SEQ ID NO 27
<211> LENGTH: 14
<212> TYPE: DNA
<213> ORGANISM: artificial
<220> FEATURE:
<223> OTHER INFORMATION: primer

<400> SEQUENCE: 27
ggtgatgacg tcct 14

<210> SEQ ID NO 28
<211> LENGTH: 38
<212> TYPE: DNA
<213> ORGANISM: artificial
<220> FEATURE:
<223> OTHER INFORMATION: primer

<400> SEQUENCE: 28
gcaaaagaag cgtcatcgat gactttaccc tgaccagc 38

<210> SEQ ID NO 29
<211> LENGTH: 38
<212> TYPE: DNA
<213> ORGANISM: artificial
<220> FEATURE:
<223> OTHER INFORMATION: primer

<400> SEQUENCE: 29
gctggtcagg gtaaagtcat cgatgacgct tcttttgc 38

<210> SEQ ID NO 30
<211> LENGTH: 35
<212> TYPE: DNA
<213> ORGANISM: artificial
<220> FEATURE:
<223> OTHER INFORMATION: primer

<400> SEQUENCE: 30
ctacatgtcg cttaagcagg atcacaccgt taaag 35

<210> SEQ ID NO 31
<211> LENGTH: 35
<212> TYPE: DNA
<213> ORGANISM: artificial
<220> FEATURE:
<223> OTHER INFORMATION: primer

<400> SEQUENCE: 31
ctttaacggt gtgatcctgc ttaagcgaca tgtag 35

<210> SEQ ID NO 32
<211> LENGTH: 40
<212> TYPE: DNA
<213> ORGANISM: artificial
<220> FEATURE:
<223> OTHER INFORMATION: primer -continued

<400> SEQUENCE: 32
cgggcccgca cgcttataca tcctacctgg aagaatcatc 40

<210> SEQ ID NO 33
<211> LENGTH: 40
<212> TYPE: DNA
<213> ORGANISM: artificial
<220> FEATURE:
<223> OTHER INFORMATION: primer

<400> SEQUENCE: 33
gatgattctt ccaggtagga tgtataagcg tgcgggcccg 40

<210> SEQ ID NO 34
<211> LENGTH: 36
<212> TYPE: DNA
<213> ORGANISM: artificial
<220> FEATURE:
<223> OTHER INFORMATION: primer

<400> SEQUENCE: 34
gacttgatcc gacatgacga ccacacggtc caaggg 36

<210> SEQ ID NO 35
<211> LENGTH: 36
<212> TYPE: DNA
<213> ORGANISM: artificial
<220> FEATURE:
<223> OTHER INFORMATION: primer

<400> SEQUENCE: 35
cccttggacc gtgtggtcgt catgtcggat caagtc 36

<210> SEQ ID NO 36
<211> LENGTH: 9928
<212> TYPE: DNA
<213> ORGANISM: Sindbis virus

<400> SEQUENCE: 36
attgacggcg tagtacacac tattgaatca aacagccgac caattgcact accatcacaa 60
tggagaagcc agtagtaaac gtagacgtag acccccagag tccgtttgtc gtgcaactgc 120
aaaaaagctt cccgcaattt gaggtagtag cacagcaggt cactccaaat gaccatgcta 180
atgccagagc attttcgcat ctggccagta aactaatcga gctggaggtt cctaccacag 240
cgacgatctt ggacataggc agcgcaccgg ctcgtagaat gttttccgag caccagtatc 300
attgtgtctg ccccatgcgt agtccagaag acccggaccg catgatgaaa tatgccagta 360
aactggcgga aaaagcgtgc aagattacaa acaagaactt gcatgagaag attaaggatc 420
tccggaccgt acttgatacg ccggatgctg aaacaccatc gctctgcttt cacaacgatg 480
ttacctgcaa catgcgtgcc gaatattccg tcatgcagga cgtgtatatc aacgctcccg 540
gaactatcta tcatcaggct atgaaaggcg tgcggaccct gtactggatt ggcttcgaca 600
ccacccagtt catgttctcg gctatggcag gttcgtaccc tgcgtacaac accaactggg 660
ccgacgagaa agtccttgaa gcgcgtaaca tcggactttg cagcacaaag ctgagtgaag 720
gtaggacagg aaaattgtcg ataatgagga agaaggagtt gaagcccggg tcgcgggttt 780
atttctccgt aggatcgaca ctttatccag aacacagagc cagcttgcag agctggcatc 840
ttccatcggt gttccacttg aatggaaagc agtcgtacac ttgccgctgt gatacagtgg 900

-continued

```
tgagttgcga aggctacgta gtgaagaaaa tcaccatcag tcccgggatc acgggagaaa    960
ccgtgggata cgcggttaca cacaatagcg agggcttctt gctatgcaaa gttactgaca   1020
cagtaaaagg agaacgggta tcgttccctg tgtgcacgta catcccggcc accatatgcg   1080
atcagatgac tggtataatg gccacggata tatcacctga cgatgcacaa aaacttctgg   1140
ttgggctcaa ccagcgaatt gtcattaacg gtaggactaa caggaacacc aacaccatgc   1200
aaaattacct tctgccgatc atagcacaag ggttcagcaa atgggctaag gagcgcaagg   1260
atgatcttga taacgagaaa atgctgggta ctagagaacg caagcttacg tatggctgct   1320
tgtgggcgtt tcgcactaag aaagtacatt cgttttatcg cccacctgga acgcagacca   1380
tcgtaaaagt cccagcctct tttagcgctt ttcccatgtc gtccgtatgg acgacctctt   1440
tgcccatgtc gctgaggcag aaattgaaac tggcattgca accaaagaag gaggaaaaac   1500
tgctgcaggt ctcggaggaa ttagtcatgg aggccaaggc tgcttttgag gatgctcagg   1560
aggaagccag agcggagaag ctccgagaag cacttccacc attagtggca gacaaaggca   1620
tcgaggcagc cgcagaagtt gtctgcgaag tggaggggct ccaggcggac atcggagcag   1680
cattagttga aaccccgcgc ggtcacgtaa ggataatacc tcaagcaaat gaccgtatga   1740
tcggacagta tatcgttgtc tcgccaaact ctgtgctgaa gaatgccaaa ctcgcaccag   1800
cgcacccgct agcagatcag gttaagatca taacacactc cggaagatca ggaaggtacg   1860
cggtcgaacc atacgacgct aaagtactga tgccagcagg aggtgccgta ccatggccag   1920
aattcctagc actgagtgag agcgccacgt tagtgtacaa cgaaagagag tttgtgaacc   1980
gcaaactata ccacattgcc atgcatggcc ccgccaagaa tacagaagag gagcagtaca   2040
aggttacaaa ggcagagctt gcagaaacag agtacgtgtt tgacgtggac aagaagcgtt   2100
gcgttaagaa ggaagaagcc tcaggtctgg tcctctcggg agaactgacc aaccctccct   2160
atcatgagct agctctggag ggactgaaga cccgacctgc ggtcccgtac aaggtcgaaa   2220
caataggagt gataggcaca ccggggtcgg gcaagtcagc tattatcaag tcaactgtca   2280
cggcacgaga tcttgttacc agcggaaaga aagaaaattg tcgcgaaatt gaggccgacg   2340
tgctaagact gaggggtatg cagattacgt cgaagacagt agattcggtt atgctcaacg   2400
gatgccacaa agccgtagaa gtgctgtacg ttgacgaagc gttcgcgtgc cacgcaggag   2460
cactacttgc cttgattgct atcgtcaggc cccgcaagaa ggtagtacta tgcggagacc   2520
ccatgcaatg cggattcttc aacatgatgc aactaaaggt acatttcaat caccctgaaa   2580
aagacatatg caccaagaca ttctacaagt atatctcccg gcgttgcaca cagccagtta   2640
cagctattgt atcgacactg cattacgatg gaaagatgaa aaccacgaac ccgtgcaaga   2700
agaacattga aatcgatatt acaggggcca caaagccgaa gccaggggat atcatcctga   2760
catgtttccg cgggtgggtt aagcaattgc aaatcgacta tcccggacat gaagtaatga   2820
cagccgcggc ctcacaaggg ctaaccagaa aaggagtgta tgccgtccgg caaaaagtca   2880
atgaaaaccc actgtacgcg atcacatcag agcatgtgaa cgtgttgctc acccgcactg   2940
aggacaggct agtgtggaaa accttgcagg gcgacccatg gattaagcag ctcactaaca   3000
tacctaaagg aaactttcag gctactatag aggactggga agctgaacac aagggaataa   3060
ttgctgcaat aaacagcccc actccccgtg ccaatccgtt cagctgcaag accaacgttt   3120
gctgggcgaa agcattggaa ccgatactag ccacggccgg tatcgtactt accggttgcc   3180
agtggagcga actgttccca cagtttgcgg atgacaaacc acattcggcc atttacgcct   3240
tagacgtaat ttgcattaag tttttcggca tggacttgac aagcggactg ttttctaaac   3300
```

-continued agagcatccc actaacgtac catcccgccg attcagcgag gccggtagct cattgggaca 3360
acagcccagg aacccgcaag tatgggtacg atcacgccat tgccgccgaa ctctcccgta 3420
gatttccggt gttccagcta gctgggaagg gcacacaact tgatttgcag acggggagaa 3480
ccagagttat ctctgcacag cataacctgg tcccggtgaa ccgcaatctt cctcacgcct 3540
tagtccccga gtacaaggag aagcaacccg gcccggtcga aaaattcttg aaccagttca 3600
aacaccactc agtacttgtg gtatcagagg aaaaaattga agctccccgt aagagaatcg 3660
aatggatcgc cccgattggc atagccggtg cagataagaa ctacaacctg gctttcgggt 3720
ttccgccgca ggcacggtac gacctggtgt tcatcaacat tggaactaaa tacagaaacc 3780
accactttca gcagtgcgaa gaccatgcgg cgaccttaaa aaccctttcg cgttcggccc 3840
tgaattgcct taacccagga ggcaccctcg tggtgaagtc ctatggctac gccgaccgca 3900
acagtgagga cgtagtcacc gctcttgcca gaaagtttgt cagggtgtct gcagcgagac 3960
cagattgtgt ctcaagcaat acagaaatgt acctgatttt ccgacaacta gacaacagcc 4020
gtacacggca attcaccccg caccatctga attgcgtgat ttcgtccgtg tatgagggta 4080
caagagatgg agttggagcc gcgccgtcat accgcaccaa aagggagaat attgctgact 4140
gtcaagagga agcagttgtc aacgcagcca atccgctggg tagaccaggc gaaggagtct 4200
gccgtgccat ctataaacgt tggccgacca gttttaccga ttcagccacg gagacaggca 4260
ccgcaagaat gactgtgtgc ctaggaaaga aagtgatcca cgcggtcggc cctgatttcc 4320
ggaagcaccc agaagcagaa gccttgaaat tgctacaaaa cgcctaccat gcagtggcag 4380
acttagtaaa tgaacataac atcaagtctg tcgccattcc actgctatct acaggcattt 4440
acgcagccgg aaaagaccgc cttgaagtat cacttaactg cttgacaacc gcgctagaca 4500
gaactgacgc ggacgtaacc atctattgcc tggataagaa gtggaaggaa agaatcgacg 4560
cggcactcca acttaaggag tctgtaacag agctgaagga tgaagatatg gagatcgacg 4620
atgagttagt atggatccat ccagacagtt gcttgaaggg aagaaaggga ttcagtacta 4680
caaaaggaaa attgtattcg tacttcgaag gcaccaaatt ccatcaagca gcaaaagaca 4740
tggcggagat aaaggtcctg ttccctaatg accaggaaag taatgaacaa ctgtgtgcct 4800
acatattggg tgagaccatg gaagcaatcc gcgaaaagtg cccggtcgac cataacccgt 4860
cgtctagccc gcccaaaacg ttgccgtgcc tttgcatgta tgccatgacg ccagaaaggg 4920
tccacagact tagaagcaat aacgtcaaag aagttacagt atgctcctcc acccccttc 4980 ctaagcacaa aattaagaat gttcagaagg ttcagtgcac gaaagtagtc ctgtttaatc 5040
cgcacactcc cgcattcgtt cccgcccgta agtacataga agtgccagaa cagcctaccg 5100
ctcctcctgc acaggccgag gaggcccccg aagttgtagc gacaccgtca ccatctacag 5160
ctgataacac ctcgcttgat gtcacagaca tctcactgga tatggatgac agtagcgaag 5220
gctcactttt ttcgagcttt agcggatcgg acaactctat tactagtatg gacagttggt 5280
cgtcaggacc tagttcacta gagatagtag accgaaggca ggtggtggtg gctgacgttc 5340
atgccgtcca agagcctgcc cctattccac cgccaaggct aaagaagatg gcccgcctgg 5400
cagcggcaag aaaagagccc actccaccgg caagcaatag ctctgagtcc ctccacctct 5460
cttttggtgg ggtatccatg tccctcggat caattttcga cggagagacg gcccgccagg 5520
cagcggtaca acccctggca acaggcccca cggatgtgcc tatgtctttc ggatcgtttt 5580
ccgacggaga gattgatgag ctgagccgca gagtaactga gtccgaaccc gtcctgtttg 5640

-continued gatcatttga accgggcgaa gtgaactcaa ttatatcgtc ccgatcagcc gtatcttttc 5700
cactacgcaa gcagagacgt agacgcagga gcaggaggac tgaatactga ctaaccgggg 5760
taggtgggta catattttcg acggacacag gccctgggca cttgcaaaag aagtccgttc 5820
tgcagaacca gcttacagaa ccgaccttgg agcgcaatgt cctggaaaga attcatgccc 5880
cggtgctcga cacgtcgaaa gaggaacaac tcaaactcag gtaccagatg atgcccaccg 5940
aagccaacaa aagtaggtac cagtctcgta aagtagaaaa tcagaaagcc ataaccactg 6000
agcgactact gtcaggacta cgactgtata actctgccac agatcagcca gaatgctata 6060
agatcaccta tccgaaacca ttgtactcca gtagcgtacc ggcgaactac tccgatccac 6120
agttcgctgt agctgtctgt aacaactatc tgcatgagaa ctatccgaca gtagcatctt 6180
atcagattac tgacgagtac gatgcttact tggatatggt agacgggaca gtcgcctgcc 6240
tggatactgc aaccttctgc cccgctaagc ttagaagtta cccgaaaaaa catgagtata 6300
gagccccgaa tatccgcagt gcggttccat cagcgatgca gaacacgcta caaaatgtgc 6360
tcattgccgc aactaaaaga aattgcaacg tcacgcagat gcgtgaactg ccaacactgg 6420
actcagcgac attcaatgtc gaatgctttc gaaaatatgc atgtaatgac gagtattggg 6480
aggagttcgc tcggaagcca attaggatta ccactgagtt tgtcaccgca tatgtagcta 6540
gactgaaagg ccctaaggcc gccgcactat ttgcaaagac gtataatttg gtcccattgc 6600
aagaagtgcc tatggataga ttcgtcatgg acatgaaaag agacgtgaaa gttacaccag 6660
gcacgaaaca cacagaagaa agaccgaaag tacaagtgat acaagccgca gaacccctgg 6720
cgactgctta cttatgcggg attcaccggg aattagtgcg taggcttacg gccgtcttgc 6780
ttccaaacat tcacacgctt tttgacatgt cggcggagga ttttgatgca atcatagcag 6840
aacacttcaa gcaaggcgac ccggtactgg agacggatat cgcatcattc gacaaaagcc 6900
aagacgacgc tatggcgtta accggtctga tgatcttgga ggacctgggt gtggatcaac 6960
cactactcga cttgatcgag tgcgcctttg gagaaatatc atccacccat ctacctacgg 7020
gtactcgttt taaattcggg gcgatgatga aatccggaat gttcctcaca ctttttgtca 7080
acacagtttt gaatgtcgtt atcgccagca gagtactaga agagcggctt aaaacgtcca 7140
gatgtgcagc gttcattggc gacgacaaca tcatacatgg agtagtatct gacaaagaaa 7200
tggctgagag gtgcgccacc tggctcaaca tggaggttaa gatcatcgac gcagtcatcg 7260
gtgagagacc accttacttc tgcggcggat ttatcttgca agattcggtt acttccacag 7320
cgtgccgcgt ggcggacccc ctgaaaaggc tgtttaagtt gggtaaaccg ctcccagccg 7380
acgacgagca agacgaagac agaagacgcg ctctgctaga tgaaacaaag gcgtggttta 7440
gagtaggtat aacaggcact ttagcagtgg ccgtgacgac ccggtatgag gtagacaata 7500
ttacacctgt cctactggca ttgagaactt ttgcccagag caaaagagca ttccaagcca 7560
tcagagggga aataaagcat ctctacggtg gtcctaaata gtcagcatag tacatttcat 7620
ctgactaata ctacaacacc accacctcta gaggcgcgcc gatctcacgt gagcatgcgt 7680
ttaaactggg cccaatgttc cccaatgatc cgaccagcaa aactcgatgt acttccgagg 7740
aactgatgtg cataatgcat caggctggta cattagatcc ccgcttaccg cgggcaatat 7800
agcaacacta aaaactcgat gtacttccga ggaagcgcag tgcataatgc tgcgcagtgt 7860
tgccacataa ccactatatt aaccatttat ctagcggacg ccaaaaactc aatgtatttc 7920
tgaggaagcg tggtgcataa tgccacgcag cgtctgcata acttttatta tttcttttat 7980
taatcaacaa aattttgttt ttaacatttc aaaaaaaaaa aaaaaaaaaa aaaaaaaaaa 8040

-continued aaaaaaaatt taaattaatt aagcggccgc ctcgaggacg tcaggtggca cttttcgggg 8100
aaatgtgcgc ggaaccccta tttgtttatt tttctaaata cattcaaata tgtatccgct 8160
catgagacaa taaccctgat aaatgcttca ataatattga aaaaggaaga gtatgagtat 8220
tcaacatttc cgtgtcgccc ttattccctt ttttgcggca ttttgccttc ctgtttttgc 8280
tcacccagaa acgctggtga aagtaaaaga tgctgaagat cagttgggtg cacgagtggg 8340
ttacatcgaa ctggatctca acagcggtaa gatccttgag agttttcgcc ccgaagaacg 8400
ttttccaatg atgagcactt ttaaagttct gctatgtggc gcggtattat cccgtattga 8460
cgccgggcaa gagcaactcg gtcgccgcat acactattct cagaatgact tggttgagta 8520
ctcaccagtc acagaaaagc atcttacgga tggcatgaca gtaagagaat tatgcagtgc 8580
tgccataacc atgagtgata acactgcggc caacttactt ctgacaacga tcggaggacc 8640
gaaggagcta accgcttttt tgcacaacat gggggatcat gtaactcgcc ttgatcgttg 8700
ggaaccggag ctgaatgaag ccataccaaa cgacgagcgt gacaccacga tgcctgtagc 8760
aatggcaaca acgttgcgca aactattaac tggcgaacta cttactctag cttcccggca 8820
acaattaata gactggatgg aggcggataa agttgcagga ccacttctgc gctcggccct 8880
tccggctggc tggtttattg ctgataaatc tggagccggt gagcgtgggt ctcgcggtat 8940
cattgcagca ctggggccag atggtaagcc ctcccgtatc gtagttatct acacgacggg 9000
gagtcaggca actatggatg aacgaaatag acagatcgct gagataggtg cctcactgat 9060
taagcattgg taactgtcag accaagttta ctcatatata ctttagattg atttaaaact 9120
tcatttttaa tttaaaagga tctaggtgaa gatccttttt gataatctca tgaccaaaat 9180
cccttaacgt gagttttcgt tccactgagc gtcagacccc gtagaaaaga tcaaaggatc 9240
ttcttgagat cctttttttc tgcgcgtaat ctgctgcttg caaacaaaaa aaccaccgct 9300
accagcggtg gtttgtttgc cggatcaaga gctaccaact ctttttccga aggtaactgg 9360
cttcagcaga gcgcagatac caaatactgg tcttctagtg tagccgtagt taggccacca 9420
cttcaagaac tctgtagcac cgcctacata cctcgctctg ctaatcctgt taccagtggc 9480
tgctgccagt ggcgataagt cgtgtcttac cgggttggac tcaagacgat agttaccgga 9540
taaggcgcag cggtcgggct gaacgggggg ttcgtgcaca cagcccagct tggagcgaac 9600
gacctacacc gaactgagat acctacagcg tgagctatga gaaagcgcca cgcttcccga 9660
agggagaaag gcggacaggt atccggtaag cggcagggtc ggaacaggag agcgcacgag 9720
ggagcttcca gggggaaacg cctggtatct ttatagtcct gtcgggtttc gccacctctg 9780
acttgagcgt cgatttttgt gatgctcgtc aggggggcgg agcctatgga aaaacgccag 9840
caacgcggcc tttttacggt tcctggcctt ttgctggcct tttgctcaca tgtgggaggc 9900
tagagtacat ttaggtgaca ctatagaa 9928

<210> SEQ ID NO 37
<211> LENGTH: 6711
<212> TYPE: DNA
<213> ORGANISM: Sindbis virus

<400> SEQUENCE: 37
attgacggcg tagtacacac tattgaatca aacagccgac caattgcact accatcacaa 60
tggagaagcc agtagtaaac gtagacgtag acccccagag tccgtttgtc gtgcaactgc 120
aaaaaagctt cccgcaattt gaggtagtag cacagcaggt cactccaaat gaccatgcta 180

-continued

```
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tatgccagta    360
aactggcgga aaaagcgtgc aagattacaa acaagaactt gcatgagaag attaaggatc    420
tccggatccc ctgaaaaggc tgtttaagtt gggtaaaccg ctcccagccg acgacgagca    480
agacgaagac agaagacgcg ctctgctaga tgaaacaaag gcgtggttta gagtaggtat    540
aacaggcact ttagcagtgg ccgtgacgac ccggtatgag gtagacaata ttacacctgt    600
cctactggca ttgagaactt ttgcccagag caaaaagagca ttccaagcca tcagagggga    660
aataaagcat ctctacggtg gtcctaaata gtcagcatag tacatttcat ctgactaata    720
ctacaacacc accaccatga atagaggatt ctttaacatg ctcggccgcc gccccttccc    780
ggcccccact gccatgtgga ggccgcggag aaggaggcag gcggccccga tgcctgcccg    840
caacgggctg gcttctcaaa tccagcaact gaccacagcc gtcagtgccc tagtcattgg    900
acaggcaact agacctcaac ccccacgtcc acgccagcca ccgcgccaga agaagcaggc    960
gcccaagcaa ccaccgaagc cgaagaaacc aaaaacgcag gagaagaaga agaagcaacc   1020
tgcaaaaccc aaacccggaa agagacagcg catggcactt aagttggagg ccgacagatt   1080
gttcgacgtc aagaacgagg acggagatgt catcgggcac gcactggcca tggaaggaaa   1140
ggtaatgaaa cctctgcacg tgaaaggaac catcgaccac cctgtgctat caaagctcaa   1200
atttaccaag tcgtcagcat acgacatgga gttcgcacag ttgccagtca acatgagaag   1260
tgaggcattc acctacacca gtgaacaccc cgaaggattc tataactggc accacggagc   1320
ggtgcagtat agtggaggta gatttaccat ccctcgcgga gtaggaggca gaggagacag   1380
cggtcgtccg atcatggata actccggtcg ggttgtcgcg atagtcctcg gtggagctga   1440
tgaaggaaca cgaactgccc tttcggtcgt cacctggaat agtaaaggga agacaattaa   1500
gacgaccccg gaagggacag aagagtggtc cgcagcacca ctggtcacgg caatgtgttt   1560
gctcggaaat gtgagcttcc catgcgaccg cccgcccaca tgctataccc gcgaaccttc   1620
cagagccctc gacatccttg aagagaacgt gaaccatgag gcctacgata ccctgctcaa   1680
tgccatattg cggtgcggat cgtctggcag aagcaaaaga agcgtcactg acgactttac   1740
cctgaccagc ccctacttgg gcacatgctc gtactgccac catactgaac cgtgcttcag   1800
ccctgttaag atcgagcagg tctgggacga agcggacgat aacaccatac gcatacagac   1860
ttccgcccag tttggatacg accaaagcgg agcagcaagc gcaaacaagt accgctacat   1920
gtcgcttgag caggatcaca ccgttaaaga aggcaccatg gatgacatca agattagcac   1980
ctcaggaccg tgtagaaggc ttagctacaa aggatacttt ctcctcgcaa aatgccctcc   2040
aggggacagc gtaacggtta gcatagtgag tagcaactca gcaacgtcat gtacactggc   2100
ccgcaagata aaaccaaaat tcgtgggacg ggaaaaatat gatctacctc ccgttcacgg   2160
taaaaaaatt ccttgcacag tgtacgaccg tctgaaagaa acaactgcag gctacatcac   2220
tatgcacagg ccgggaccgc acgcttatac atcctacctg aaagaatcat cagggaaagt   2280
ttacgcaaag ccgccatctg ggaagaacat tacgtatgag tgcaagtgcg gcgactacaa   2340
gaccggaacc gtttcgaccc gcaccgaaat cactggttgc accgccatca agcagtgcgt   2400
cgcctataag agcgaccaaa cgaagtgggt cttcaactca ccggacttga tcagacatga   2460
cgaccacacg gcccaaggga aattgcattt gcctttcaag ttgatcccga gtacctgcat   2520
ggtccctgtt gcccacgcgc cgaatgtaat acatggcttt aaacacatca gcctccaatt   2580
```

-continued

```
agatacagac cacttgacat tgctcaccac caggagacta ggggcaaacc cggaaccaac   2640
cactgaatgg atcgtcggaa agacggtcag aaacttcacc gtcgaccgag atggcctgga   2700
atacatatgg ggaaatcatg agccagtgag ggtctatgcc caagagtcag caccaggaga   2760
ccctcacgga tggccacacg aaatagtaca gcattactac catcgccatc ctgtgtacac   2820
catcttagcc gtcgcatcag ctaccgtggc gatgatgatt ggcgtaactg ttgcagtgtt   2880
atgtgcctgt aaagcgcgcc gtgagtgcct gacgccatac gccctggccc caaacgccgt   2940
aatcccaact tcgctggcac tcttgtgctg cgttaggtcg gccaatgctg aaacgttcac   3000
cgagaccatg agttacttgt ggtcgaacag tcagccgttc ttctgggtcc agttgtgcat   3060
acctttggcc gctttcatcg ttctaatgcg ctgctgctcc tgctgcctgc ctttttttagt   3120
ggttgccggc gcctacctgg cgaaggtaga cgcctacgaa catgcgacca ctgttccaaa   3180
tgtgccacag ataccgtata aggcacttgt tgaaagggca gggtatgccc cgctcaattt   3240
ggagatcact gtcatgtcct cggaggtttt gccttccacc aaccaagagt acattacctg   3300
caaattcacc actgtggtcc cctccccaaa aatcaaatgc tgcggctcct tggaatgtca   3360
gccggccgtt catgcagact atacctgcaa ggtcttcgga ggggtctacc cctttatgtg   3420
gggaggagcg caatgttttt gcgacagtga gaacagccag atgagtgagg cgtacgtcga   3480
actgtcagca gattgcgcgt ctgaccacgc gcaggcgatt aaggtgcaca ctgccgcgat   3540
gaaagtagga ctgcgtatag tgtacgggaa cactaccagt ttcctagatg tgtacgtgaa   3600
cggagtcaca ccaggaacgt ctaaagactt gaaagtcata gctggaccaa tttcagcatc   3660
gtttacgcca ttcgatcata aggtcgttat ccatcgcggc ctggtgtaca actatgactt   3720
cccggaatat ggagcgatga aaccaggagc gtttggagac attcaagcta cctccttgac   3780
tagcaaggat ctcatcgcca gcacagacat taggctactc aagccttccg ccaagaacgt   3840
gcatgtcccg tacacgcagg ccgcatcagg atttgagatg tggaaaaaca actcaggccg   3900
cccactgcag gaaaccgcac ctttcgggtg taagattgca gtaaatccgc tccgagcggt   3960
ggactgttca tacgggaaca ttcccatttc tattgacatc ccgaacgctg cctttatcag   4020
gacatcagat gcaccactgg tctcaacagt caaatgtgaa gtcagtgagt gcacttattc   4080
agcagacttc ggcgggatgg ccaccctgca gtatgtatcc gaccgcgaag gtcaatgccc   4140
cgtacattcg cattcgagca cagcaactct ccaagagtcg acagtacatg tcctggagaa   4200
aggagcggtg acagtacact ttagcaccgc gagtccacag gcgaacttta tcgtatcgct   4260
gtgtgggaag aagacaacat gcaatgcaga atgtaaacca ccagctgacc atatcgtgag   4320
caccccgcac aaaaatgacc aagaatttca agccgccatc tcaaaaacat catggagttg   4380
gctgtttgcc cttttcggcg gcgcctcgtc gctattaatt ataggactta tgatttttgc   4440
ttgcagcatg atgctgacta gcacacgaag atgaccgcta cgccccaatg atccgaccag   4500
caaaactcga tgtacttccg aggaactgat gtgcataatg catcaggctg gtacattaga   4560
tccccgctta ccgcgggcaa tatagcaaca ctaaaaactc gatgtacttc cgaggaagcg   4620
cagtgcataa tgctgcgcag tgttgccaca taaccactat attaaccatt tatctagcgg   4680
acgccaaaaa ctcaatgtat ttctgaggaa gcgtggtgca taatgccacg cagcgtctgc   4740
ataactttta ttatttcttt tattaatcaa caaaattttg tttttaacat ttcaaaaaaa   4800
aaaaaaaaaa aaaaaaaaaa aaaaaaaaaa atttaaatta attaagcggc cgcctcgagg   4860
acgtcaggtg gcacttttcg ggaaatgtg cgcggaaccc ctatttgttt atttttctaa   4920
```

-continued

```
atacattcaa atatgtatcc gctcatgaga caataaccct gataaatgct tcaataatat   4980

tgaaaaagga agagtatgag tattcaacat ttccgtgtcg cccttattcc cttttttgcg   5040

gcattttgcc ttcctgtttt tgctcaccca gaaacgctgg tgaaagtaaa agatgctgaa   5100

gatcagttgg gtgcacgagt gggttacatc gaactggatc tcaacagcgg taagatcctt   5160

gagagttttc gccccgaaga acgttttcca atgatgagca cttttaaagt tctgctatgt   5220

ggcgcggtat tatcccgtat tgacgccggg caagagcaac tcggtcgccg catacactat   5280

tctcagaatg acttggttga gtactcacca gtcacagaaa agcatcttac ggatggcatg   5340

acagtaagag aattatgcag tgctgccata accatgagtg ataacactgc ggccaactta   5400

cttctgacaa cgatcggagg accgaaggag ctaaccgctt ttttgcacaa catgggggat   5460

catgtaactc gccttgatcg ttgggaaccg gagctgaatg aagccatacc aaacgacgag   5520

cgtgacacca cgatgcctgt agcaatggca acaacgttgc gcaaactatt aactggcgaa   5580

ctacttactc tagcttcccg gcaacaatta atagactgga tggaggcgga taaagttgca   5640

ggaccacttc tgcgctcggc ccttccggct ggctggttta ttgctgataa atctggagcc   5700

ggtgagcgtg ggtctcgcgg tatcattgca gcactggggc cagatggtaa gccctcccgt   5760

atcgtagtta tctacacgac ggggagtcag gcaactatgg atgaacgaaa tagacagatc   5820

gctgagatag gtgcctcact gattaagcat tggtaactgt cagaccaagt ttactcatat   5880

atactttaga ttgatttaaa acttcatttt taatttaaaa ggatctaggt gaagatcctt   5940

tttgataatc tcatgaccaa aatcccttaa cgtgagtttt cgttccactg agcgtcagac   6000

cccgtagaaa agatcaaagg atcttcttga gatccttttt ttctgcgcgt aatctgctgc   6060

ttgcaaacaa aaaaaccacc gctaccagcg gtggtttgtt tgccggatca agagctacca   6120

actctttttc cgaaggtaac tggcttcagc agagcgcaga taccaaatac tgtccttcta   6180

gtgtagccgt agttaggcca ccacttcaag aactctgtag caccgcctac atacctcgct   6240

ctgctaatcc tgttaccagt ggctgctgcc agtggcgata agtcgtgtct taccgggttg   6300

gactcaagac gatagttacc ggataaggcg cagcggtcgg gctgaacggg gggttcgtgc   6360

acacagccca gcttggagcg aacgacctac accgaactga gatacctaca gcgtgagcta   6420

tgagaaagcg ccacgcttcc cgaagggaga aaggcggaca ggtatccggt aagcggcagg   6480

gtcggaacag gagagcgcac gagggagctt ccagggggaa acgcctggta tctttatagt   6540

cctgtcgggt ttcgccacct ctgacttgag cgtcgatttt tgtgatgctc gtcagggggg   6600

cggagcctat ggaaaaacgc cagcaacgcg gcctttttac ggttcctggc cttttgctgg   6660

ccttttgctc acatgtggga ggctagagta catttaggtg acactataga a            6711
```

<210> SEQ ID NO 38
<211> LENGTH: 6711
<212> TYPE: DNA
<213> ORGANISM: Sindbis virus

<400> SEQUENCE: 38

```
attgacggcg tagtacacac tattgaatca aacagccgac caattgcact accatcacaa     60

tggagaagcc agtagtaaac gtagacgtag acccccagag tccgtttgtc gtgcaactgc    120

aaaaaagctt cccgcaattt gaggtagtag cacagcaggt cactccaaat gaccatgcta    180

atgccagagc attttcgcat ctggccagta aactaatcga gctggaggtt cctaccacag    240

cgacgatctt ggacataggc agcgcaccgg ctcgtagaat gttttccgag caccagtatc    300

attgtgtctg ccccatgcgt agtccagaag acccggaccg catgatgaaa tatgccagta    360
```

-continued

```
aactggcgga aaaagcgtgc aagattacaa acaagaactt gcatgagaag attaaggatc    420
tccggatccc ctgaaaaggc tgtttaagtt gggtaaaccg ctcccagccg acgacgagca    480
agacgaagac agaagacgcg ctctgctaga tgaaacaaag gcgtggttta gagtaggtat    540
aacaggcact ttagcagtgg ccgtgacgac ccggtatgag gtagacaata ttacacctgt    600
cctactggca ttgagaactt ttgcccagag caaaagagca ttccaagcca tcagaggga    660
aataaagcat ctctacggtg gtcctaaata gtcagcatag tacatttcat ctgactaata    720
ctacaacacc accaccatga atagaggatt ctttaacatg ctcggccgcc gccccttccc    780
ggcccccact gccatgtgga ggccgcggag aaggaggcag gcggccccga tgcctgcccg    840
caacgggctg gcttctcaaa tccagcaact gaccacagcc gtcagtgccc tagtcattgg    900
acaggcaact agacctcaac ccccacgtcc acgccagcca ccgcgccaga agaagcaggc    960
gcccaagcaa ccaccgaagc cgaagaaacc aaaaacgcag gagaagaaga agaagcaacc   1020
tgcaaaaccc aaacccggaa agagacagcg catggcactt aagttggagg ccgacagatt   1080
gttcgacgtc aagaacgagg acggagatgt catcgggcac gcactggcca tggaaggaaa   1140
ggtaatgaaa cctctgcacg tgaaaggaac catcgaccac cctgtgctat caaagctcaa   1200
atttaccaag tcgtcagcat acgacatgga gttcgcacag ttgccagtca acatgagaag   1260
tgaggcattc acctacacca gtgaacaccc cgaaggattc tataactggc accacggagc   1320
ggtgcagtat agtggaggta gatttaccat ccctcgcgga gtaggaggca gaggagacag   1380
cggtcgtccg atcatggata actccggtcg ggttgtcgcg atagtcctcg gtggagctga   1440
tgaaggaaca cgaactgccc tttcggtcgt cacctggaat agtaaaggga agacaattaa   1500
gacgaccccg gaagggacag aagagtggtc cgcagcacca ctggtcacgg caatgtgttt   1560
gctcggaaat gtgagcttcc catgcgaccg cccgcccaca tgctataccc gcgaaccttc   1620
cagagccctc gacatccttg aagagaacgt gaaccatgag gcctacgata ccctgctcaa   1680
tgccatattg cggtgcggat cgtctggcag aagcaaaaga agcgtcactg acgactttac   1740
cctgaccagc ccctacttgg gcacatgctc gtactgccac catactgaac cgtgcttcag   1800
ccctgttaag atcgagcagg tctgggacga agcggacgat aacaccatac gcatacagac   1860
ttccgcccag tttggatacg accaaagcgg agcagcaagc gcaaacaagt accgctacat   1920
gtcgcttaag caggatcaca ccgttaaaga aggcaccatg gatgacatca agattagcac   1980
ctcaggaccg tgtagaaggc ttagctacaa aggatacttt ctcctcgcaa aatgccctcc   2040
aggggacagc gtaacggtta gcatagtgag tagcaactca gcaacgtcat gtacactggc   2100
ccgcaagata aaaccaaaat tcgtgggacg ggaaaaatat gatctacctc ccgttcacgg   2160
taaaaaaatt ccttgcacag tgtacgaccg tctgaaagaa acaactgcag gctacatcac   2220
tatgcacagg ccgggaccgc acgcttatac atcctacctg aaagaatcat cagggaaagt   2280
ttacgcaaag ccgccatctg ggaagaacat tacgtatgag tgcaagtgcg gcgactacaa   2340
gaccggaacc gtttcgaccc gcaccgaaat cactggttgc accgccatca agcagtgcgt   2400
cgcctataag agcgaccaaa cgaagtgggt cttcaactca ccggacttga tcagacatga   2460
cgaccacacg gcccaaggga aattgcattt gcctttcaag ttgatcccga gtacctgcat   2520
ggtccctgtt gcccacgcgc cgaatgtaat acatggcttt aaacacatca gcctccaatt   2580
agatacagac cacttgacat tgctcaccac caggagacta ggggcaaacc cggaaccaac   2640
cactgaatgg atcgtcggaa agacggtcag aaacttcacc gtcgaccgag atggcctgga   2700
```

-continued

```
atacatatgg ggaaatcatg agccagtgag ggtctatgcc caagagtcag caccaggaga   2760
ccctcacgga tggccacacg aaatagtaca gcattactac catcgccatc ctgtgtacac   2820
catcttagcc gtcgcatcag ctaccgtggc gatgatgatt ggcgtaactg ttgcagtgtt   2880
atgtgcctgt aaagcgcgcc gtgagtgcct gacgccatac gccctggccc caaacgccgt   2940
aatcccaact tcgctggcac tcttgtgctg cgttaggtcg gccaatgctg aaacgttcac   3000
cgagaccatg agttacttgt ggtcgaacag tcagccgttc ttctgggtcc agttgtgcat   3060
acctttggcc gctttcatcg ttctaatgcg ctgctgctcc tgctgcctgc ctttttttagt   3120
ggttgccggc gcctacctgg cgaaggtaga cgcctacgaa catgcgacca ctgttccaaa   3180
tgtgccacag ataccgtata aggcacttgt tgaaagggca gggtatgccc cgctcaattt   3240
ggagatcact gtcatgtcct cggaggtttt gccttccacc aaccaagagt acattacctg   3300
caaattcacc actgtggtcc cctccccaaa aatcaaatgc tgcggctcct tggaatgtca   3360
gccggccgtt catgcagact atacctgcaa ggtcttcgga ggggtctacc cctttatgtg   3420
gggaggagcg caatgttttt gcgacagtga gaacagccag atgagtgagg cgtacgtcga   3480
actgtcagca gattgcgcgt ctgaccacgc gcaggcgatt aaggtgcaca ctgccgcgat   3540
gaaagtagga ctgcgtatag tgtacgggaa cactaccagt ttcctagatg tgtacgtgaa   3600
cggagtcaca ccaggaacgt ctaaagactt gaaagtcata gctggaccaa tttcagcatc   3660
gtttacgcca ttcgatcata aggtcgttat ccatcgcggc ctggtgtaca actatgactt   3720
cccggaatat ggagcgatga aaccaggagc gtttggagac attcaagcta cctccttgac   3780
tagcaaggat ctcatcgcca gcacagacat taggctactc aagccttccg ccaagaacgt   3840
gcatgtcccg tacacgcagg ccgcatcagg atttgagatg tggaaaaaca actcaggccg   3900
cccactgcag gaaaccgcac ctttcgggtg taagattgca gtaaatccgc tccgagcggt   3960
ggactgttca tacgggaaca ttcccatttc tattgacatc ccgaacgctg cctttatcag   4020
gacatcagat gcaccactgg tctcaacagt caaatgtgaa gtcagtgagt gcacttattc   4080
agcagacttc ggcgggatgg ccaccctgca gtatgtatcc gaccgcgaag gtcaatgccc   4140
cgtacattcg cattcgagca cagcaactct ccaagagtcg acagtacatg tcctggagaa   4200
aggagcggtg acagtacact ttagcaccgc gagtccacag gcgaacttta tcgtatcgct   4260
gtgtgggaag aagacaacat gcaatgcaga atgtaaacca ccagctgacc atatcgtgag   4320
caccccgcac aaaaatgacc aagaatttca agccgccatc tcaaaaacat catggagttg   4380
gctgtttgcc cttttcggcg gcgcctcgtc gctattaatt ataggactta tgatttttgc   4440
ttgcagcatg atgctgacta gcacacgaag atgaccgcta cgccccaatg atccgaccag   4500
caaaactcga tgtacttccg aggaactgat gtgcataatg catcaggctg gtacattaga   4560
tccccgctta ccgcgggcaa tatagcaaca ctaaaaactc gatgtacttc cgaggaagcg   4620
cagtgcataa tgctgcgcag tgttgccaca taaccactat attaaccatt tatctagcgg   4680
acgccaaaaa ctcaatgtat ttctgaggaa gcgtggtgca taatgccacg cagcgtctgc   4740
ataactttta ttatttcttt tattaatcaa caaaattttg tttttaacat ttcaaaaaaa   4800
aaaaaaaaaa aaaaaaaaaa aaaaaaaaaa atttaaatta attaagcggc cgcctcgagg   4860
acgtcaggtg gcacttttcg gggaaatgtg cgcggaaccc ctatttgttt atttttctaa   4920
atacattcaa atatgtatcc gctcatgaga caataaccct gataaatgct tcaataatat   4980
tgaaaaagga agagtatgag tattcaacat ttccgtgtcg cccttattcc cttttttgcg   5040
gcattttgcc ttcctgtttt tgctcaccca gaaacgctgg tgaaagtaaa agatgctgaa   5100
```

-continued

```
gatcagttgg gtgcacgagt gggttacatc gaactggatc tcaacagcgg taagatcctt   5160
gagagttttc gccccgaaga acgttttcca atgatgagca cttttaaagt tctgctatgt   5220
ggcgcggtat tatcccgtat tgacgccggg caagagcaac tcggtcgccg catacactat   5280
tctcagaatg acttggttga gtactcacca gtcacagaaa agcatcttac ggatggcatg   5340
acagtaagag aattatgcag tgctgccata accatgagtg ataacactgc ggccaactta   5400
cttctgacaa cgatcggagg accgaaggag ctaaccgctt ttttgcacaa catgggggat   5460
catgtaactc gccttgatcg ttgggaaccg gagctgaatg aagccatacc aaacgacgag   5520
cgtgacacca cgatgcctgt agcaatggca acaacgttgc gcaaactatt aactggcgaa   5580
ctacttactc tagcttcccg gcaacaatta atagactgga tggaggcgga taaagttgca   5640
ggaccacttc tgcgctcggc ccttccggct ggctggttta ttgctgataa atctggagcc   5700
ggtgagcgtg ggtctcgcgg tatcattgca gcactggggc cagatggtaa gccctcccgt   5760
atcgtagtta tctacacgac ggggagtcag gcaactatgg atgaacgaaa tagacagatc   5820
gctgagatag gtgcctcact gattaagcat tggtaactgt cagaccaagt ttactcatat   5880
atactttaga ttgatttaaa acttcatttt taatttaaaa ggatctaggt gaagatcctt   5940
tttgataatc tcatgaccaa aatcccttaa cgtgagtttt cgttccactg agcgtcagac   6000
cccgtagaaa agatcaaagg atcttcttga gatccttttt ttctgcgcgt aatctgctgc   6060
ttgcaaacaa aaaaaccacc gctaccagcg gtggtttgtt tgccggatca agagctacca   6120
actctttttc cgaaggtaac tggcttcagc agagcgcaga taccaaatac tgtccttcta   6180
gtgtagccgt agttaggcca ccacttcaag aactctgtag caccgcctac atacctcgct   6240
ctgctaatcc tgttaccagt ggctgctgcc agtggcgata agtcgtgtct taccgggttg   6300
gactcaagac gatagttacc ggataaggcg cagcggtcgg gctgaacggg gggttcgtgc   6360
acacagccca gcttggagcg aacgacctac accgaactga gatacctaca gcgtgagcta   6420
tgagaaagcg ccacgcttcc cgaagggaga aaggcggaca ggtatccggt aagcggcagg   6480
gtcggaacag gagagcgcac gagggagctt ccagggggaa acgcctggta tctttatagt   6540
cctgtcgggt ttcgccacct ctgacttgag cgtcgatttt tgtgatgctc gtcagggggg   6600
cggagcctat ggaaaaacgc cagcaacgcg gcctttttac ggttcctggc cttttgctgg   6660
ccttttgctc acatgtggga ggctagagta catttaggtg acactataga a            6711
```

<210> SEQ ID NO 39
<211> LENGTH: 6711
<212> TYPE: DNA
<213> ORGANISM: Sindbis virus

<400> SEQUENCE: 39

```
attgacggcg tagtacacac tattgaatca aacagccgac caattgcact accatcacaa     60
tggagaagcc agtagtaaac gtagacgtag acccccagag tccgtttgtc gtgcaactgc    120
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tatgccagta    360
aactggcgga aaaagcgtgc aagattacaa acaagaactt gcatgagaag attaaggatc    420
tccggatccc ctgaaaaggc tgtttaagtt gggtaaaccg ctcccagccg acgacgagca    480
```

-continued

```
agacgaagac agaagacgcg ctctgctaga tgaaacaaag gcgtggttta gagtaggtat    540
aacaggcact ttagcagtgg ccgtgacgac ccggtatgag gtagacaata ttacacctgt    600
cctactggca ttgagaactt ttgcccagag caaaagagca ttccaagcca tcagagggga    660
aataaagcat ctctacggtg gtcctaaata gtcagcatag tacatttcat ctgactaata    720
ctacaacacc accaccatga atagaggatt ctttaacatg ctcggccgcc gccccttccc    780
ggcccccact gccatgtgga ggccgcggag aaggaggcag gcggccccga tgcctgcccg    840
caacgggctg gcttctcaaa tccagcaact gaccacagcc gtcagtgccc tagtcattgg    900
acaggcaact agacctcaac ccccacgtcc acgccagcca ccgcgccaga agaagcaggc    960
gcccaagcaa ccaccgaagc cgaagaaacc aaaaacgcag gagaagaaga agaagcaacc   1020
tgcaaaaccc aaacccggaa agagacagcg catggcactt aagttggagg ccgacagatt   1080
gttcgacgtc aagaacgagg acggagatgt catcgggcac gcactggcca tggaaggaaa   1140
ggtaatgaaa cctctgcacg tgaaaggaac catcgaccac cctgtgctat caaagctcaa   1200
atttaccaag tcgtcagcat acgacatgga gttcgcacag ttgccagtca acatgagaag   1260
tgaggcattc acctacacca gtgaacaccc cgaaggattc tataactggc accacggagc   1320
ggtgcagtat agtggaggta gatttaccat ccctcgcgga gtaggaggca gaggagacag   1380
cggtcgtccg atcatggata actccggtcg ggttgtcgcg atagtcctcg gtggagctga   1440
tgaaggaaca cgaactgccc tttcggtcgt cacctggaat agtaaaggga agacaattaa   1500
gacgaccccg gaagggacag aagagtggtc cgcagcacca ctggtcacgg caatgtgttt   1560
gctcggaaat gtgagcttcc catgcgaccg cccgcccaca tgctataccc gcgaaccttc   1620
cagagccctc gacatccttg aagagaacgt gaaccatgag gcctacgata ccctgctcaa   1680
tgccatattg cggtgcggat cgtctggcag aagcaaaaga agcgtcatcg atgactttac   1740
cctgaccagc ccctacttgg gcacatgctc gtactgccac catactgaac cgtgcttcag   1800
ccctgttaag atcgagcagg tctgggacga agcggacgat aacaccatac gcatacagac   1860
ttccgcccag tttggatacg accaaagcgg agcagcaagc gcaaacaagt accgctacat   1920
gtcgcttaag caggatcaca ccgttaaaga aggcaccatg gatgacatca agattagcac   1980
ctcaggaccg tgtagaaggc ttagctacaa aggatacttt ctcctcgcaa aatgccctcc   2040
aggggacagc gtaacggtta gcatagtgag tagcaactca gcaacgtcat gtacactggc   2100
ccgcaagata aaaccaaaat tcgtgggacg ggaaaaatat gatctacctc ccgttcacgg   2160
taaaaaaatt ccttgcacag tgtacgaccg tctgaaagaa acaactgcag gctacatcac   2220
tatgcacagg ccgggcccgc acgcttatac atcctacctg gaagaatcat cagggaaagt   2280
ttacgcaaag ccgccatctg ggaagaacat tacgtatgag tgcaagtgcg gcgactacaa   2340
gaccggaacc gtttcgaccc gcaccgaaat cactggttgc accgccatca agcagtgcgt   2400
cgcctataag agcgaccaaa cgaagtgggt cttcaactca ccggacttga tccgacatga   2460
cgaccacacg gtccaaggga aattgcattt gcctttcaag ttgatcccga gtacctgcat   2520
ggtccctgtt gcccacgcgc cgaatgtaat acatggcttt aaacacatca gcctccaatt   2580
agatacagac cacttgacat tgctcaccac caggagacta ggggcaaacc cggaaccaac   2640
cactgaatgg atcgtcggaa agacggtcag aaacttcacc gtcgaccgag atggcctgga   2700
atacatatgg ggaaatcatg agccagtgag ggtctatgcc caagagtcag caccaggaga   2760
ccctcacgga tggccacacg aaatagtaca gcattactac catcgccatc ctgtgtacac   2820
catcttagcc gtcgcatcag ctaccgtggc gatgatgatt ggcgtaactg ttgcagtgtt   2880
```

-continued

```
atgtgcctgt aaagcgcgcc gtgagtgcct gacgccatac gccctggccc caaacgccgt   2940
aatcccaact tcgctggcac tcttgtgctg cgttaggtcg gccaatgctg aaacgttcac   3000
cgagaccatg agttacttgt ggtcgaacag tcagccgttc ttctgggtcc agttgtgcat   3060
acctttggcc gctttcatcg ttctaatgcg ctgctgctcc tgctgcctgc ctttttttagt  3120
ggttgccggc gcctacctgg cgaaggtaga cgcctacgaa catgcgacca ctgttccaaa   3180
tgtgccacag ataccgtata aggcacttgt tgaaagggca gggtatgccc cgctcaattt   3240
ggagatcact gtcatgtcct cggaggtttt gccttccacc aaccaagagt acattacctg   3300
caaattcacc actgtggtcc cctccccaaa aatcaaatgc tgcggctcct tggaatgtca   3360
gccggccgtt catgcagact atacctgcaa ggtcttcgga ggggtctacc cctttatgtg   3420
gggaggagcg caatgttttt gcgacagtga gaacagccag atgagtgagg cgtacgtcga   3480
actgtcagca gattgcgcgt ctgaccacgc gcaggcgatt aaggtgcaca ctgccgcgat   3540
gaaagtagga ctgcgtatag tgtacgggaa cactaccagt ttcctagatg tgtacgtgaa   3600
cggagtcaca ccaggaacgt ctaaagactt gaaagtcata gctggaccaa tttcagcatc   3660
gtttacgcca ttcgatcata aggtcgttat ccatcgcggc ctggtgtaca actatgactt   3720
cccggaatat ggagcgatga aaccaggagc gtttggagac attcaagcta cctccttgac   3780
tagcaaggat ctcatcgcca gcacagacat taggctactc aagccttccg ccaagaacgt   3840
gcatgtcccg tacacgcagg ccgcatcagg atttgagatg tggaaaaaca actcaggccg   3900
cccactgcag gaaaccgcac ctttcgggtg taagattgca gtaaatccgc tccgagcggt   3960
ggactgttca tacgggaaca ttcccatttc tattgacatc ccgaacgctg cctttatcag   4020
gacatcagat gcaccactgg tctcaacagt caaatgtgaa gtcagtgagt gcacttattc   4080
agcagacttc ggcgggatgg ccaccctgca gtatgtatcc gaccgcgaag gtcaatgccc   4140
cgtacattcg cattcgagca cagcaactct ccaagagtcg acagtacatg tcctggagaa   4200
aggagcggtg acagtacact ttagcaccgc gagtccacag gcgaacttta tcgtatcgct   4260
gtgtgggaag aagacaacat gcaatgcaga atgtaaacca ccagctgacc atatcgtgag   4320
caccccgcac aaaaatgacc aagaatttca agccgccatc tcaaaaacat catggagttg   4380
gctgtttgcc cttttcggcg gcgcctcgtc gctattaatt ataggactta tgatttttgc   4440
ttgcagcatg atgctgacta gcacacgaag atgaccgcta cgccccaatg atccgaccag   4500
caaaactcga tgtacttccg aggaactgat gtgcataatg catcaggctg gtacattaga   4560
tccccgctta ccgcgggcaa tatagcaaca ctaaaaactc gatgtacttc cgaggaagcg   4620
cagtgcataa tgctgcgcag tgttgccaca taaccactat attaaccatt tatctagcgg   4680
acgccaaaaa ctcaatgtat ttctgaggaa gcgtggtgca taatgccacg cagcgtctgc   4740
ataactttta ttatttcttt tattaatcaa caaaattttg tttttaacat ttcaaaaaaa   4800
aaaaaaaaaa aaaaaaaaaa aaaaaaaaaa atttaaatta attaagcggc cgcctcgagg   4860
acgtcaggtg gcacttttcg gggaaatgtg cgcggaaccc ctatttgttt atttttctaa   4920
atacattcaa atatgtatcc gctcatgaga caataaccct gataaatgct tcaataatat   4980
tgaaaaagga agagtatgag tattcaacat ttccgtgtcg cccttattcc cttttttgcg   5040
gcattttgcc ttcctgtttt tgctcaccca gaaacgctgg tgaaagtaaa agatgctgaa   5100
gatcagttgg gtgcacgagt gggttacatc gaactggatc tcaacagcgg taagatcctt   5160
gagagttttc gccccgaaga acgttttcca atgatgagca cttttaaagt tctgctatgt   5220
```

-continued

```
ggcgcggtat tatcccgtat tgacgccggg caagagcaac tcggtcgccg catacactat   5280
tctcagaatg acttggttga gtactcacca gtcacagaaa agcatcttac ggatggcatg   5340
acagtaagag aattatgcag tgctgccata accatgagtg ataacactgc ggccaactta   5400
cttctgacaa cgatcggagg accgaaggag ctaaccgctt ttttgcacaa catgggggat   5460
catgtaactc gccttgatcg ttgggaaccg gagctgaatg aagccatacc aaacgacgag   5520
cgtgacacca cgatgcctgt agcaatggca acaacgttgc gcaaactatt aactggcgaa   5580
ctacttactc tagcttcccg gcaacaatta atagactgga tggaggcgga taaagttgca   5640
ggaccacttc tgcgctcggc ccttccggct ggctggttta ttgctgataa atctggagcc   5700
ggtgagcgtg ggtctcgcgg tatcattgca gcactggggc cagatggtaa gccctcccgt   5760
atcgtagtta tctacacgac ggggagtcag gcaactatgg atgaacgaaa tagacagatc   5820
gctgagatag gtgcctcact gattaagcat tggtaactgt cagaccaagt ttactcatat   5880
atactttaga ttgatttaaa acttcatttt taatttaaaa ggatctaggt gaagatcctt   5940
tttgataatc tcatgaccaa aatcccttaa cgtgagtttt cgttccactg agcgtcagac   6000
cccgtagaaa agatcaaagg atcttcttga gatccttttt ttctgcgcgt aatctgctgc   6060
ttgcaaacaa aaaaaccacc gctaccagcg gtggtttgtt tgccggatca agagctacca   6120
actctttttc cgaaggtaac tggcttcagc agagcgcaga taccaaatac tgtccttcta   6180
gtgtagccgt agttaggcca ccacttcaag aactctgtag caccgcctac atacctcgct   6240
ctgctaatcc tgttaccagt ggctgctgcc agtggcgata agtcgtgtct taccgggttg   6300
gactcaagac gatagttacc ggataaggcg cagcggtcgg gctgaacggg gggttcgtgc   6360
acacagccca gcttggagcg aacgacctac accgaactga gatacctaca gcgtgagcta   6420
tgagaaagcg ccacgcttcc cgaagggaga aaggcggaca ggtatccggt aagcggcagg   6480
gtcggaacag gagagcgcac gagggagctt ccagggggaa acgcctggta tctttatagt   6540
cctgtcgggt ttcgccacct ctgacttgag cgtcgatttt tgtgatgctc gtcagggggg   6600
cggagcctat ggaaaaacgc cagcaacgcg gcctttttac ggttcctggc cttttgctgg   6660
ccttttgctc acatgtggga ggctagagta catttaggtg acactataga a            6711
```

<210> SEQ ID NO 40
<211> LENGTH: 6711
<212> TYPE: DNA
<213> ORGANISM: Sindbis virus

<400> SEQUENCE: 40

```
attgacggcg tagtacacac tattgaatca aacagccgac caattgcact accatcacaa     60
tggagaagcc agtagtaaac gtagacgtag acccccagag tccgtttgtc gtgcaactgc    120
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggaccg catgatgaaa tatgccagta    360
aactggcgga aaaagcgtgc aagattacaa acaagaactt gcatgagaag attaaggatc    420
tccggatccc ctgaaaaggc tgtttaagtt gggtaaaccg ctcccagccg acgacgagca    480
agacgaagac agaagacgcg ctctgctaga tgaaacaaag gcgtggttta gagtaggtat    540
aacaggcact ttagcagtgg ccgtgacgac ccggtatgag gtagacaata ttacacctgt    600
cctactggca ttgagaactt ttgcccagag caaaagagca ttccaagcca tcagagggga    660
```

-continued

```
aataaagcat ctctacggtg gtcctaaata gtcagcatag tacatttcat ctgactaata    720
ctacaacacc accaccatga atagaggatt ctttaacatg ctcggccgcc gcccccttccc   780
ggcccccact gccatgtgga ggccgcggag aaggaggcag gcggccccga tgcctgcccg    840
caacgggctg gcttctcaaa tccagcaact gaccacagcc gtcagtgccc tagtcattgg    900
acaggcaact agacctcaac ccccacgtcc acgccagcca ccgcgccaga agaagcaggc    960
gcccaagcaa ccaccgaagc cgaagaaacc aaaaacgcag gagaagaaga agaagcaacc   1020
tgcaaaaccc aaacccggaa agagacagcg catggcactt aagttggagg ccgacagatt   1080
gttcgacgtc aagaacgagg acggagatgt catcgggcac gcactggcca tggaaggaaa   1140
ggtaatgaaa cctctgcacg tgaaaggaac catcgaccac cctgtgctat caaagctcaa   1200
atttaccaag tcgtcagcat acgacatgga gttcgcacag ttgccagtca acatgagaag   1260
tgaggcattc acctacacca gtgaacaccc cgaaggattc tataactggc accacggagc   1320
ggtgcagtat agtggaggta gatttaccat ccctcgcgga gtaggaggca gaggagacag   1380
cggtcgtccg atcatggata actccggtcg ggttgtcgcg atagtcctcg gtggagctga   1440
tgaaggaaca cgaactgccc tttcggtcgt cacctggaat agtaaaggga agacaattaa   1500
gacgaccccg gaagggacag aagagtggtc cgcagcacca ctggtcacgg caatgtgttt   1560
gctcggaaat gtgagcttcc catgcgaccg cccgcccaca tgctataccc gcgaaccttc   1620
cagagccctc gacatccttg aagagaacgt gaaccatgag gcctacgata ccctgctcaa   1680
tgccatattg cggtgcggat cgtctggcag aagcaaaaga agcgtcactg acgactttac   1740
cctgaccagc ccctacttgg gcacatgctc gtactgccac catactgaac cgtgcttcag   1800
ccctgttaag atcgagcagg tctgggacga agcggacgat aacaccatac gcatacagac   1860
ttccgcccag tttggatacg accaaagcgg agcagcaagc gcaaacaagt accgctacat   1920
gtcgcttaag caggatcaca ccgttaaaga aggcaccatg gatgacatca agattagcac   1980
ctcaggaccg tgtagaaggc ttagctacaa aggatacttt ctcctcgcaa aatgccctcc   2040
aggggacagc gtaacggtta gcatagtgag tagcaactca gcaacgtcat gtacactggc   2100
ccgcaagata aaaccaaaat tcgtgggacg ggaaaaatat gatctacctc ccgttcacgg   2160
taaaaaaatt ccttgcacag tgtacgaccg tctgaaagaa acaactgcag gctacatcac   2220
tatgcacagg ccgggaccgc acgcttatac atcctacctg aaagaatcat cagggaaagt   2280
ttacgcaaag ccgccatctg ggaagaacat tacgtatgag tgcaagtgcg gcgactacaa   2340
gaccggaacc gtttcgaccc gcaccgaaat cactggttgc accgccatca agcagtgcgt   2400
cgcctataag agcgaccaaa cgaagtgggt cttcaactca ccggacttga tccgacatga   2460
cgaccacacg gtccaaggga aattgcattt gcctttcaag ttgatcccga gtacctgcat   2520
ggtccctgtt gcccacgcgc cgaatgtaat acatggcttt aaacacatca gcctccaatt   2580
agatacagac cacttgacat tgctcaccac caggagacta ggggcaaacc cggaaccaac   2640
cactgaatgg atcgtcggaa agacggtcag aaacttcacc gtcgaccgag atggcctgga   2700
atacatatgg ggaaatcatg agccagtgag ggtctatgcc caagagtcag caccaggaga   2760
ccctcacgga tggccacacg aaatagtaca gcattactac catcgccatc ctgtgtacac   2820
catcttagcc gtcgcatcag ctaccgtggc gatgatgatt ggcgtaactg ttgcagtgtt   2880
atgtgcctgt aaagcgcgcc gtgagtgcct gacgccatac gccctggccc caaacgccgt   2940
aatcccaact tcgctggcac tcttgtgctg cgttaggtcg gccaatgctg aaacgttcac   3000
```

-continued

```
cgagaccatg agttacttgt ggtcgaacag tcagccgttc ttctgggtcc agttgtgcat   3060
acctttggcc gctttcatcg ttctaatgcg ctgctgctcc tgctgcctgc ctttttttagt   3120
ggttgccggc gcctacctgg cgaaggtaga cgcctacgaa catgcgacca ctgttccaaa   3180
tgtgccacag ataccgtata aggcacttgt tgaaagggca gggtatgccc cgctcaattt   3240
ggagatcact gtcatgtcct cggaggtttt gccttccacc aaccaagagt acattacctg   3300
caaattcacc actgtggtcc cctccccaaa aatcaaatgc tgcggctcct tggaatgtca   3360
gccggccgtt catgcagact atacctgcaa ggtcttcgga ggggtctacc cctttatgtg   3420
gggaggagcg caatgttttt gcgacagtga gaacagccag atgagtgagg cgtacgtcga   3480
actgtcagca gattgcgcgt ctgaccacgc gcaggcgatt aaggtgcaca ctgccgcgat   3540
gaaagtagga ctgcgtatag tgtacgggaa cactaccagt ttcctagatg tgtacgtgaa   3600
cggagtcaca ccaggaacgt ctaaagactt gaaagtcata gctggaccaa tttcagcatc   3660
gtttacgcca ttcgatcata aggtcgttat ccatcgcggc ctggtgtaca actatgactt   3720
cccggaatat ggagcgatga aaccaggagc gtttggagac attcaagcta cctccttgac   3780
tagcaaggat ctcatcgcca gcacagacat taggctactc aagccttccg ccaagaacgt   3840
gcatgtcccg tacacgcagg ccgcatcagg atttgagatg tggaaaaaca actcaggccg   3900
cccactgcag gaaaccgcac ctttcgggtg taagattgca gtaaatccgc tccgagcggt   3960
ggactgttca tacgggaaca ttcccatttc tattgacatc ccgaacgctg cctttatcag   4020
gacatcagat gcaccactgg tctcaacagt caaatgtgaa gtcagtgagt gcacttattc   4080
agcagacttc ggcgggatgg ccaccctgca gtatgtatcc gaccgcgaag gtcaatgccc   4140
cgtacattcg cattcgagca cagcaactct ccaagagtcg acagtacatg tcctggagaa   4200
aggagcggtg acagtacact ttagcaccgc gagtccacag gcgaacttta tcgtatcgct   4260
gtgtgggaag aagacaacat gcaatgcaga atgtaaacca ccagctgacc atatcgtgag   4320
cacccgcac aaaaatgacc aagaatttca agccgccatc tcaaaaacat catggagttg   4380
gctgtttgcc cttttcggcg gcgcctcgtc gctattaatt ataggactta tgatttttgc   4440
ttgcagcatg atgctgacta gcacacgaag atgaccgcta cgccccaatg atccgaccag   4500
caaaactcga tgtacttccg aggaactgat gtgcataatg catcaggctg gtacattaga   4560
tccccgctta ccgcgggcaa tatagcaaca ctaaaaactc gatgtacttc cgaggaagcg   4620
cagtgcataa tgctgcgcag tgttgccaca taaccactat attaaccatt tatctagcgg   4680
acgccaaaaa ctcaatgtat ttctgaggaa gcgtggtgca taatgccacg cagcgtctgc   4740
ataactttta ttatttcttt tattaatcaa caaaattttg tttttaacat ttcaaaaaaa   4800
aaaaaaaaaa aaaaaaaaaa aaaaaaaaaa atttaaatta attaagcggc cgcctcgagg   4860
acgtcaggtg gcacttttcg gggaaatgtg cgcggaaccc ctatttgttt atttttctaa   4920
atacattcaa atatgtatcc gctcatgaga caataaccct gataaatgct tcaataatat   4980
tgaaaaagga agagtatgag tattcaacat ttccgtgtcg cccttattcc ctttttttgcg   5040
gcattttgcc ttcctgtttt tgctcaccca gaaacgctgg tgaaagtaaa agatgctgaa   5100
gatcagttgg gtgcacgagt gggttacatc gaactggatc tcaacagcgg taagatcctt   5160
gagagttttc gccccgaaga acgttttcca atgatgagca cttttaaagt tctgctatgt   5220
ggcgcggtat tatcccgtat tgacgccggg caagagcaac tcggtcgccg catacactat   5280
tctcagaatg acttggttga gtactcacca gtcacagaaa agcatcttac ggatggcatg   5340
acagtaagag aattatgcag tgctgccata accatgagtg ataacactgc ggccaactta   5400
```

-continued

```
cttctgacaa cgatcggagg accgaaggag ctaaccgctt ttttgcacaa catgggggat   5460

catgtaactc gccttgatcg ttgggaaccg gagctgaatg aagccatacc aaacgacgag   5520

cgtgacacca cgatgcctgt agcaatggca acaacgttgc gcaaactatt aactggcgaa   5580

ctacttactc tagcttcccg gcaacaatta atagactgga tggaggcgga taaagttgca   5640

ggaccacttc tgcgctcggc ccttccggct ggctggttta ttgctgataa atctggagcc   5700

ggtgagcgtg ggtctcgcgg tatcattgca gcactggggc cagatggtaa gccctcccgt   5760

atcgtagtta tctacacgac ggggagtcag gcaactatgg atgaacgaaa tagacagatc   5820

gctgagatag gtgcctcact gattaagcat tggtaactgt cagaccaagt ttactcatat   5880

atactttaga ttgatttaaa acttcatttt taatttaaaa ggatctaggt gaagatcctt   5940

tttgataatc tcatgaccaa aatcccttaa cgtgagtttt cgttccactg agcgtcagac   6000

cccgtagaaa agatcaaagg atcttcttga gatccttttt ttctgcgcgt aatctgctgc   6060

ttgcaaacaa aaaaaccacc gctaccagcg gtggtttgtt tgccggatca agagctacca   6120

actctttttc cgaaggtaac tggcttcagc agagcgcaga taccaaatac tgtccttcta   6180

gtgtagccgt agttaggcca ccacttcaag aactctgtag caccgcctac atacctcgct   6240

ctgctaatcc tgttaccagt ggctgctgcc agtggcgata agtcgtgtct taccgggttg   6300

gactcaagac gatagttacc ggataaggcg cagcggtcgg gctgaacggg gggttcgtgc   6360

acacagccca gcttggagcg aacgacctac accgaactga gatacctaca gcgtgagcta   6420

tgagaaagcg ccacgcttcc cgaagggaga aaggcggaca ggtatccggt aagcggcagg   6480

gtcggaacag gagagcgcac gagggagctt ccagggggaa acgcctggta tctttatagt   6540

cctgtcgggt ttcgccacct ctgacttgag cgtcgatttt tgtgatgctc gtcagggggg   6600

cggagcctat ggaaaaacgc cagcaacgcg gcctttttac ggttcctggc cttttgctgg   6660

ccttttgctc acatgtggga ggctagagta catttaggtg acactataga a             6711
```

DEFECTIVE SINDBIS VIRAL VECTORS

CROSS-REFERENCE TO RELATED APPLICATIONS

This application claims priority under 35 U.S.C. § 119(e) from Provisional Patent Application Ser. Nos. 60/666,432 and 60/755,428 filed Mar. 29, 2005 and Dec. 30, 2005, respectively, which are incorporated by reference in their entirety.

STATEMENT REGARDING FEDERALLY SPONSORED RESEARCH OR DEVELOPMENT

The United States Government has certain rights to this invention by virtue of funding received from US Public Health Service grants CA22247 and CA68498 from the National Cancer Institute, National Institutes of Health, Department of Health and Human Services, and by U.S. Army grant 0C000111.

FIELD OF THE INVENTION

The present invention is directed to defective Sindbis viral vectors, plasmids used to produce such vectors, pharmaceutical formulations containing the vectors, and methods for their production and use to treat mammals suffering from tumors.

BACKGROUND OF THE INVENTION

Sindbis virus, a member of the alphavirus genus in the Togaviridae family, is a single-stranded, enveloped, positive-sense RNA virus (Strauss & Strauss, 1994). In nature, it is transmitted via mosquito bites to mammals. Thus, as Sindbis virus has evolved as a blood-borne vector, this hematogenous delivery property enables Sindbis vectors to reach tumor cells throughout the circulation (Tseng et al 2004a,b).

PCT/US02/09432 published as WO 02/076468 entitled TUMOR THERAPY WITH ALPHAVIRUS-BASED AND HIGH AFFINITY LAMININ RECEPTOR-TARGETED VECTORS discloses a method for treating solid tumors in mammals using Alphavirus vectors. The method comprised administering to a mammal harboring a tumor an amount of an Alphavirus vector effective to treat the tumor. The vector was said to have a preferential affinity for high affinity laminin receptors (HALR). Tumor cells were said to express greater levels of HALR compared to normal cells of the same lineage. The anti-tumor effect was said to be due to the fact that Sindbis virus infection induced apoptosis in infected cells.

PCT/US 2004/026671 for A METHOD FOR DETECTING CANCER CELLS AND MONITORING CANCER THERAPY discloses the use of Sindbis viral vectors to identify cancer cells in the body of a mammal and monitor anti-cancer therapy.

With the aim of broadening the knowledge of the way Sindbis vectors work for cancer gene therapy, two different kinds of Sindbis vectors, SP6-H/SP6-R, derived from wild type Ar-339, and JT-BB/JT-Rep derived from an Ar-339 laboratory adapted strain, Toto 1101 have been studied. Sindbis virus Ar-339 was first isolated in August 1952, from a pool of mosquitoes (*Culex pipiens* and *C. univittatus*) trapped in the Sindbis health district in Egypt (Hurlbut 1953; Taylor and Hurlbut 1953; Frothingham 1955; Taylor et al. 1955). Toto 1101 was made out of the heat resistant (HR) strain initially derived from AR-339 (Burge and Pfefferkom, 1966). The first studies done with JT vectors in animal models showed good targeting of tumor cells and significant reduction of metastatic implant size (Tseng et al. 2002). Further studies of these vectors in tumor-induced SCID mice were done using the new imaging technique of IVIS®, that allows in vivo detection of viral vector and tumor cells in the same animal. In tumor-induced SCID mice there was a good correlation between vectors and tumor cells (Tseng et al. 2004b). Although these positive results in vector targeting and in vivo growth reduction of tumors and mouse survival, which are very promising for gene therapy, survival of all mice in these tumor models has not yet been achieved.

Therefore, what is need in the art are improved Sindbis viral vectors for use as anti-tumor agents.

BRIEF SUMMARY OF THE INVENTION

Disclosed herein are new vectors made from wild type Ar-339 Sindbis virus, with differences in replicase and envelope proteins between JT vectors and consensus Sindbis virus sequences, and also between JT and Ar-339 vectors. The chimeras combining both strains were produced and studied in tumor-induced SCID mice by the IVIS® imaging technique. Surprisingly JT envelope proteins targeted tumors more effectively than Ar-339 while Ar-339 replicase showed increased efficiency in tumor reduction. To analyze which residues would be responsible for tumor targeting, mutants of Ar-339 E2 envelope protein were made and tested by IVIS® imaging in ES-2 induced and tumor free mouse models. The change of only one amino acid from Glu to Lys at position 70 of Ar-339 E2, suppressed the ability to target metastatic tumor implants in mice. Double E2 mutant Mut-2, with K70 and V251 did not revert the targeting. Only when the whole sequence of JT E2 was substituted in the Ar-339 helper was the ability of targeting metastatic tumor implants recovered, though with less intensity. Thus, residue 70 in the outer leaf of the E2 protein is essential for tumor specific targeting of Sindbis vectors.

In one aspect, the present invention provides a purified, isolated nucleic acid comprising a nucleotide sequence as set forth in SEQ ID NO: 37 (SP6-H).

In another aspect, the present invention provides a purified, isolated nucleic acid comprising a nucleotide sequence as set forth in SEQ ID NO. 38 (SP6-HK 70).

In another aspect, the present invention provides a purified, isolated nucleic acid comprising a nucleotide sequence as set forth in SEQ ID NO. 40 (SP6-HK70-V251).

In a further aspect, the present invention provides a purified, isolated nucleic acid comprising a nucleotide sequence as set forth in SEQ ID NO: 39 (SP6-H-I3-K70-E181-V251).

In yet a further aspect, the present invention provides a method for producing defective Sindbis viral vectors comprising the steps of (a) providing a linearized replicon plasmid comprising the nucleotide sequence as set forth in SEQ ID NO: 36 and a linearized Helper plasmid selected from SEQ ID NO: 37, SEQ ID NO: 38, SEQ ID NO: 40 and SEQ ID NO: 39;

(b) transcribing said replicon plasmid and one Helper plasmid to produce RNA;

(c) collecting the RNA transcribed in step (b) and transfecting cells with said RNA;

(d) incubating said transfected cells for a time and at a temperature effective for producing defective Sindbis viral vectors; and (e) collecting said defective Sindbis viral vectors from the medium of said transfected cells.

These and other aspects of the present invention will be apparent to those of ordinary skill in the art in light of the present specification, claims and figures.

Ar-339 11703 nt genomic RNA, is illustrated schematically in grey line, viral subgenomic promoter ($P_{SG}$) nt 7334 to 7646, is represented as grey solid box. The viral genome was cloned in 6 PCR overlapping fragments. The viral replicase (grey dotted line) and the subgenomic promoter were cloned in 4 PCR fragments: CDNA-1, CDNA-2, CDNA-3A and CDNA-3B. The Sindbis subgenomic promoter and structural proteins sequence (gray dashed line) were cloned in 2 PCR overlapping fragments CDNA-4 and CDNA-5. The position of restriction enzyme sites in the PCR fragments that were used for further cloning strategy are indicated.

Figure 2:
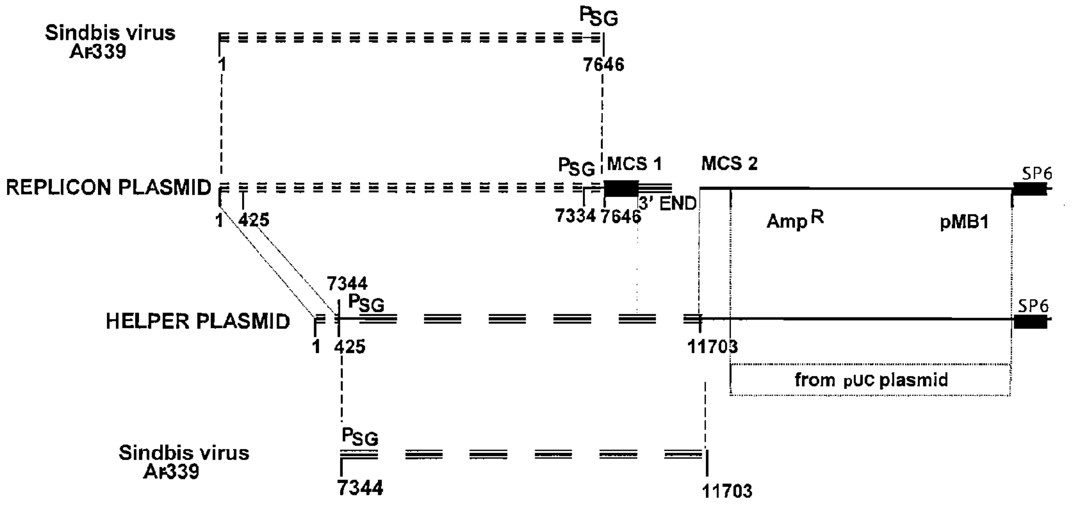

FIG. 2. Sindbis replicon and helper plasmids.

The Sindbis virus Ar-339 genome was split in two to generate both replicon and helper plasmids. Viral sequences are represented in grey. Virus nucleotide numbers are indicated and follow the Strauss et al. 1984 sequence.

Figure 3:
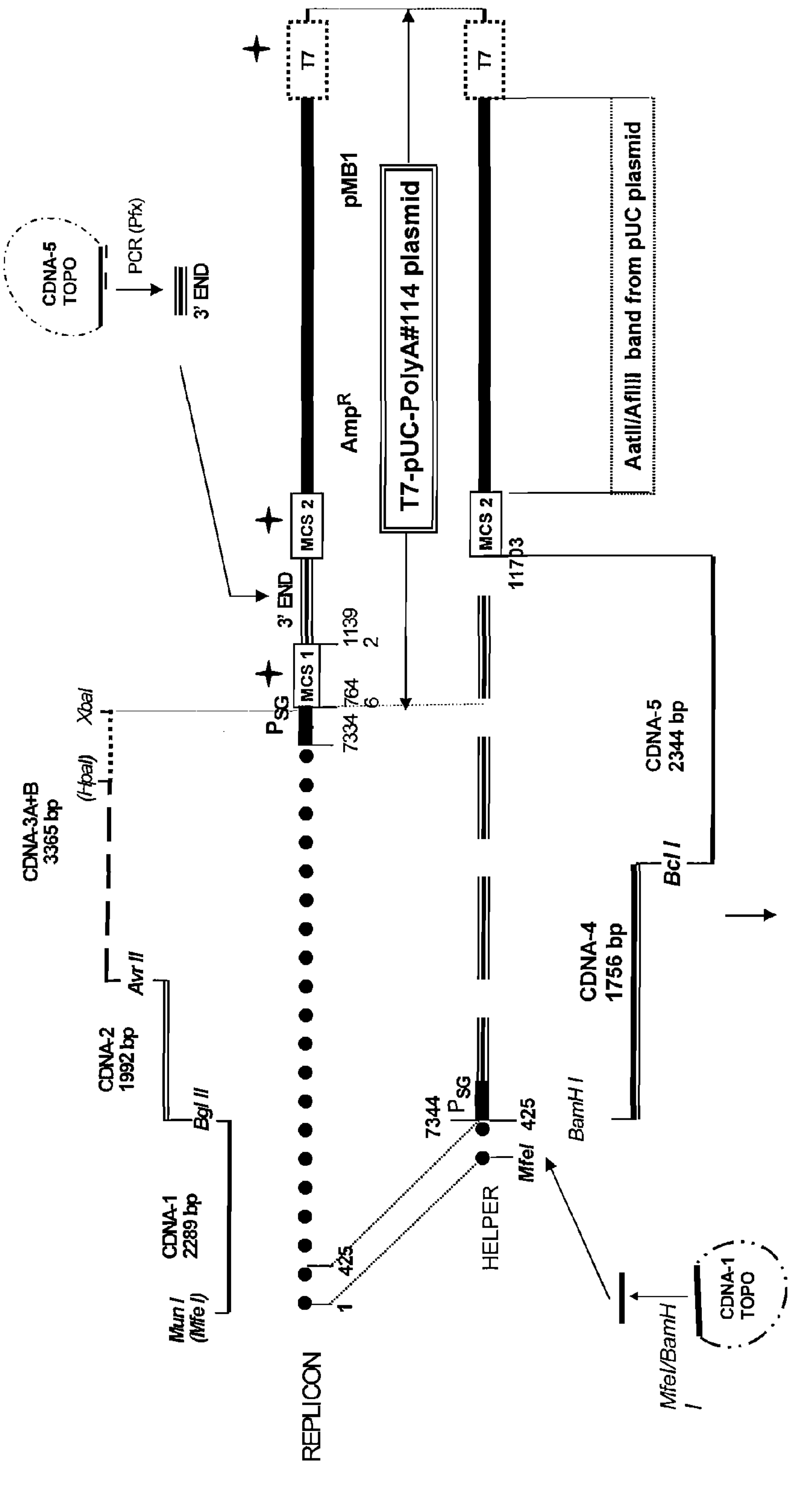

FIG. 3. Summary of vector constructions.

The first step generated the plasmid T7-pUC-PolyA#114 that contains the bacterial segment (ampicillin resistance, pMB1 replication origin), bacteriophage promoter T7, the two multicloning sites (MCS1 and MCS2) and the 3'end of the virus sequence (grey dashed line). To generate the replicon, restriction enzyme (RE) digested and gel purified DNA fragments from CDNA-1, CDNA-2 and CDNA-3 were cloned sequentially into T7-pUC-PolyA#114. To generate the helper, first the MfeI/BamHI fragment from the CDNA-1 plasmid was cloned into T7-pUC-PolyA#114, and bands from CDNA-4 and CDNA-5 were cloned into this plasmid. The sequences of the primers used to clone the Ar-339 cDNA fragments are shown in Table I (Appendix A).

Figure 4A:
Figure 4B:
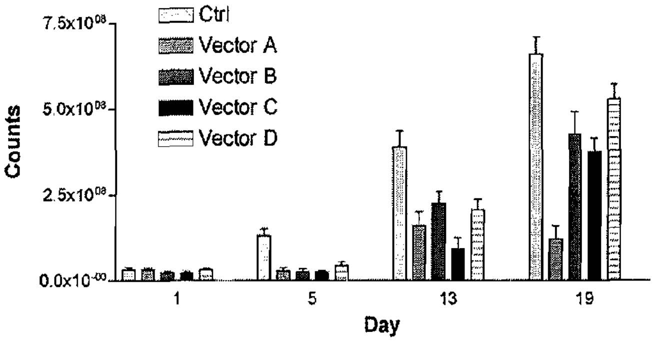

FIGS. 4(A and B). Suppression of disease progression by Ar-339 and JT chimeric vectors. A) ES-2/Fluc cells ($1.5\times10^6$) were i.p. inoculated into SCID mice on day 0. The next day (day 1), mice were imaged using the IVIS® Imaging System using D-luciferin as the substrate and were split into five groups of five mice each: control, which received no vector treatment, vector A (JT-BB/SP6-RhRLuc), vector B (SP6-H/JT-RephRluc), vector C (SP6-H/SP6-RhRluc) and vector D (JT-BB/JT-RephRluc). On day 5 the groups received daily i.p. treatments of corresponding Sindbis vectors and were IVIS® imaged on days 1, 5, 13 and 19. All vector treatments suppressed the tumor growth on the mesentery and diaphragm and reduced the signals on the omentum compared with control mice. B) Quantitative analysis of the whole-body total photon counts of control and Sindbis-treated mice. Error bars represent the SEM.

Figure 5:
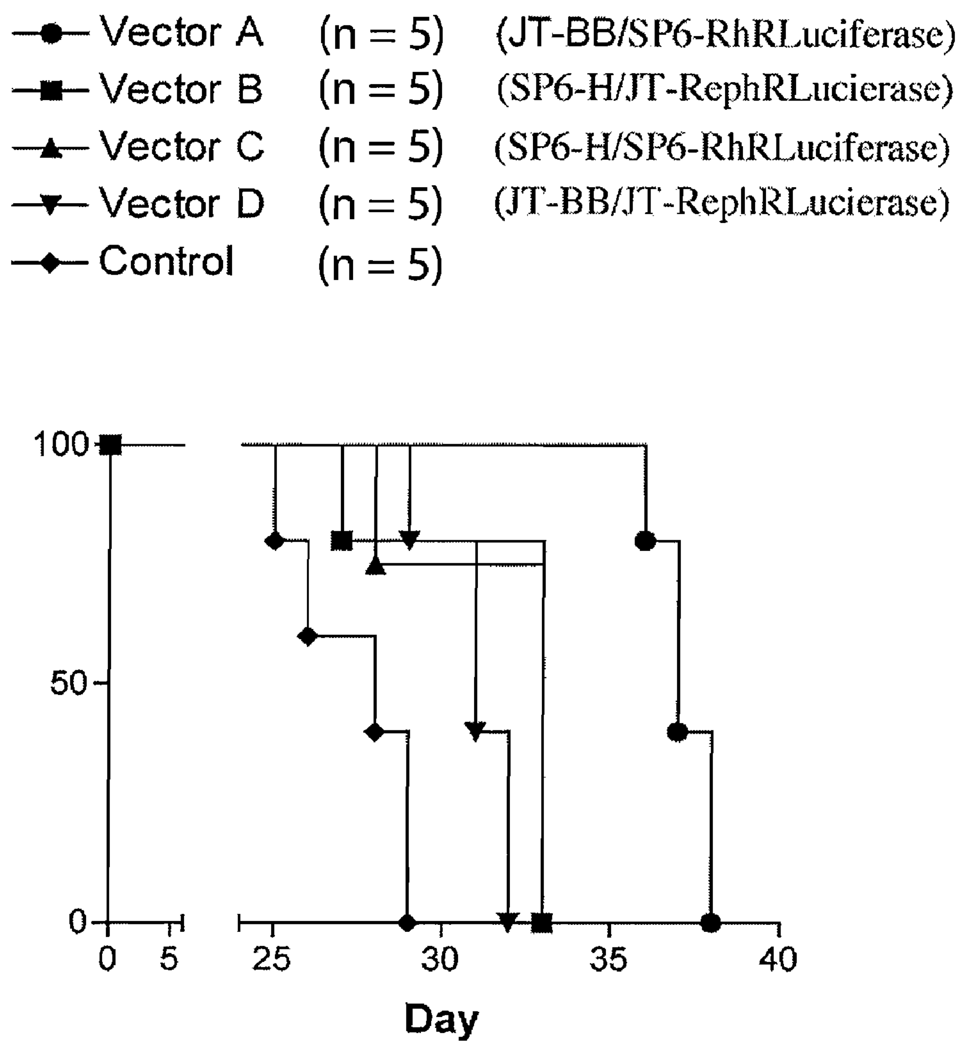

FIG. 5. Survival curves of mice treated with Ar-339 and JT vectors. Survival curve of mice described in FIG. 4. Vector A was the most efficient in prolonging the survival of mice bearing ES-2/Fluc tumors.

FIGS. 6(A and B). Colocalization in peritoneal cavity of vector C. A)Vector C (SP6-H/SP6-RhRluc) infection colocalized with the metastasized ES-2/Fluc tumors in the peritoneal cavity as determined by the IVIS® system. SCID mice were i.p. inoculated with $1.5\times10^6$ ES-2/Fluc cells. Five days later, while the disease was still microscopic, inoculated mice received a single i.p. treatment of Vector C and were imaged the next day. The first IVIS® imaging was done by i.p. injection of Rluc substrate, coelenterazine, followed by a 5-minute acquiring interval (left panel). Thirty minutes after the coelenterazine injection, when the short-lived Rluc signals faded away, Fluc substrate, D-luciferin, was i.p. injected to determine the ES-2/Fluc tumor locations (right panel). B) Correlation analysis of vector C shows a high correspondence between tumor cells and vector infection in the peritoneal cavity.

FIGS. 7(A and B). Background infection of Ar-339 and JT chimeric vectors. A) Five tumor-free mice per group were i.p. injected on day 0 with one dose of vector A (JT-BB/SP6-RFluc), vector B (SP6-H/JT-RepFluc) or vector C (SP6-H/SP6-RFluc) and next day (day 1) IVIS® imaged for vector luciferase signal). The peritoneum was removed for imaging of the peritoneal cavity and the organs were harvested and imaged for the representative mice (rows 3 to 5). All vectors showed infection in fat tissue, and in vector B and C groups some mice showed a low background signal on ribs but not in organs B) Some mice per group received a second i.p. injection of the vectors of day 2, and were IVIS® imaged in: the peritoneal cavities (second row) and organs (bottom rows) on day 3. Very low signals were observed in fat tissue for vectors B and C.

FIGS. (8A and B). Tumor targeting of Ar-339 and JT chimeric vectors. A) SCID female mice were injected i.p. on day 0 with $2\times10^6$ ES-2 cells/mouse. On day 4 five mice per group were i.p. injected with one doses of vector A (JT-BB/SP6-RFluc), vector B (SP6-H/JT-RepFluc) or vector C (SP6-H/SP6-RFluc) and next day (day 5) IVIS® imaged for vector luciferase signals. The peritoneum was removed for imaging of the peritoneal cavity and the organs were harvested and imaged. All vectors targeted tumor implants. Tumors on the peritoneum, pancreas-omentum and bowel are circled. B) Some mice per group received a second i.p. injection of the vectors of day 6, and the peritoneal cavities (second row) and organs (bottom rows) were IVIS® imaged on day 7. One mouse per group (#28, 33, 38) was not injected to serve as a luciferase background control. Vectors B and C showed decreased bioluminescence signals in tumors compared with the first injection (A).

FIG. 9. SP6-H Ar-339 E2 mutants. Amino acids changed in Ar-339 E2 mutants Mut-1 (9C), Mut-2 (9D) and Mut-4 (9E). Sequences and residues from the JT-BB plasmid are shown in 9A, those corresponding to Ar-339 are represented in 9B.

FIGS. 10(A and B). Background infection of Ar-339 E2 mutants. A) Five tumor-free mice per group were i.p. injected on day 0 with one dose of vector A (JT-BB/SP6-RFluc), vector C (SP6-H/SP6-RFluc), Mut-1(SP6-H-K70/SP6-RFluc), Mut-2(SP6-H-K70-V251/SP6-RFluc) and Mut-4(SP6-H-I3-K70-E181-V251/SP6-RFluc). The next day, mice were IVIS® imaged for vector luciferase signals. The peritoneum was removed for imaging of the peritoneal cavity of representative mice and the organs were harvested and also imaged. The E2 mutant vectors did not show background infection of fat tissue as observed with vectors A and C. E2 mutant organ arrays were also IVIS® imaged at Bin 10 resolution to increase the detection limit (bottom row), arrows point to regions with signals. B) Some mice per group received a second i.p. injection of the vectors of day 2, organs were harvested and IVIS® imaged. Mice circled (#17, 24, 27, 32, and 39) were not injected to serve as luciferase background controls. Only using high sensitivity Bin 10 resolution, low bioluminescence signals (indicated with arrows) were detected in mice 21, 22 and 38 of vector groups A, C and Mut-4 respectively.

Figure 11A:
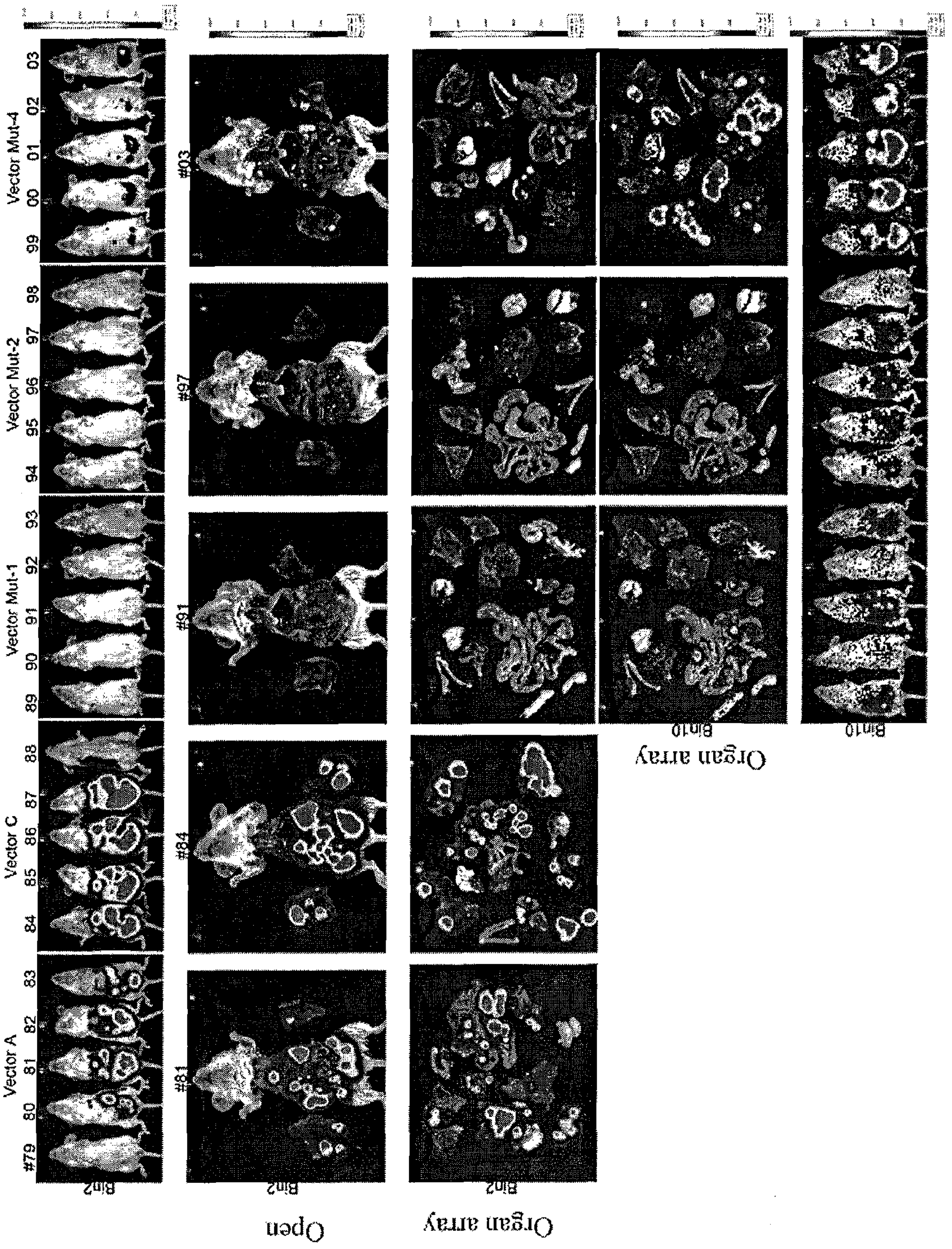
Figure 11B:
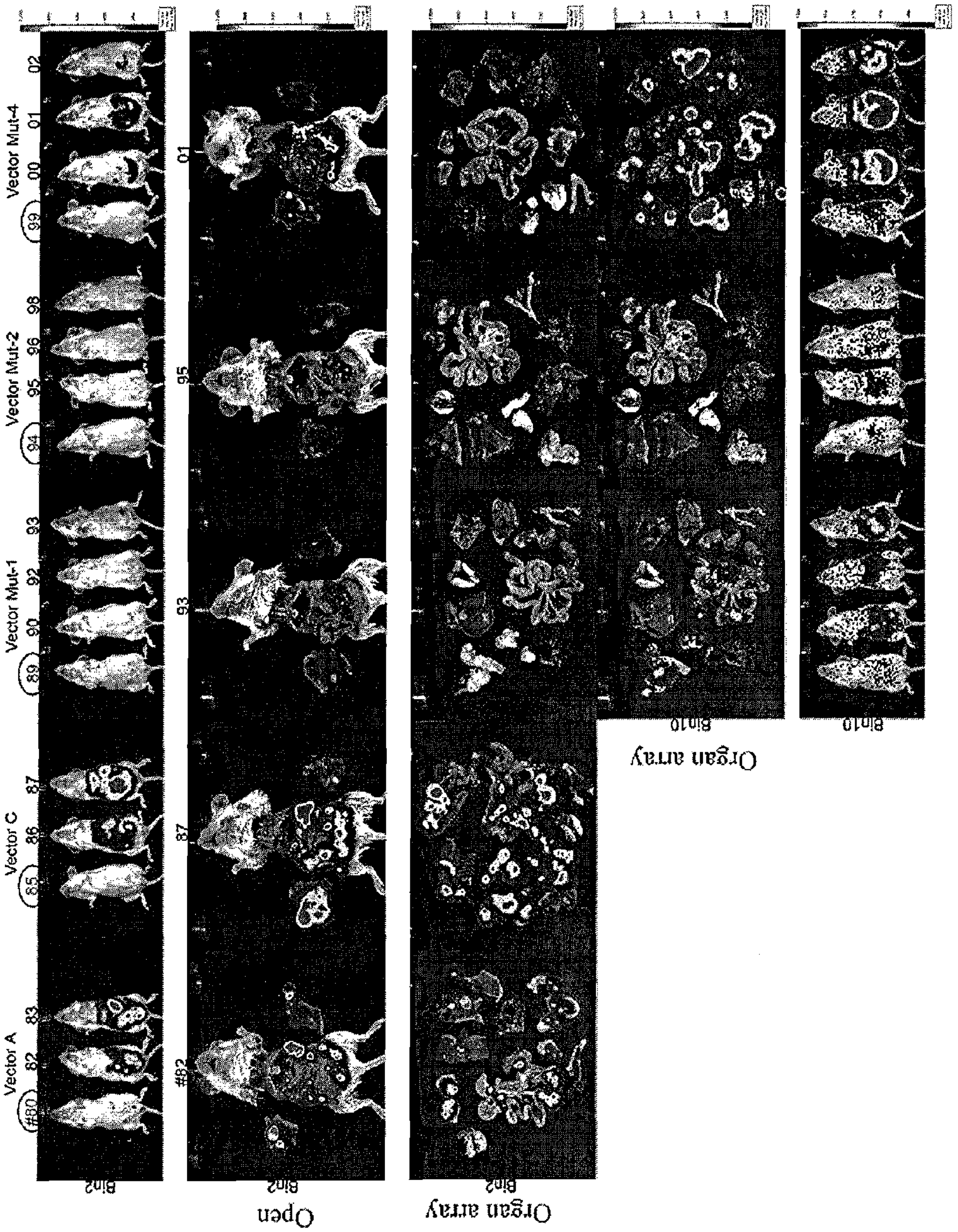

FIGS. 11(A and B). Tumor targeting of Ar-339 E2 mutants. A) SCID female mice were i.p. injected on day 0 with $2\times10^6$ ES-2 cells/mouse. On day 4, five mice per group were i.p. injected with one dose of vector A (JT-BB/SP6-RFluc), vector C (SP6-H/SP6-RFluc), Mut-1(SP6-H-K70/SP6-RFluc), Mut-2(SP6-H-K70-V251/SP6-RFluc) or Mut-4(SP6-H-I3-K70-E181-V251/SP6-RFluc), and the next day (day 5) IVIS® imaged for vector luciferase signals. The peritoneum was removed for imaging of the peritoneal cavity and the organs were harvested and imaged. Vectors A and C efficiently targeted tumors, Mut-4 showed low bioluminescence signals, Mut-1 and Mut-2 did not show luminescence. For the three mutants, IVIS® images at Bin 10 resolution were taken of full mice and organ arrays. Only at this high sensitivity did some mice of Mut-1 and Mut-2 groups show very low residual signals in metastatic implants (lower panels), arrows point to regions with signals. B) Some mice per group received a second i.p. injection of the vectors on day 6, and peritoneal cavities and organs were IVIS® imaged on day 7. One mouse per group (#80, 85, 89, 94 and 99) was not injected to serve as luciferase background controls. For the three E2 mutants, high sensitivity Bin 10 images were also taken. Vectors showed equivalent infection pattern as for first injection.

Figure 12A:
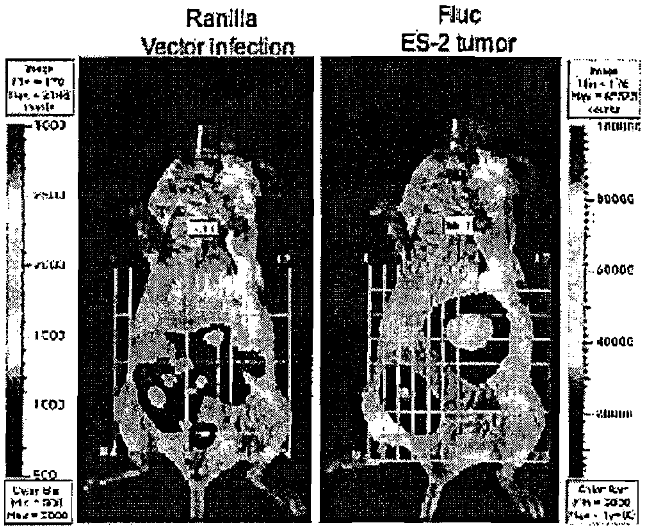
Figure 12:
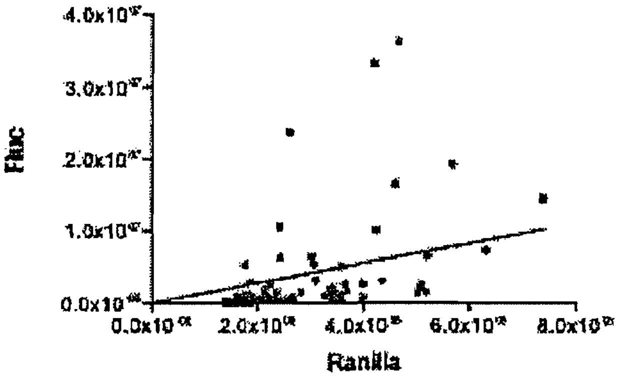

FIGS. 12(A and B) Colocalization in peritoneal cavity of vector Mut-4. A) Vector Mut-4 infection colocalized with the metastasized ES-2/Fluc tumors in the peritoneal cavity as determined by the IVIS® Imaging System. SCID mice were i.p. inoculated with $1.5\times10^6$ ES-2/Fluc cells. Five days later, while the disease was still microscopic, inoculated mice received a single i.p. treatment of vector Mut-4 and were imaged the next day. The first IVIS® imaging was done by i.p. injection of Rluc substrate, coelenterazine, followed by a 5-minute acquiring interval (left panel). Thirty minutes after the coelenterazine injection, when the short-lived Rluc signals faded away, Fluc substrate, D-luciferin, was i.p. injected to determine the ES-2/Fluc tumor locations (right panel). B) Correlation analysis of vector Mut-4 shows a high correspondence between tumor cells and vector infection in the peritoneal cavity.

Figure 13A:
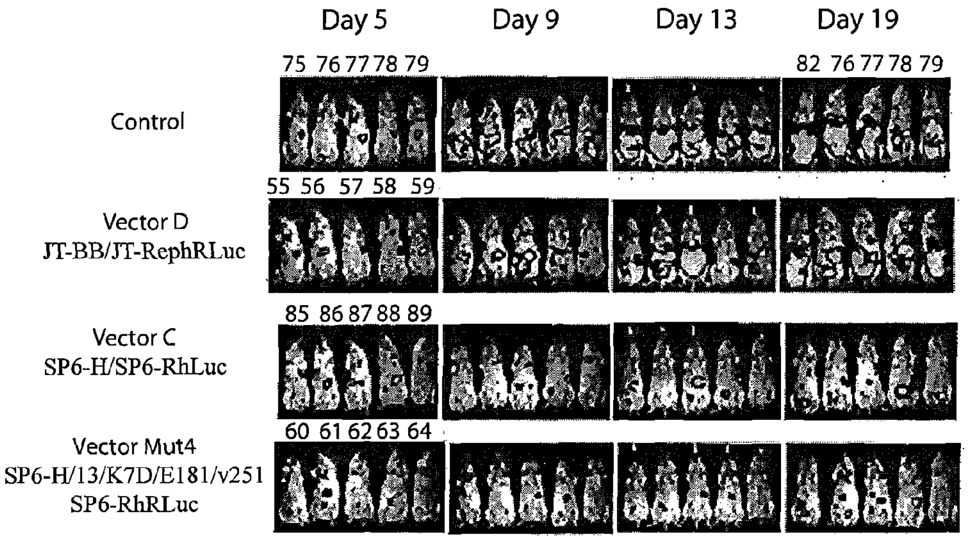
Figure 13B:
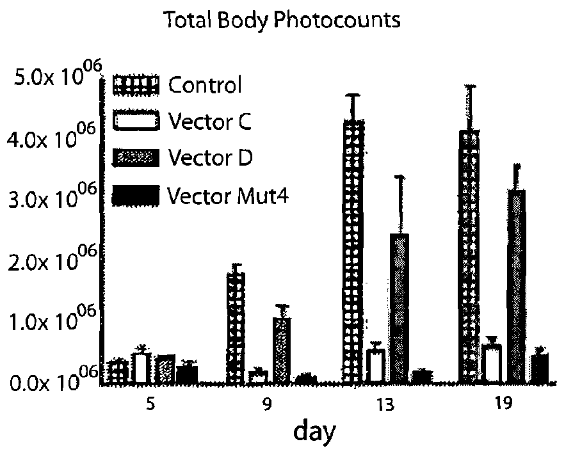
Figure 13C:
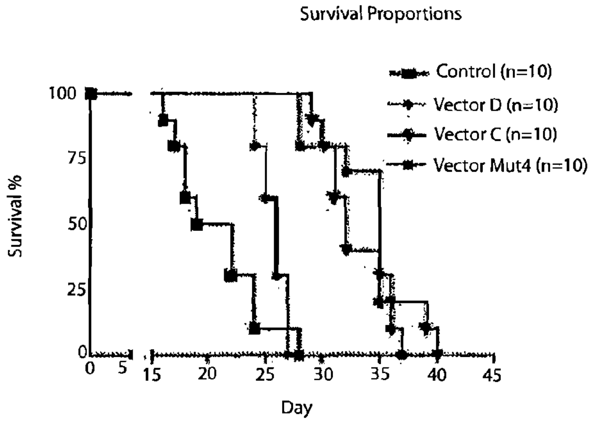

FIG. 13.(A-C) Suppression of disease progression by Ar-339 and Mut-4 chimeric vectors. A) ES-2/Fluc cells ($1.5\times10^6$) were i.p. inoculated into SCID mice on day 0. The next day (day 1), mice were imaged using the IVIS® Imaging System with D-luciferin as substrate and were split into four groups of five mice each: control which received no vector treatment, vector D, vector C and vector Mut-4. The groups received daily i.p. treatments of corresponding Sindbis vectors ($10^6$ TU) and were IVIS® imaged on days 1, 5, 13 and 19 after the start of treatment. All vector treatments suppressed the tumor growth on the mesentery and diaphragm and reduced the signals on the omentum compared with control mice. Image scale Min $8\times10^3$ Max $10^5$ counts/pixel. B) Quantitative analysis of the whole-body total photon counts of control and Sindbis-treated mice. Error bars represent the SEM. C) Survival curve of mice.

DETAILED DESCRIPTION OF THE INVENTION

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition. Cold Spring Harbor, N.Y.: Cold Spring Harbor Laboratory Press, 1989 (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); Ausubel, F. M. et al. (eds.). *Current Protocols in Molecular Biology.* John Wiley & Sons, Inc., 1994.

Amino acid residues in proteins are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Trytophan is Trp or W; Arginine is Arg or R; and Glycine is Gly or G.

As used herein, the term "tumor" refers to a malignant tissue comprising transformed cells that grow uncontrollably. Tumors include leukemias, lymphomas, myelomas, plasmacytomas, and the like, and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, neuroglioma, and retinoblastoma.

The phrase "pharmaceutically acceptable", as used in connection with compositions of the invention, refers to molecular entities and other ingredients of such compositions that are physiologically tolerable and do not typically produce untoward reactions when administered to a human.

Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "therapeutically effective" applied to dose or amount refers to that quantity of a compound or pharmaceutical composition that is sufficient to result in a desired activity upon administration to a mammal in need thereof. As used herein with respect to viral vectors of the invention, the term "therapeutically effective amount/dose" refers to the amount/dose of a vector or pharmaceutical composition containing the vector that is sufficient to produce an effective anti-tumor response upon administration to a mammal.

Described below are preferred replication defective Sindbis viral vectors for use in the present invention termed vector C, Mut-1, Mut-2 and Mut-4 and the plasmids used to produce them. Mut-1, Mut-2 and Mut-4 contain mutations in the E2 envelope protein and are alternatively referred to herein as "E2 Mutants".

The E2 mutants of the present invention were produced using unique helper and replicase plasmids. The present invention provides four novel helper plasmids (SP6-H (SEQ ID NO:37) SP6-H-K70 (SEQ ID NO:38), SP6-H-K70-V251 (SEQ ID NO:40) and SP6-H-I3-K70-E181-V251 (SEQ ID NO:39)) and one replicon plasmid (SP6-R (SEQ ID NO:36)). Helper plasmid SP6-H, which does not contain any amino acid changes but has a different nucleotide sequence, is set forth in SEQ ID NO:37. The 4 helper plasmids are used to produce Vector C, Mut-1-2 and -4 vectors, respectively, when produced using the novel replicon plasmid.

In order to produce viral vectors in this system, two plasmids are used, the replicon and the helper. The replicon contains the viral replicase, the viral packaging signal, nt 945 to nt 1075, (Weiss B et al. 1994; Frolova et al 1997); the viral subgenomic promoter, multicloning site 1 (MCS1) to allow for the insertion and expression of the gene of interest, and the 3' end of the virus (nt 11394 to 11703) to allow viral (−) strand RNA synthesis. A second multicloning site (MCS2) allows for the linearization of the plasmid for in vitro transcription.

The helper plasmid contains the first 425 nt of the virus, followed by the 3' end of the virus from nt 7334 to nt 11703 which includes the subgenomic promoter, the capsid and the viral envelope proteins (E3, E2, 6K and E1) and the 3' end (nt 11394 to 11703).

Both plasmids share the following viral sequences: the first 425 nt and the 309 nt of the 3' end and the sub genomic promoter.

Both plasmids have several non-viral elements in common, the replication origin (rep pMB1) and the Ampicillin resistance gene from the pUC cloning plasmid; the promoter for in vitro transcription (T7 or SP6) and the MCS2. In the construction process a plasmid containing the pUC sequences, SP6 or T7 promoter, the multicloning sites, and the 3' viral end, which are common to both vectors, was first generated. The specific viral sequences were then cloned into this plasmid (FIG. 3).

In order to produce the viral vectors of the present invention, one pair of plasmids are linearized using restriction enzymes such as PacI, NotI, or XhoI, transcribed in vitro, the RNAs collected and electroporated into cells. For in vitro transcription, a promoter is inserted before the Sindbis viral sequences. Preferably, the promoter is a bacteriophage promoter, for us with its respective RNA polymerase such as SP6 or T7 (Ambion Austin, Tex.).

Cells for use in the present invention include BHK-21 cells (available from the American Type Culture Collection, ATCC, Manassas, Va. as CRL 6281), ES-2 cells, (ATTC, CRL 1978), ES-2/Fluc cells that were derived from the ES-2 line by transfection of a plasmid, pIRES2-Luc/EGFP and the MOSEC cell line (clone ID8). The transcribed RNAs (i.e., one helper and one replicon plasmid) are electroporated into the cells at a concentration ranging between about 0.75 mg/mL and about 1.25 mg/mL. The ratio of viral RNA to cell concentration ranges between about 30-50 μg RNA per $6\times10^6$cells. Electroporation is performed using equipment commercially available from e.g., Bio Rad (Hercules, Calif.)

The transfected cells are fed medium containing 5% fetal bovine serum (FBS) and incubated at 37° C. for about 12 hours. The medium is then discarded, replaced with 9 ml of Opti-MEM I medium (GIBCO-BRL Invitrogen, San Diego Calif.) and incubated at about 37° C. for about 24 hours. Then, supernatents are collected and centrifugated at 2,400 rpm (≈1,500 g) for 15 min to eliminate cell debris. Clear supernatants, containing the viral vector, were collected, aliquoted and stored at −80° C.

The viral vectors can be used as anti-tumor agents as described in International Application No. PCT/US02/09432 published as WO 02/076468. Although the Mut-1 vectors do not bind to the high affinity laminin receptors (HALR), they are useful as controls and to monitor non-viral effects of the vectors. Since Mut-1 vectors do not enter cells, the contribution of host factors in the anti-cancer response can be studied.

The plasmids of the present invention can be used to transfer of cells and create packaging cell lines for the continuous production of defective Sindbi viral vectors as described in copending Ser. No. 10/983,432 and in Paper Example 1 below.

The amount of viral vectors produced may be determined as described below in the Examples. Briefly, clear supernatants are serial diluted in Opti-MEM I medium and 300 μL of each vector dilution are added to a 35 mm well in 12-well plates, containing $2\times10^5$ cells. After incubation for 1 hour at room temperature, the cells are washed with PBS (Phosphate buffered saline) and incubated with 2 mL of αMEM at 37° C. for about 24 hours. Media is removed, cells are washed with PBS and cell lysates are prepared and assayed for the different reporter activity: β-galactosidase, firefly luciferase or *Renilla luciferase*. Vector titers were estimated as the highest dilution having detectable reporter activity. Detection of reporter activities is described in Example 2.

Viral vectors can be produced by linearizing helper and replicon plasmids after the polyA sequence, followed by separately performed in vitro transcription reactions. Usually, 1.6 μg of plasmid yields 15-25 μg of mRNA/reaction. Then 30-50 μg of both RNAs are co-electroporated into $6\times10^6$ BHK-21 cells, which are then incubated in 10 ml of αMEM containing 5% FBS at 37° C. for about 12 h. Then, the medium is replaced with 9 ml of Opti-MEM I medium (GIBCO-BRL Invitrogen, San Diego Calif.) supplemented with 0.7 μM $CaCl_2$, cells are incubated at 37° C. for about 24 h, supernatants collected and centrifuged at ≈1,500 g for 15 min to eliminate cell debris. The procedure can be scaled up using the following electroporation ratios: 5-8 μg helper and replicon mRNA's per $10^6$ BHK-21 and 9 mL Ca-Opti-MEM media per reaction.

The viral vectors of the present inventions have the following properties which are summarized in Strauss and Strauss 1994. Briefly, as Alphaviruses replicate exclusively in the cytoplasm, there is no possibility of adventitious splicing. Because they are replication incompetent and packaging defective, the vectors are incapable of spread by reinfection. The vector replicates to high copy number inside the cell, and large quantities of mRNA are produced, leading to production of large amounts of the protein of interest Viral vectors obtained as described herein can be formulated in a pharmaceutical composition for administration to a patient. As used herein, a "pharmaceutical composition" includes the active agent, i.e., the viral vector, and a pharmaceutically acceptable carrier, excipient, or diluent. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

For human therapy, the viral vectors of the present invention may be prepared in accordance with good manufacturing process (GMP) standards, as set by the Food & Drug Administration (FDA). Quality assurance (QA) and quality control (QC) standards will include testing for replication competent virus (if the virus vector is replication defective), activity (colony forming units [CFU] per number of viral particles, tested by induction of apoptosis or cytopathic effect (CPE), or by expression of a marker gene such as β-galactosidase), toxicity, and other standard measures.

In order to treat the tumors, the pharmaceutical composition is administered by any route that will permit homing of the vector to the tumor cells. Preferably, administration is parenteral, including, but not limited to, intravenous, intraarteriole, intramuscular, intradermal, subcutaneous, intraperitoneal, intraventricular, and intracranial administration. As disclosed herein, viral vectors can be also administered to the tumor-bearing animal via intranasal or oral route (see Hardy, In: *The Arbiviruses: Epidemiology and Ecology,* Ch. 4, pp. 87-126). Importantly, however, in contrast to other viral vectors in gene therapy, administration of the Sindbis vectors of the invention need not be locally to the tumor. Indeed, one of the advantages of this invention is the high specificity and affinity of the vector for cancer cells, even micrometastases that cannot be resected or located by standard techniques (e.g., CAT scanning, MRI scanning, etc.).

In the therapeutic treatments of the invention, a therapeutically effective amount of the vector is administered to a patient. As used herein, the term "therapeutically effective amount" means an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. Specifically, a therapeutically effective amount will cause one or more of the following: apoptosis of tumor cells; necrosis of tumor cells; elimination or prevention of tumor metastases; reduction in the rate of tumor growth; reduction in tumor size or tumor shrinkage; scab formation over cutaneous tumor; elimination of the tumor; remission of the cancer; an increase in the time for reappearance of the cancer; and increased time of survival of the patient. The frequency and dosage of the vector therapy can be titrated by the ordinary physician using standard dose-to-response techniques, but generally will be in the range of from about $10^6$ to about $10^{12}$ viral vector particles per dose administered daily, weekly, biweekly, or monthly at least twice and preferably at least three times.

In order to explore if wild type Sindbis would improve the vector systems, four vectors were generated combining the helper and replicase segments of both strains (JT-BB/SP6-R; SP6-H/JT-Rep; SP6-H/SP6-R; JT-BB/JT-Rep) and tumor size reduction and survival in tumor-induced SCID mice was studied. Unexpectedly, it was found that those vectors carrying Ar-339 helper (SP6-H) were less efficient in targeting tumors than the JT vectors and that those carrying Ar-339 replicase (JT-BB/SP6-R and SP6-H/SP6-R) were more efficient in tumor reduction. To study the surprising phenotype of the helper, both viral sequences were analyzed and compared. One amino acid difference was found in the capsid protein ($Pro_{67}$ (JT-BB) to Gln (Ar-339)); three amino acid changes in envelope protein E1 ($Ala_{72}$ (JT-BB) to Val (Ar-339), $Gly_{75}$ (JT-BB) to Asp (Ar-339) and $Ser_{237}$ (JT-BB) to Ala (Ar-339)) and four changes in envelope protein E2 ($Ile_3$(JT-BB) to Thr(AR-339); $Lys_{70}$(JT-BB) to Glu(Ar-339); $Glu_{181}$(JT-BB) to Lys(Ar-339) and $Val_{251}$(JT-BB) to Ala(Ar-339)). To determine which amino acids were critical for the vector properties, different chimeras from both vectors were generated containing mixed sequences from both strains. The analysis in animal models showed that the Ar-339 E2 envelope protein sequence was primarily responsible for tumor metastases targeting although the optimum amino acid pattern was not defined. To address this question, vectors were generated containing sequences with mixed combinations of the four amino acids in E2, for JT and Ar-339, and tested by IVIS® imaging in ES-2 induced and tumor-free mouse models. Surprisingly, the change of only one amino acid from Glu to Lys at position 70 of Ar-339 E2, suppressed the ability to target metastatic tumor implants in mice and also showed no fat tissue background. This result was unexpected, considering that this mutant (Mut-1) repeatedly showed titers equivalent to the Ar-339 vector when measured in ES-2 cultured cells. Double mutant Mut-2, with K70 and V251 did not revert the targeting. Only when the whole sequence of JT E2 was substituted in the Ar-339 helper was the ability to target metastatic tumor implants recovered, a though with less intensity. Thus, residue 70 in the outer leaf of the E2 protein is essential for tumor specific targeting of vectors.

Described herein are amino acids of Sindbis viral vectors involved in specific infection of metastatic tumor implants in the mouse peritoneal cavity. Sequence analysis of cloned Ar-339 and JT viral vectors has been an important tool for the discovery of these amino acids.

The sequence analysis comparison with the published Strauss sequence, revealed 2 or 3 amino acid changes in viral replicase for JT and Ar-339 respectively. The Ar-339 nsP1 Ile 441 is a reverse mutation to an alphavirus conserved residue; this amino acid may also be related to viral adaptation to BHK-21 tissue culture. Ar-339 replicase is more efficient in suppression of disease progression than JT, the change from polar Cys in JT to aliphatic residue, Ile 441, may play a role in enhancing replicase activity. Interestingly, both JT and Ar-339 vectors have the same 2 amino acid changes in nsP2 protein versus the Strauss sequence. JT and Ar-339 nsP2 residues are more conserved among the Sindbis-like Alphavirus group.

Comparing the Strauss sequence with the region coding for the structural part of the JT and Ar-339 vectors, the changed amino acids were found mainly in the viral spike, although in different residues, suggesting a different evolutionary lineage of both strains. E1 D75 and A237 of Ar-339 are highly conserved in Sindbis-like alphaviruses; all viruses in this group carry D75. There is no virus in the group that has serine at 237, which only occurs in the JT vector. These data suggest that E1 G75 and S237 of JT vector may more likely be point mutations that arose in this laboratory strain. Further studies with E1 mutants should reveal the implication of these E1 residues in the specific tumor targeting of the viral vector. Most of the sequence variabilities have been found at the E2 envelope protein in the leaf-like domain at the viral spike; these residues are also poorly conserved in the Sindbis-like alphavirus group. The role of these E2 spike mutations in mouse tumor models in vivo was examined.

The fact that the Mut-1 vector shows the same titer as the Ar-339 vector in ES-2 cells, but does not efficiently infect ES-2 metastatic tumor implants in mice, represents a powerful tool for the study and the improvement of Sindbis vectors for gene therapy. One cause of the loss of tumor targeting in vivo could be a reduced stability of the vector in mice. Alignment of protein sequences among 17 different viruses of the Sindbis-like alphavirus group showed that ten out of the 17 members have a gap in Sindbis E2 residues 68-71, including Semliki Forest virus (SFV) which has a comparable structure to Sindbis virus. The viral spike is composed of three E1-E2 heterodimers that lean against each other. There is a gap between the base of neighboring E1-E2 heterodimers which would allow E2 to move out of the center of the spike during fusion (Zhang et al. 2002). In addition, previous studies with stable deletion mutants in the E2 receptor binding domain, also show equivalent in vitro titers but drastic reduction of infectivity in live *Aedes aegypti* mosquitoes (Myles et al. 2003). Without wishing to be bound by theory, it is believed that these data suggest that there is structural flexibility in this area of the spike, therefore, alterations in residue 70 shouldn't be critical for Mut-1 vector stability in vivo. The loss of vector infectivity would be more likely to occur via a decrease in cell binding affinity, especially in vivo, where the environmental conditions for vector infection are more restrictive.

In Sindbis and Semliki Forest virus (SFV), the residues involved in host cell fusion and binding to cellular receptors are located in the viral spike. It has been described that only one change from the small non-polar Valine, at position 75, to the acidic Aspartic acid in E1 SFV spike subunit, modifies the cell-cell fusion properties of the virus (Levy-Mintz and Kielian, 1991). Amino acids in these E1 and E2 spike domains are, thus, important in spike configuration and virus infectivity.

The vector Ar-339, having hydrophobic (V72), and acidic (D75) residues in E1 and a glutamic acid (E70) in E2 protein, is able to efficiently target tumor cells in vivo. In Mut-1, in which E2 residue 70 is changed to lysine, there is a change in polarity and charge of the amino acid that would change the conformation of the spike and so the cell binding properties of the vector. This hypothesis is supported by the difference in cell tropism observed in vitro between Mut-1 and Ar-339. Only the recovery of the full sequence of JT-BB E2 in Mut-4 results in higher titers in BHK-21 cells. If these differences were observed in vitro, where the conditions for cell binding are optimized, it is possible that in vivo factors involved in cell-vector interactions might be able to prevent vector adherence to the viral receptor. Ar-339 and Mut-1 vectors have the same titer in ES-2 cells in vitro, but in mouse metastatic implants, where ES-2 cells are in a different environments and could have receptor variations, small affinity differences between both vectors are revealed.

The present invention is described further below in examples which are intended to describe the invention without limiting the scope thereof.

In the examples below, the following materials and methods were used.

EXAMPLE 1

Sindbis cDNA Cloning

Common Techniques

Virus Propagation

Sindbis virus strain Ar-339 (Original) was obtained from ATCC (Manassas, Va., Item #VR-68) and propagated on a secondary chicken embryo fibroblast cell line, CEF. Cells were cultured in EMEM media (BioWhittaker, cat#12-684) supplemented with 10% Fetal bovine sera, $NaHCO_3$ 1.5 g/l; 1-Glutamine, 292 mg/l and Penicillin/Streptomycin, 100 U/ml. Two T-75 flasks with 80% confluent CEF cell monolayers, were infected with $2.5\times10^7$ pfu and $5\times10^7$ pfu, respectively, of Sindbis virus Ar-339, diluted in 1 ml of Opti-Mem I media (GIBCO-BRL Invitrogen, San Diego Calif.; cat#31985-070) supplemented with 0.7 μM $CaCl_2$. Virus-infected cells were incubated at 37° C. for 1 h, 10 ml of EMEM media/flask added, and cells were incubated overnight at 37° C. Supernatants containing the Sindbis "innocula" were harvested and stored at −80° C. until used in further infections. CEF cells were collected for total RNA extraction.

RNA Extraction

5 T-75 flasks with 90% confluent CEF monolayers were incubated 1 h at 37° C. with 1:100; 1:20; 1:10; and 1:5 dilutions (in Ca-OPTI-MEM media) of previously obtained "Sindbis innocula". Ten ml of EMEM media/flask was then added and incubated overnight at 37° C. After collecting the supernatant, 2 ml of Trizol (Invitrogen, San Diego, Calif.; cat # 15596-018) per flask was added to the infected cells, the extract collected and stored at −80° C. Total RNA from infected cells was prepared following the manufacturer's (Trizol) protocol. Briefly, 1 ml of Trizol cell extract was vortexed for 15 seconds, 200 μL of chloroform added, vortexed, spun at 15,000 g for 10 min at room temperature (rt), the aqueous upper phase transferred to a clean tube, 750 μL of isopropanol added, incubated at rt for 15 min, spun again, the supernatant removed and the pellet washed with ethanol (70% in DEPC water). The pellet was air dried at rt for 5-10 min, and resuspended in 50 μL of DEPC water.

Figure 1:
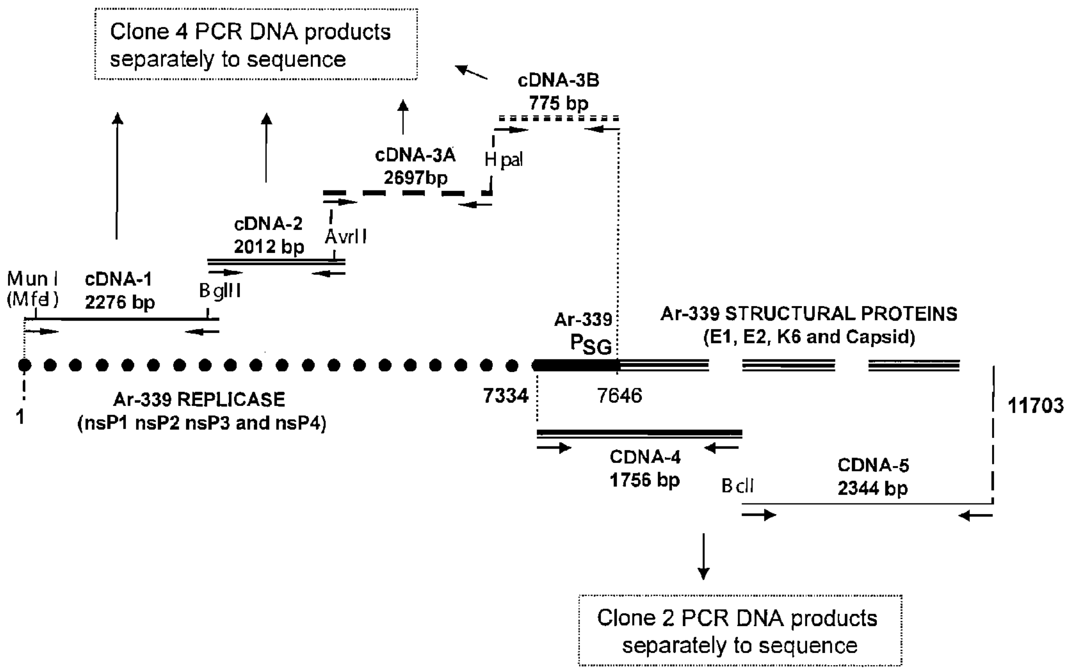
FIG. 1 Sindbis virus Ar-339 cDNA cloning.

Sindbis c-DNA Cloning. Sindbis virus RNA was cloned in 6 overlapping fragments (CDNA-1, CDNA-2, CDNA-3A, CDNA-3-B, CDNA-4 and CDNA-5) into sequencing plasmid pCR4Blunt-TOPO (Invitrogen, San Diego Calif.; cat#45-0245). The position of the fragments is shown in FIG. 1 and the sequences of the primers used are shown in Table I (Appendix A). The primers were designed to take advantage of the unique restriction sites of the virus. In primer SV-C3R RE XbaI was introduced to allow CDNA-3 cloning. For each fragment the RT and the PCR reactions were performed with the same pair of primers. The cloning procedure was the same for all of the fragments except for the conditions of the PCR cycles.

Reverse transcriptase (RT) reactions were performed with: 5 μg from total RNA from infected cells, reaction buffer (1×); forward and reverse specific primers (2.5 μM/each); dNTPs (1 mM); DTT (5 mM) and 15 u of ThermoScript™ RNase $H^-$Reverse Transcriptase (Invitrogen, cat#12236-014), in a final volume of 20 μL. RT was diluted 1:1 in distilled water prior to use in PCR.

The Pfx-PCR reactions were performed with 1 μL of RT reaction, reaction buffer (1×), $MgSO_4$(1 mM), dNTPs (0.3 mM/each), forward and reverse primers (0.3 μM/each) and 1 U Platinum Pfx DNA Polymerase (Invitrogen, cat#11708-013) in final volume of 25 μl. RT and PCR reactions were performed in an Eppendorf "Mastercycler Gradient" Thermal Cycler. Taq-PCR reactions contained reaction buffer (1×); dNTP's (200 μM), forward and reverse primers (0.5 μM/each) and 1 u Taq-DNA-polymerase (Fisher Scientific, Pittsburgh, Pa., cat#FB 600025) in a final volume of 20 μl. In both cases PCR products were analyzed by electrophoresis in 1% agarose gels and DNA bands cut out and purified with a QIAEXII gel extraction kit (Qiagen, Valencia Calif.; cat# 20021)

All enzymes were purchased from New England Biolabs (NEB, Beverly, Mass.). After digestions with restriction enzymes (RE), extracted DNAs were CIP dephosphorylated (1 h at 37° C.) and/or phosphorylated with T4-Polynucleotide-Kinase (1 h, 37° C.), enzymes were inactivated (70° C., 10 min or 65° C. 20 min) and reactions were run in 1% agarose gels. Bands were cut out, extracted, and quantified by gel electrophoresis by comparison with bands of known DNA concentration. Ligations were carried out with T4-DNA-Ligase (NEB) (16° C. 14 h) or with the Quick ligation kit (NEB) (5 min at room temperature (rt)). Transformations were performed using RapidTrans™ TAM1 extra competent *E. coli* (Active Motif, Carlsbad, Calif.; cat#11099). After transforming *E. coli* with the ligations, the first screening of positive bacteria was done by Taq-PCR of *E. coli* colonies. Positive plasmids were checked by restriction enzymes. Sequencing was done at the Skirball Institute of Biomolecular Medicine, NYU.

CDNA-1 plasmid. RT reaction was performed with primers CDNA-1F/CDNA1-R at 55° C. 1 h. Two Pfx-PCR were performed: 94° C. 5 min; 35 cycles [94° C. 30 s; 66° C., 30 s (band D) or [67° C., 30 s ;72° C., 2.5 min and 72° C., 2.5 min](band E). PCR products were run in 1% agarose gels and both 2.2 Kb bands, D and E, were isolated and cloned separately into the pCR4Blunt-TOPO plasmid. Positive colonies were screened using the same PCR conditions with 65° C. as the annealing temperature and Taq-DNA-Polymerase. Two plasmids were selected (one from each PCR band) and the PCR band D in plasmid CDNA-1_Topo#64 was completely sequenced. The sequence was compared to the Ar-339 sequence published by Strauss et al., *Virology* 133, 1984. The differences found were compared with-the sequences of PCR band E. Identical differences were found in bands D and E to confirm that they came from the virus and not from PCR mutations.

CDNA-2 plasmid. The Reverse transcriptase reaction was performed with primers CDNA-2F/CDNA-2R for 1 h at 55° C. Three PCR in gradient 94° C., 5 min; 35 cycles of [94° C., 30 s; 64.7° C., 30 s (band 1); or 66° C., 30 s (band 2); or 67° C. 30 s (band 3); 72° C., 2.5 min] and 72° C., 2.5 min. After cloning the 2 kb bands separately in pCR4Blunt-TOPO, PCR screening of colonies was done at an annealing temperature of 64.5° C. Band 2 in plasmid CDNA-2#213 was fully sequenced, and any mutations found were checked by comparison with the sequences of PCR bands 1 and 3.

CDNA-3A plasmid. Three RT reactions were performed in gradient with primers CDNA-3F/SV-6932R at 53.2° C., 55.5° C. and 60.8° C. respectively for 1 h 30 min. Three Pfx PCR were performed with 1 μL of each RT, respectively: 94° C., 5 min; 35 cycles of [94° C., 30 s; 53° C., 30 s; 72° C., 3 min] and 72° C. 3 min. The 2.68 kbp bands T,U and V were cloned separately and band V in plasmid C3A_Topo#735 was fully sequenced. No changes were found compared with the published Ar-339 sequences (Strauss et al.1984).

CDNA-3B plasmid. RT reaction was performed with primers SV-6882F/SV-C3R at 60.8° C. for 1 h 30 min. Three Pfx-PCR in gradient were performed with 94° C., 5 min; 35 cycles of [94° C., 30 s; 55.3° C., 30 s (band J); or 56° C., 30 s (band K); or 58.3° C. 30 s (band L); 72° C., 1 min] and 72° C., 2 min. The three 774 bp bands were cloned separately and band L, in plasmid C3B-Topo#334, was fully sequenced. The mutations found were confirmed by sequencing bands J and K.

CDNA-3 (CDNA-3A+3B) plasmid. HpaI RE is not unique in the Sindbis sequence, so in order to clone CDNA3A and CDNA3B fragments into the new reporter vector, it was necessary to generate first a Topo plasmid containing both sequences, and then clone fragment CDNA-3(CDNA-3A+3B) in the AvrII/XbaI site. Plasmid C3B-Topo#334 was HpaI and SacI digested and the 774 bp viral band was isolated from the agarose gel and ligated (T4-DNA-Ligase 16° C. 14 h) to HpaI/SacI digested C3A_Topo#735 plasmid. Transformants were screened by PCR with Taq-Polymerase, and primers CDNA-3F, SV-C3R at: 94° C., 10 min; 35 cycles of [94° C. 30 s; 55° C., 30 s; 72° C., 3 min] and 72° C. 2 min. The positive plasmid was named C3A+B_Topo#810, and the junctions were sequenced.

CDNA-4plasmid. The RT reaction was performed with primers CDNA-4F/CDNA4-R at 52° C. for 1 h 30 min. Three PCRs were performed in gradient with 94° C., 5 min; 35 cycles of [94° C., 45 s; 49.7° C., 30 s (band M); or 55° C., 30 s (band N); or 57.2° C., 30 s (band O); 72° C. 2.5 min] and 72° C. 2.5 min. The 2 kbp bands were isolated and cloned separately, band N in plasmid CDNA-4_Topo#422 was fully sequenced. The mutations found were confirmed by sequencing bands M and O.

CDNA-5 plasmid. RT reactions performed with primers CDNA-5F/CDNA5-R at 49.7° C. for 1 h 30 min. Three PCR were made in gradient with 94° C., 5 min; 35 cycles of [94° C., 30 s 46.8° C., 30 s (band Q); or 48.6° C., 30 s (band R); or 50.5° C., 30 s (band S); 72° C. 2 min] and 72° C., 2 min. The 2.35 kbp bands were cloned separately and band S in plasmid CDNA-5_Topo#525 was fully sequenced. The mutations found were confirmed by sequencing bands Q and R.Vectors construction.

Polylinker cloning in pUC plasmid. In summary, the SP6 and T7 Polylinker bands were constructed out of primers in two fragments, a 5' end containing the SP6 promoter (primer pairs Poly1-SP6(+)/Poly-2(−)) or T7 promoter (primers Poly1-T7(+)/Poly-2(−)) and a common 3'end (primers Poly-3(+)/Poly-4(−)) the sequences of the primers are given in Table II (Appendix A). 5' and 3' bands were digested and ligated to generate the polylinker and then were ligated to the AflIII/AatII pUC band containing the *E. coli* replication origin and Ampicillin resistance gene to generate T7-pUC or SP6-pUC plasmids.

T7-pUCplasmid. Two separate reactions were performed with primers pairs Poly1-T7(+)/Poly-2(−) or Poly-3(+)/Poly-4(−). For both reactions, conditions were: primers (5 μg each), buffer (1×), dNTPs (1.5 mM), BSA (50 μg/ml). Mixes were boiled for 5 min and cooled down to room temperature for primer annealing, 3 units/reaction of T4-DNA-Polymerase was then added to a final volume of 20 μl, and incubated at 37° C., for 30 min for chain extension.

0.5 μL of each reaction was used as a template in two PCR reactions: one with template Poly1-T7(+)/Poly-2(−) and primers PCR-Poly1-F/PCR-Poly2-R and other with template Poly-3(+)/Poly-4(−) and primers PCR-Poly-3F/PCR-Poly-4R. For both PCRs, the conditions were: reaction buffer (1×), dNTP's (200 μM), forward and reverse primers (0.5 μM/each) and 1 unit of Taq-DNA-polymerase in a final volume of 20 μl. For each primary reaction, 3 secondary tubes were prepared and PCR reactions were performed in gradient for annealing temperature: 94° C., 5 min; 35 cycles of [94° C., 30 s; 40° C., 30 s (tube 1); or 45.4° C., 30 s (tube 2); or 50.7° C., 30 s (tube 3); 72° C., 30 s] and 72° C. 1 min. Bands were stronger for the 40° C. annealing temperature. The 145 bp bands were then isolated and digested with enzymes: AflIII and XbaI for PolyT7/Poly2-R and, AatII and XbaI for Poly3(+)/Poly 4(−). After inactivating the enzymes at 65° C. 20 min, the ligation of equimolar amounts of both bands was carried out at 25° C. for 1 h with $T_4$-DNA-ligase. The 1811 nt AatII/AflII band of the pUC plasmid was added, and incubated at 16° C. overnight. *E. coli* Tam1 competent cells were transformed with the ligations and positively selected colonies screened by double digestion with AatII and AflIII. The positive plasmid was named T7-pUC#32 and was checked by sequencing.

SP6-pUCplasmid. The reaction mix: Poly1-SP6(+) and Poly-2(−) primers (5 μg each), buffer (1×), dNTPs (1.5 mM), BSA(50 μg/ml), was boiled for 5 min and cooled down to rt for primer annealing. Then 3 units/reaction of T4-DNA-Polymerase was added to a final volume of 20 μl, and incubated at 37° C., 30 min. 0.5 μl/Rxn was used as a template in a gradient PCR reaction with PCR-Poly1-F/PCR-Poly2-R primers (0.5 μM/each) reaction buffer (1×), dNTP's (200 μM), and 1 unit of Taq-DNA-polymerase in a final volume of 20 μl. PCR conditions: 94° C., 5 min; 35 cycles of [94° C., 30 s; 40° C., 30 s (tube 4); or 45.4° C., 30 s (tube 5); or 50.7° C., 30 s (tube 6); 72° C., 30 s] and 72° C. 1 min. Bands were isolated in agarose gels, pooled together and purified. The DNA obtained was digested with enzymes AflIII and XbaI for 2 h at 37° C. After inactivating the enzymes at 65° C., 20 min, the digested DNA band was ligated to the AatII and XbaI digested Poly-3(+)/Poly-4(−) band at 25° C. for 1 h with T4-DNA-ligase. Five μL of the ligation was used as the template for a second gradient PCR reaction carried out with primers PCR-Poly1-F and PCR-Poly4-R, (same concentrations as previous PCR) and cycles: 94° C. 2 min, 18 cycles of [94° C., 30 s; 40° C., 30 s (tube 4); or 43.1° C., 30 s (tube 5); or 45.4° C., 30 s (tube 6); 72° C. 30 s] and 72° C. 1 min. Bands were isolated in an agarose gel, pooled together, purified and AflIII/AatII digested at 37° C. for 16 h. After enzyme inactivation (65° C., 20 min), the AflIII/AatII SP6 band was ligated to the 1811 nt AatII/AflII band of the pUC plasmid with Quick T4-DNA-ligase (New England Biolabs) at rt for 5 min and transformed into *E. coli* Tam1 cells. Screening of colonies was performed as for T7 polylinker. The plasmid was named SP6-pUC#51.

T7-pUC-PolyA#114plasmid. The Sindbis 3'end from nt 11392 to 11694 was obtained by PCR on plasmid CDNA-5_Topo #525 with primers: PolyA-F (5' CCCCAATGATCCGACCA 3") (SEQ ID NO: 1) and PolyA-R (5' AAAACAAATTTTGTTGATTAATAAAAG 3") (SEQ ID NO:2). PCR conditions: reaction buffer (1×), $MgSO_4$(1 mM), dNTPs (0.3 mM each), primers (0.3 μM each) and 1 unit of Platinum Pfx DNA Polymerase in a final volume of 25 μl. Three PCR reactions were performed in gradient for annealing temperature: 94° C., 5 min; 35 cycles of [94° C., 45 s; 53.2° C., 30 s (tube 1); or 55.5° C., 30 s (tube 2); or 60.8° C., 30 s (tube 3); 72° C. 45 s] and 72° C. 1 min. The 53.2° C. band was stronger and its DNA was isolated from the gel, phosphorylated with 10 units of T4-Polynucleotide-Kinase (Biolabs) at 37° C., 30 min. After inactivation at 70° C. 10 min, the DNA was ligated to plasmid T7-pUC#32 (previously digested with HpaI and dephosphorylated) using $T_4$-DNA-ligase at 16° C. for 14 h. Screening of recombinants was performed by PCR of colonies using the same primers, Taq-Polymerase and cycles: 94° C., 5 min; 35 cycles of [94° C., 45 s; 53° C., 30 s; 72° C. 45 s] and 72° C. 1 min. The orientation of the insert was analyzed with restriction enzymes AflII/AseI. The positive plasmid was confirmed by sequencing, and named T7-pUC-PolyA#114. From this vector the final vector T7-ARep#68 and SP6-pUC-PolyA#914 was generated to construct the final vector SP6-Arep#68.

Replicon vector constructions. T7-ARepplasmid: Viral cDNA fragments CDNA-1, CDNA-2, and CDNA-3 were cloned in T7-pUC-PolyA#114 to generate a new reporter vector T7-ARep#68. Plasmid CDNA-1_Topo#64 was digested with MfeI and BglII RE and the 2247 bp viral band isolated and ligated, with the quick ligase kit, to T7-pUC-PolyA#114, MfeI, BglII digested and CIP dephosphorylated.TAM1 transformant bacteria were screened by PCR with Taq-Polymerase and primers CDNA-1F and CDNA-1R at: 94° C. 10 min, 35 cycles of [94° C., 30s; 65° C., 30 s; 72° C. 2.5 min] and 72° C. 2 min. The positive plasmid was named T7-pUC-PolyA-C1#11 and was AvrII/BglII digested and CIP dephosphorylated and ligated, with Quick ligase, to the CDNA-2 1950 bp viral band, obtained after AvrII/BglII digestion of plasmid CDNA-2_Topo#213. Screening of positive colonies was made by PCR with Taq polymerase and primers CDNA-2F and CDNA-2R at: 94° C., 10 min; 35 cycles of [94° C., 30 s; 64° C., 30 s; 72° C. 2.5 m] and 72° C. for 3 min. The plasmid was named T7-pUC-PolyA-C1-C2#3 5. C3A+B_Topo#810 was digested with XbaI/AvrII and BsshII, the 3350 nt viral C3 band separated in an agarose gel, isolated and ligated (Quick Ligase Kit) to XbaI/AvrII digested T7-pUC-PolyA-C1-C2#35 plasmid. Transformants were analyzed by XbaI/AvrII digestion. The new reporter vector was named T7-ARep#68, and was fully sequenced.

SP6-ARep plasmid. The reporter vector under the SP6 promoter was cloned in three steps. First, the SP6 promoter was cloned into T7-pUC-PolyA#114, then CDNA-1 was inserted and in the last step, the CDNA-2+CDNA-3 band from T7-ARep#68 was cloned.

SP6-pUC#51 was SphI and AflIII digested and the 154 nt band isolated and ligated (T4-DNA-ligase) to the T7-pUC-PolyA#114 SphI/AflIII/CIP band. Plasmids were screened by MboII digestion and checked by sequencing. The positive plasmid was named SP6-pUC-PolyA#902, and was digested with MfeI and BglII, CIP dephosphorylated and ligated (quick ligase) to the MfeI/BglII CDNA-1 band. Colonies were analyzed by PCR with CDNA-1F/CDNA-1R primers at: 94° C. 10 min, 35 cycles of [94° C., 30 s; 65° C., 30 s; 72° C., 2.5 min] and 72° C. 2 min. the positive plasmid was also analyzed by MfeI/BglII digestion and named SP6-pUC-PolyA-C1#306. Plasmid T7-ARep#68 was BglII/XbaI digested, and a 5.6 kb CDNA-2+CDNA-3 band was isolated from an agarose gel and ligated to BglII/XbaI/CIP digested SP6-pUC-PolyA-C1#306 plasmid. Screening was done by BglII and BglII/XbaI digestions. The new vector was named SP6-Arep#701.

Helper vector constructions. T7-AH#17plasmid. In a first step Sindbis virus nts 1 to 425 were cloned into T7-pUC-PolyA#114. In a second step, both CDNA-4 and CDNA-5 viral fragments were cloned to generate a new helper vector. Sindbis nt 1 to 425 were amplified by PCR using as a template 54 ng of CDNA-1_Topo#64, primers (0.5 μM/each) SIN1-19F (5' ATTGACGGCGTAGTACACA 3') (SEQ ID NO:3) and H-BamR (5' GTATCAAGTAGGATC-CGGAG 3') (SEQ ID NO:4) which adds a BamHI RE to allow CDNA-4 fragment cloning, reaction buffer (1×), dNTP's (200 μM), and 1 unit of Taq-DNA-polymerase in final volume of 20 μl. Two PCR reactions were performed in gradient for the following annealing temperature: 94° C. 5 min, 28 cycles of [94° C., 30 s; 45.3° C., 30 s (tube 1); or 46.4° C., 30 s (tube 2); 72° C., 30 s] and 72° C. 1 min. Bands were analyzed in agarose 1.3% gels, extracted, pooled together and digested with MfeI/BamHI. Plasmid T7-pUC-PolyA#114 was MfeI/BamHI digested and CIP dephosphorylated, the band isolated from an agarose gel and ligated to the 350 bp MfeI/BamHI PCR band. Colonies were screened by Taq-PCR with primers SIN1-19F/H-BamR at: 94° C., 10 min; 45 cycles of [94° C., 30 s; 45° C., 30 s; 72° C. 30 s] and 72° C. 1 min. A positive plasmid was checked by sequencing and named T7-pUC-PolyA-5'#604. This plasmid was digested with BamHI and NsiI and CIP dephosphorylated to ligate with viral inserts.

The ligation of CDNA-4 and CDNA-5 was through RE BclI. This enzyme is dam methylation dependent, so to demethylate the DNA, plasmids harboring CDNA-4_Topo#422 and CDNA-5_Topo#525 were transformed into dam⁻/dcm⁻ *E. coli* strain GM2163 (New England Biolabs). CDNA-4_Topo#422(dam−) was BamHI and BclI digested and plasmid CDNA-5_Topo#525 was digested with BclI and NsiI. In both cases, the enzymes were inactivated at 70° C. for 15 min. The ligation was performed with T4-DNA-Ligase (16° C. for 14 h) with equimolar amounts of the three bands: T7-pUC-PolyA-5'#604 (BamHI/NsiI/CIP), CDNA-4_Topo#422(dam⁻) (BamHI/BclI) and CDNA-5_Topo#525(dam⁻) (BclI/NsiI). Colonies were screened by BamHI and NsiI digestion. The positive plasmid was named T7-AH#17 and was fully sequenced.

SP6-AH plasmid. Plasmid SP6-pUC-PolyA#902 was digested with MfeI and NsiI, CIP treated and the 2.4 kb band was ligated (T4-DNA-ligase) to the 4.5 kb T7-AH#17 MfeI/NsiI band. Colonies were screened by Taq PCR with primers CDNA-5F and CDNA-5R at: 94° C., 10 min; 25 cycles of [94° C., 30 s; 53° C., 30 s; 72° C. 3 min]. Positive plasmids were checked by NsiI, and NsiI/MfeI digestions and sequenced. The resulting plasmid was named SP6-AH#318

T7-R AND SP6-R plasmids. The four plasmids (SP6-AH#318, SP6-ARep#701, T7-AH#17 and T7-ARep#68) were fully sequenced, and in all four, a deletion of one T at the 3' end of the virus before the polyA, nt 11686 was found. In order to have the same sequence as the virus Ar-339, the deletion was fixed.

The Ar-339 sequence was placed first in plasmid T7-pUC-polyA#114. The new 3' end was obtained by PCR with primers: PolyA-F (5' CCCCAATGATCCGACCA 3") (SEQ ID NO:5) and END-R (5' AAAACAAA ATTTTGTTGATTAATAAAAG 3') (SEQ ID NO:6) and cloned into T7-pUC#32, as described previously for T7-pUC-polyA#114 cloning. The new plasmid T7-pUC-3end#9 was sequenced and used to generate new helpers and reporters.

To generate the reporter vectors, the T7-pUC-3end#9 plasmid was digested with XbaI and XhoI and the 423 bp band was cloned into the SP6-Arep#701 XbaI/XhoI 9504 bp band and into the T7-ARep#68 XbaI/XhoI 9504 bp band to generate new reporters SP6-R#406 and T7-R#202, respectively.

T7-HAND SP6-H plasmids. Plasmid T7-pUC-3end#9 was digested with NsiI and XhoI and the 311 bp band was cloned into the SP6-AH#38 NsiI/XhoI 6399 bp band and into the T7-AH#17 NsiI/XhoI 6399 bp band, to generate, respectively, the new helpers SP6-H#432 and T7-H#226. The new reporters and helper plasmids were fully sequenced.

SP6-HE2 mutants. Mutants were made on SP6-H plasmid following the kit QuickChange IIx site-directed mutagenesis (Stratagene, La Jolla, Calif.). Briefly, 10 ng of SP6-H#432 were incubated with complementary primers: E2-I3-F/E2-I3-R or E2-K70-F/E2-K70-R or E2-E181-F/E2-E181-R or E2-V251-F/E2-V25 1-R, reaction buffer, dNTPs and 2.5 units of pfuUltra HF DNA polymerase. PCR reactions were 95° C. 1 min, 18 cycles of: 95° C. 50 s, 60° C. 50 s, 68° C. 7 min, and final elongation of 68° C. 7 min.

After the PCR reactions 10 U of restriction enzyme DpnI was added and reaction incubated 37° C. 1 hour to digest methylated parental DNA. XL-10-Gold competent *E.coli* cells were transformed and the colonies analyzed by restriction enzyme digestion (RE). Mutations were verified by sequencing. Multiple mutants were made following the same protocol using previous mutants as template for PCR. The sequence of primers used and nt changes are shown in Table III (Appendix A). Plasmids made: SP6-H-I3#5; SP6-H-K70#59; SP6-H-I3-K70#66; SP6-H-I3H-K70-E181#3; SP6-H-K70-V251# SP6-H-I3-K70-E181-V251. In order to make sure that there were not additional mutations due to the PCR technique, the 1270 bp BssHII/BanII fragment of each clone was subcloned in the sequenced plasmid SP6-H.

Reporter gene cloning in replicon vectors. The LacZ gene was cloned in the PmlI/XbaI site of vectors SP6-ARep#701, SP6-R#406,T7-ARep#68 and T7-R#202 to generate SP6-ARepLacZ, SP6-RLacZ, T7-ARepLacZ and T7-RLacZ, respectively.

The firefly luciferase gene was excised at the NheI/XbaI sites from pGL3 plasmid (Promega Co, Madison Wis.) and cloned in the XbaI site of vectors: SP6-ARep#701, SP6-R#406,T7-ARep#68 and T7-R#202 to generate SP6-ARep-Fluc, SP6-RFluc, T7-ARepFluc and T7-RFluc, respectively.

The Renilla luciferase gene from plasmid phRL-CMV (Promega Co, Madison Wis.) was cloned in the XbaI site of the replicons, to generate plasmids: SP6-RhRluc and T7-RhRluc.

EXAMPLE 2

Cells. BHK-21, and ES-2 cells were obtained from the American Type Culture Collection (ATCC). BHK-21 cells were maintained in αMEM (JRH Bioscience) with 5% FBS. ES-2 cells were derived from a patient with clear cell carcinoma, a type of ovarian cancer that has a poor prognosis and is resistant to several chemotherapeutic agents including cisplatin. ES-2 cells were cultured in McCoy's 5A medium (Mediatech) with 5% FBS. All basal media were supplemented with 100 μg/ml of penicillin-streptomycin and 0.5 μg/ml of amphotericin B (both from Mediatech). ES-2/Fluc cells were derived from the ES-2 line by transfection of a plasmid, pIRES2-Luc/EGFP, that expresses a bicistronic mRNA transcript containing both firefly luciferase and EGFP genes. To construct the pIRES2-Luc/EGFP plasmid, a DNA fragment containing the luciferase gene was obtained from pGL-3 basic plasmid (Promega) and then subcloned into the multicloning sites of the pIRES2-EGFP plasmid (BD Biosciences Clontech).

The mouse ovarian MOSEC cell line (clone ID8) was a generous gift from Dr. Katherine F. Roby (University of Kansas Medical Center, Kansas City) and was maintained in Dulbecco's modified Eagle's medium (DMEM) supplemented with 4% FBS and 1× insulin-transferrin-selenium (Mediatech, Inc).

In vitro transcription and vector preparation. The plasmids carrying the Sindbis replicon or JT-BB helper RNAs were linearized with PacI, NotI or XhoI, before in vitro transcription using the mMESSAGE mMACHINE RNA transcription kit (T7 and SP6 version; Ambion). Both helper and replicon RNA transcripts (20 μl each) were then electroporated into BHK-21 cells and incubated in 10 ml of αMEM containing 5% FBS at 37° C. for 12 h. The medium was replaced with 9 ml of Opti-MEM I medium (GIBCO-BRL, Invitrogen San Diego Calif.) supplemented with 0.7 μM $CaCl_2$. After 24 h, the culture medium was collected and stored at −80° C.

Vector titering. The titers of Sindbis vectors were assayed in BHK-21, ES-2, ES-2/Fluc or MOSEC cells. Serial dilutions (300 μL each) of vector were added to $2\times10^5$ BHK-21 cells in 12-well plates. After incubation for 1 hour at room temperature, the cells were washed with PBS and incubated with 2 mL of αMEM at 37° C. for 24 hours.

LacZ expression was determined by two methods: staining and counting blue cells/well or reading absorbance. For the first, cells were fixed in PBS containing 0.5% glutaraldehyde at room temperature for 20 minutes, washed three times with PBS, and then stained with PBS containing 1 mg/mL X-gal (5-bromo-4-chloro-3-indolyl-D-galactopyranoside; (Fisher Scientific, Pittsburgh, Pa.), 5 mM potassium ferricyanide, 5 mM potassium ferrocyanide, and 1 mM MgSO4 at 37° C. for 3 hours. After staining with the X-Gal solution, cells that expressed LacZ were blue. Blue-stained cells were counted and vector titers were estimated by determining the number of transducing units (TU) per mL of aliquot. With the second method, cells were lysed with 200 μL of M-PER lysis buffer (Pierce Biotechnology, Rockford, Ill.). 50 μL of the cell lysates were added into 50 μL of All-in-One-Galactosidase Assay Reagent (Pierce Biotechnology) and incubated at room temperature for 5 minutes before reading at 405 nm. Vector titers were estimated as the last dilution having detectable absorbance.

Firefly luciferase activity in cell lysates was determined by aspirating the culture medium from the wells and adding 200 μL per well of culture medium and 200 μL per well of Steady-Glo™ reagent (Promega Corp., Madison, Wis.). Plates were incubated with gentle rocking for 5 minutes until the cells detached from the plates. The cell lysates were then transferred to 12×47 mm cuvettes (BD Pharmingen, San Diego, Calif.), and the luciferase activity of each lysate was determined by taking a 30-second reading with a LUMI-ONE portable luminometer (Bioscan, Inc., Washington, D.C.).

Renilla luciferase activity was determined by following the protocol in "Renilla Luciferase assay system" (Promega Corp., Madison, Wis.). Briefly, cells were washed with PBS and 250 μl/well of lysis buffer was added. 20 μL of substrate were added to 100 μL of extract and the luciferase activity of each lysate was determined by taking a 30-second reading with a LUMI-ONE portable luminometer (Bioscan, Inc., Washington, D.C.).

Animal models. All animal experiments were done in accordance with NIH and institutional guidelines. To determine the therapeutic effects of Sindbis virus vectors, SCID mice (female, 6-8 week old; Taconic, Germantown, N.Y.) were i.p. injected with $1.5\times10^6$ ES-2/Fluc cells/mouse on day 0 and imaged with the IVIS® system the next day (day 1) to confirm the presence of tumor cells. Then on day 4, 5 mice/vector received i.p. treatment with vectors carrying the Renilla luciferase: A(JT-BB/SP6-RhRluc), B (SP6-H/JT-RephRluc), C (SP6-H/SP6-RhRluc), D (JT-BB/JT-RephRluc). All vectors had the same titer in ES-2/Fluc cells, and mice were i.p. injected daily with ~$10^6$ TU in 0.5 ml Opti-MEM I/mouse. Control mice (n=5) received no Sindbis vector treatment. Disease progression was later determined by IVIS® imaging on days 1, 5, 9 and 13.

Survival curves were compared with log rank test. All the P values presented in this study are two-tailed.

For colocalization experiments, two SCID mice/vector were i.p. inoculated with $2\times10^6$ ES-2/Fluc cells on day 0 and received one i.p. treatment of vector C (~$10^6$ TU in 0.5 mL of OptiMEM I) on day 5. The next day (day 6), mice were i.p. injected with 0.3 mL of 0.2 mg/mL coelenterazine (Biotium, Inc., Hayward, Calif.) followed by IVIS® imaging for Renilla luciferase activity. 30 minutes later, the same mice were i.p. injected with 0.3 mL of 15 mg/mL D-luciferin (Biotium, Inc) and a second IVIS® imaging for Firefly luciferase activity was performed.

Cell tropism experiments, were done in two groups of SCID mice with 5 mice/vector: one without tumor induction and the second one in mice with induced tumors.

The tumor free animals were i.p. injected with Fluc vectors on day 0, imaged by IVIS® on day 1, received a second injection of vectors on day 2 and on day 3 were IVIS® imaged again.

For the second group, SCID female mice were injected i.p. on day 0 with $2\times10^6$ ES-2 cells/mouse and on day 4 mice were injected with vectors carrying the luciferase reporter genes. After the first whole-body IVIS® imaging on day 1, the peritoneum was removed for another IVIS® imaging of the peritoneal cavity. The remaining mice of the group, except one for background control, had a second i.p. injection of vectors on day 6 and imaged again on day 7.

In vivo bioluminescence detection with the IVIS® Imaging System. A cryogenically cooled IVIS® Imaging System Series 100 (Xenogen) was used with Living Image acquisition and analysis software (Version 2.11, Xenogen Corp. Alameda, Calif.) to detect the bioluminescence signals in mice. For firefly luciferase detection, each mouse was injected i.p. with 0.3 ml of 15 mg/ml beetle luciferin (potassium salt; Promega Corp., Madison, Wis.) in PBS. After 5 min, mice were anesthetized with 0.3 ml of avertin (1.25% of 2,2,2-tribromoethanol in 5% tert-amyl alcohol) or isofluran-mixed oxygen. The imaging system first took a photographic image in the chamber under dim illumination; this was followed by luminescent image acquisition. The overlay of the pseudocolor images represents the spatial distribution of photon counts produced by active luciferase. An integration time of 1 min was used for luminescent image acquisition for all mouse tumor models. Living Image software (Wave Metrics Inc., Lake Oswego, Oreg.) was used to integrate the total bioluminescence signals (in terms of proton counts) obtained from mice. The in vitro detection limit of the IVIS® Imaging System is 1,000 ES-2/Fluc cells.

Ar-339 Sequence Analysis

Ar-339 virus was amplified in chicken embryo fibroblasts and cloned into sequencing plasmids as six separate overlapping fragments (FIG. 1). CDNA-3B and CDNA-4 overlap the 312 bp fragment (nt 7334-7646) that contains the viral subgenomic promoter. In order to avoid mutations due to RT or PCR reactions, for each plasmid three different RT reactions were performed and each one served as template for one PCR reaction. The three PCR amplified bands of each fragment were cloned separately, sequenced and compared to verify the virus sequence. The Ar-339 sequence obtained was compared to the Sindbis published sequence (Strauss E G, Rice C M and Strauss J H 1984) and to the sequence of Sindbis vectors that we used previously in our laboratory, JT-BB and JT-Rep. (Tseng et al 2004a,b). The results are shown in Table IV (Appendix A). The differences in sequence between the Strauss sequence and JT vectors are described in Table V (Appendix A). Functional changes between JT and AR-339 plasmids are summarized in Table VI (Appendix A).

In the viral replicase, comparing the Strauss map with Ar-339, three point mutations in nsp1 were found: nt 353 a silent mutation; nt 1380 and 1381. Both change amino acid 441 from Cys to Ile in Ar339. In the Sindbis-like virus supergroup, the methyltransferase nsp1 has four conserved motifs I (a.a 31 to 51), II (a.a 87 to 86), III (168 to 220) and IV(243 to 260) (Rozanov et al. 1992). Cys 441 to Ile is not in the carboxyterminal domain required for enzymatic activity (K468 to L512)(Wang et al. 1996). Nsp2 has three mutations compared to the Strauss sequence, one silent at nt 3698 (A to G) and two (nt 2992 and 3579) that change amino acids 438 (Pro to Leu) and 634 (Lys to Glu) respectively. Both amino acids are outside the active helicase and protease domains of nsp2 (Rikkonen et al. 1994). Sindbis virus with Pro at 438, as described in the Strauss sequence, has lethal effects on virus replication (Rice et al. 1987). In nsp4 there was a silent mutation at nt 7337 (T to C).

Regarding the structural proteins, the Ar-339 capsid protein had two mutations compared with the Strauss sequence, one silent at nt 8345 (C to A) and one at nt 7846 that changed Pro 67 to Gln. In the consensus Strauss sequence and JT vectors a Proline occurs at position 67. This residue is conserved in different isolates of virus in Australia, and for MK6962, a New Guinea isolate, a Tyr (T) is present at this site (Sammels et al. 1999). This change is in the 11 to 74 amino acid region that doesn't bind to Sindbis RNA (Geigenmuller-Gnirke et al. 1993) and is not in E2 or capsid proteins interaction domains residues 36-39, 108 to 111, 172, 180 to 183, 201, 231-234, 240 or 254 (Katherine E. Owen and Richard J. Kuhn, 1996; H. Lee and D. T. Brown 1994).

There were also two silent mutations in E1 at nt 10392 (T to C) and 10469 (T to A) and two differences in the Ar-339 with the Strauss map were found at positions Ala 72 to Val in Ar-339 and 237 (Ser to Ala), which are both located in domain II. Residues of this domain are involved in E1-E1 interaction in the virus spike (Zhang W et al. 2002).

Most of the coding changes were found in the envelope protein E2, in which the antigenic sites and the binding receptor domain of the virus have been described. Comparing the Strauss sequence with Ar-339, five amino acid changes were found located in the external leaf-like domain of the E2 protein, which extends from the amino terminus to residue 218 (Zhang W et al. 2002). Changes are in amino acids: 3 (Ile to Thr); 23 (Val to Ala); 70 (Lys to Glu) and also two of mutations, 172 (Arg to Gly) and 181 (Glu to Lys), occur in the putative binding receptor domain (amino acids 170 to 220). No changes were found in the endodomain that interacts with the capsid protein (from 391 to 483) or with the E2-E1 interaction region.

An analysis of the amino acid changes between the JT plasmids and the Ar-339 sequence revealed only one mutation in the replicase, Cys 441 to Ile of nsp1. In the structural proteins there were a total of eight differences, only one in the capsid protein, Pro 67 to Gln; and seven in the E1 and E2 envelope proteins. Three mutations in E1: Ala 72 to Val; Gly 75 to Asp and Ser 237 to Ala. Most of the differences were found in the E2 protein, three in the leaf-Like domain; Ile 3 to Thr; Lys70 to Glu and Glu 181 to Lys and one in the ectodomain, Val 251 to Ala. V251 is important for virus maturation in CEF (Li M L et al. 1999).

Vector Constructions

To construct the Ar-339 vectors, the Sindbis genome was split into two plasmids: the replicon and the helper (FIG. 2). This vector system is designed to electroporate in vitro transcribed viral RNA into the susceptible cell line to produce replicative defective Sindbis virus, called viral vector, that contains, as a genome, the replicase RNA and lacks the structural genes. For in vitro transcription, a bacteriophage promoter is required before the viral sequence.

In order to compare the yield of viral vectors in this system, two pairs of vectors were prodced, one pair with replicon and helper under the control of the SP6 promoter (SP6-H and SP6-R), and the other pair under the control of the T7 promoter (T7-H and T7-R).

The replicon contains the viral replicase, with the packaging signal, nt 945 to nt 1075, (Weiss B et al. 1994; Frolova et al 1997); the viral subgenomic promoter, multicloning site 1 (MCS1) to allow for the insertion and expression of the gene of interest, and the 3' end of the virus (nt 11394 to 11703) to allow viral (−) strand RNA synthesis. A second multicloning site (MCS2) allows the linearization of the plasmid for in vitro transcription.

The helper plasmid contains the first 425 nt of the virus, followed by the 3' end of the virus from nt 7334 to nt 11703 which includes the subgenomic promoter, the capsid and the viral envelope proteins (E3, E2, 6K and E1) and the 3' end (nt 11394 to 11703).

Both plasmids share the following viral sequences: the first 425 nt, the 309 nt of the 3'end and the sub genomic promoter.

Both plasmids have several non-viral elements in common, the replication origin (rep pMB1) and the Ampicillin resistance gene from the pUC cloning plasmid; the promoter for in vitro transcription (T7 or SP6) and the MCS2. In the construction process a plasmid containing the pUC sequences, SP6 or T7 promoter, the multicloning sites, and the 3'viral end, which are common to both vectors, was first generated. The specific viral sequences were then cloned into this plasmid (FIG. 3).

SP6 and T7 Promoters

For in vitro transcription systems, the RNA yield using SP6 or T7 RNA polymerase for long RNA transcripts could differ. To study if the promoter would make a difference in the titer of the viral vectors production, BHK-21 cells were electroporated with two sets of in vitro transcribed RNAs: SP6-AH and SP6-ARepLacZ, to generate the SP6-LacZ viral vector, and with T7-AH and T7-ARepLacZ for the T7-LacZ vector. The comparison of both vector's titers in BHK-21 cell, in repeated experiments, gave equivalent titers≈$10^6$ transducing units (TU)/mL. In terms of infective particles production, both promoters work with the same efficiency in this system.

Sequencing of the four plasmids (SP6-AH, SP6-ARep, T7-AH and T7-ARep) revealed a deletion of one T at the 3' end of the virus before the poly A (SV nt 11686). To study the effect of this deletion on viral vectors, four new plasmids without the deletion were constructed (SP6-H, SP6-R, T7-H and T7-R) and titers of viral vectors from both sets of plasmids were compared. No significant difference was observed indicating that the deletion of T11686 is not critical for vector replication. As these four sets of vectors showed the same in vitro titer, in order to standardize results the experiments with mice were performed using SP6-H and SP6-R plasmids to synthesize viral vectors.

EXAMPLE 3

Biological Properties

Cell Tropism

Most of the amino acid differences found between JT and Ar-339 vectors were in the envelope proteins. One of them was related to virus adaptation to BHK-21, E2 Lys 70 to Glu (McNight K et al, 1996) and two of them were located in the receptor-binding domain of the E2 protein. To analyze if the amino acid changes had any effect on the viral vector's infectivity, JT, Ar-339 and chimeric viral vectors were produced and titered in three cell lines: BHK-21 (baby hamster kidney), ES-2 and Mosec human and mouse ovarian cancer cell lines respectively. The results are shown in Table VII (Appendix A). Vectors that carry JT-BB helper (JT-BB/SP6-ARepLacZ and JT-BB/JT-RepLacZ) had titers two logarithms higher in BHK-21 than in the other two cell lines; when the helper was SP6-H, the difference observed was only one log. The infectivity of the vectors in vitro was similar in both ovarian cancer cell lines, ES-2 and Mosec. This difference was observed in repeated experiments.

Disease Progression

In order to compare the ability in targeting and suppression of disease progression by Sindbis vectors Ar-339 and JT, JT and Ar-339 chimeric vectors were produced and tested in the ES-2/Fluc mouse metastatic ovarian cancer model described previously (Tseng et al. 2004b). Five female SCID mice per vector group were injected i.p. with $1.5\times10^6$ ES-2/Fluc cells (day 0) and IVIS® imaged the next day to verify the presence of ES-2/Fluc cells. Cells were left to grow for four days before daily treatment with vectors was started. There were five mouse groups, one of which did not receive vector treatment, whereas the remaining 4 had vectors: A(JT-BB/SP6-RhRluc), B (SP6-H/JT-RephRluc), C (SP6-H/SP6-RhRluc) and D (JT-BB/JT-RephRluc). As these strains showed different cell tropism in BHK-21 cells, vectors were titered in the same cell line used to induce the tumor ES-2/Fluc, and titers for all vectors were standardized at $10^6$ TU/mL. Total whole body photon counts were determined by IVIS® imaging on days 1, 5, 13, and 19 to determine disease progression of ES-2/Fluc metastases (FIG. 4). Survival curves were also compared (FIG. 5).

Vector A, carrying the Ar-339 replicase (SP6-RhRluc) and JT structural proteins was more efficient in reducing tumor progression and gave better survival of the animals. The vectors carrying the same structural proteins, vector B versus C and A versus D were compared. In both cases there was more tumor reduction with Ar-339 replicase (SP6-RhRluc). Regarding the structural part, when the vectors carrying the same replicase were analyzed, in one case SP6-H seemed to be more effective (Vectors D versus B), but in the case of A versus C, where the photon count difference is larger, JT-BB is more efficient in tumor targeting. The small differences between vectors B, C and D correlates with similar animal survival data, although both structural proteins and replicase function in the efficiency of the vectors in vivo, these data suggest that an improvement in the targeting of Ar-339 replicase (SP6-R) to tumor cells would lead to more efficient gene therapy vectors.

Co-Localization

Figure 6A:
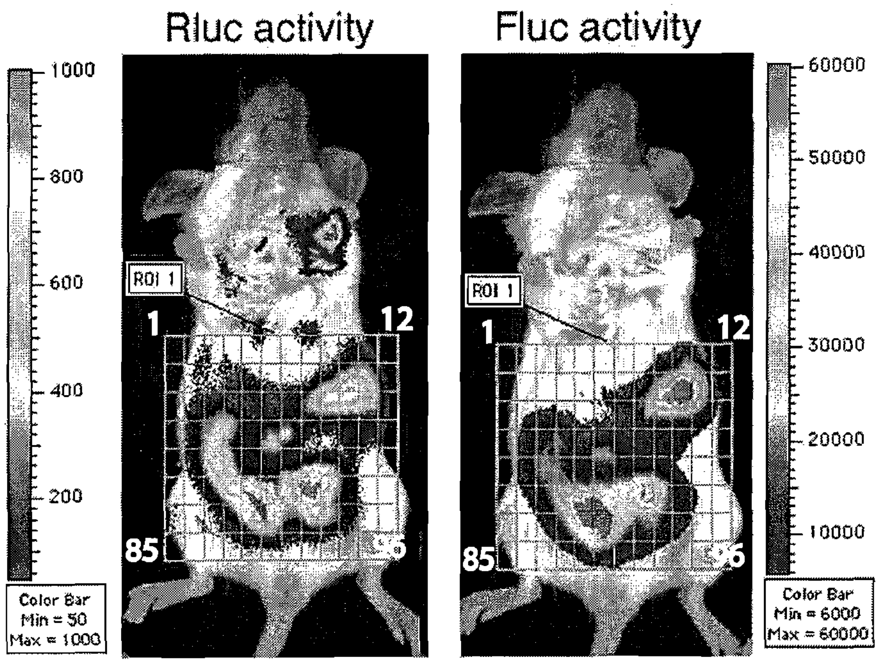
Figure 6B:
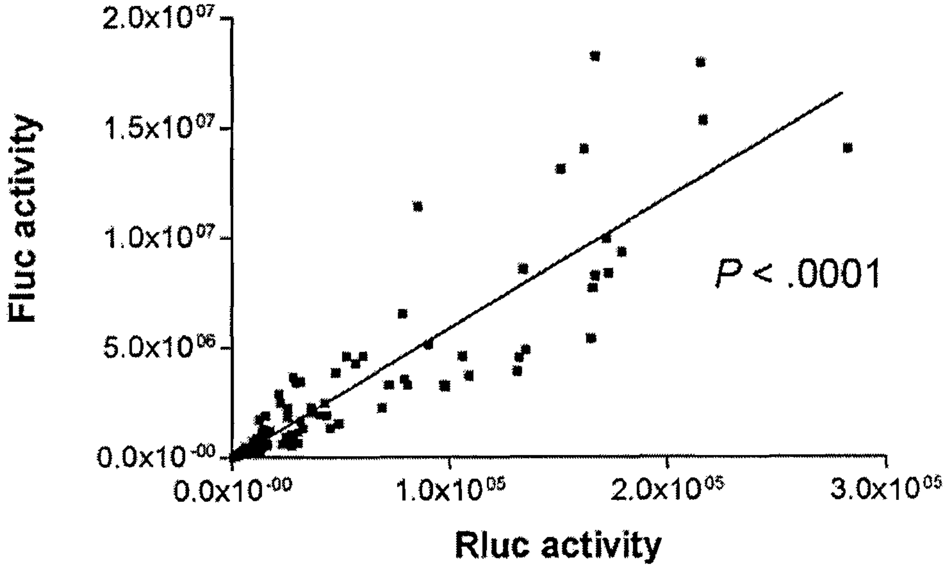

To establish the degree and specificity of Ar-339 Sindbis infection of tumor cells, IVIS® imaging studies were performed that measured independent bioluminescent signals from tumor cells and vectors. The ES-2/Fluc cells expressed the firefly luciferase gene, that uses D-luciferin as substrate, and the vectors carried a different luciferase gene cloned from soft coral *Renilla renifomis* (Rluc) that uses coelenterazine to generate bioluminescence. The two luciferases are highly substrate specific and do not cross-react (Bhaumik S and Gambhir S S. 2002). Each anesthetized mouse was first treated with coelenterazine the image was collected (FIG. 6A, left panel), then treated with D-luciferin for a second IVIS® imaging, this time of ES-2/Fluc cells (FIG. 6A right panel). The bioluminescence signals generated in the same animal from Sindbis/Rluc and ES-2/Fluc, were quantitated using Living Image software. The images of Rluc and Fluc signals were grided (12 8, 96 boxed regions), and corresponding regions were analyzed for statistical correlation (FIG. 6B). A highly significant correlation was established ($P<0.0001$) indicating that a single i.p. delivery of Ar-339 Sindbis vector lead to the efficient infection of the metastasized tumor cells throughout the peritoneal cavity. In several mice an additional infection outside the peritoneal cavity was observed.

Ar-339 Targeting

Figure 7A:
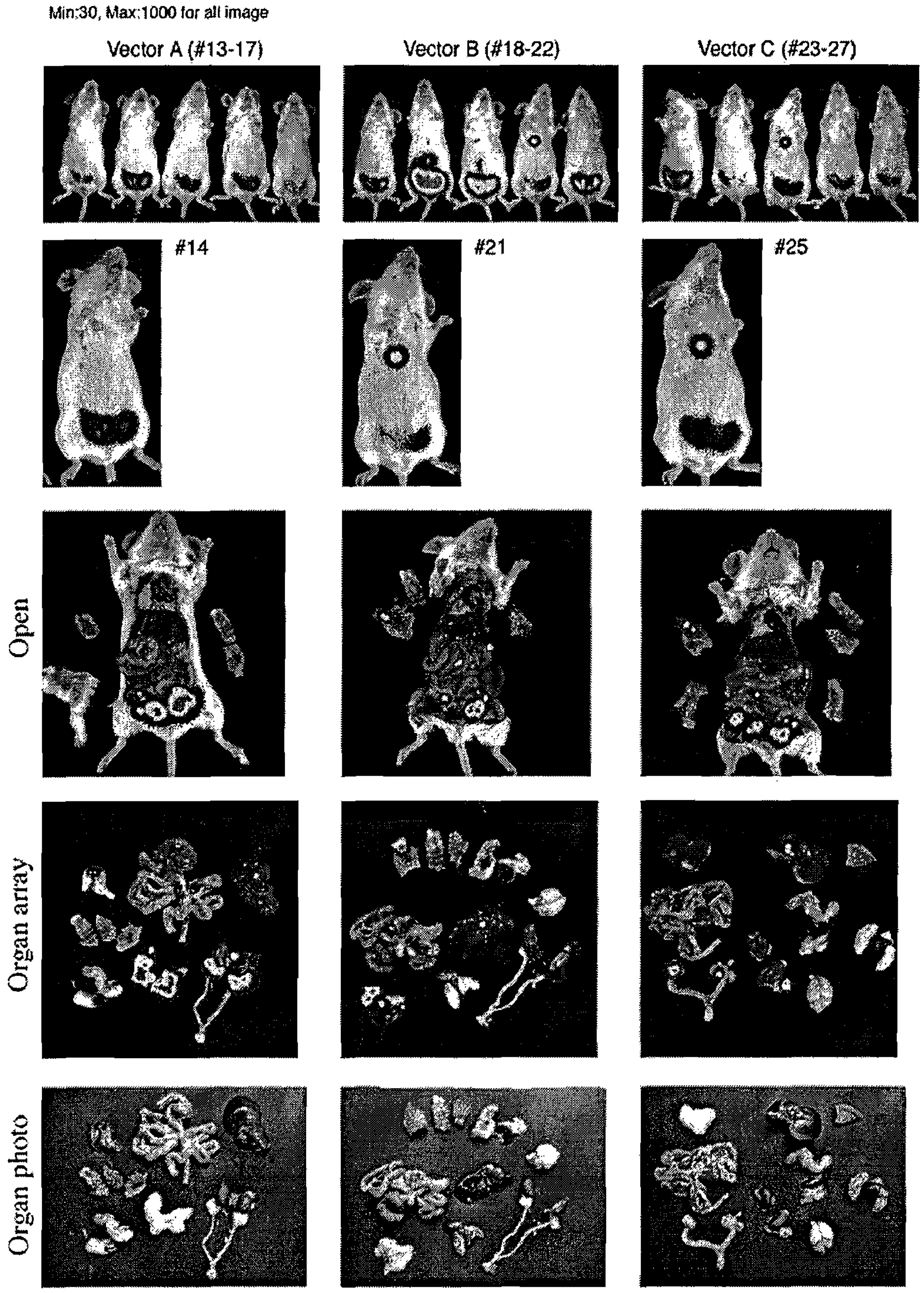
Figure 7B:
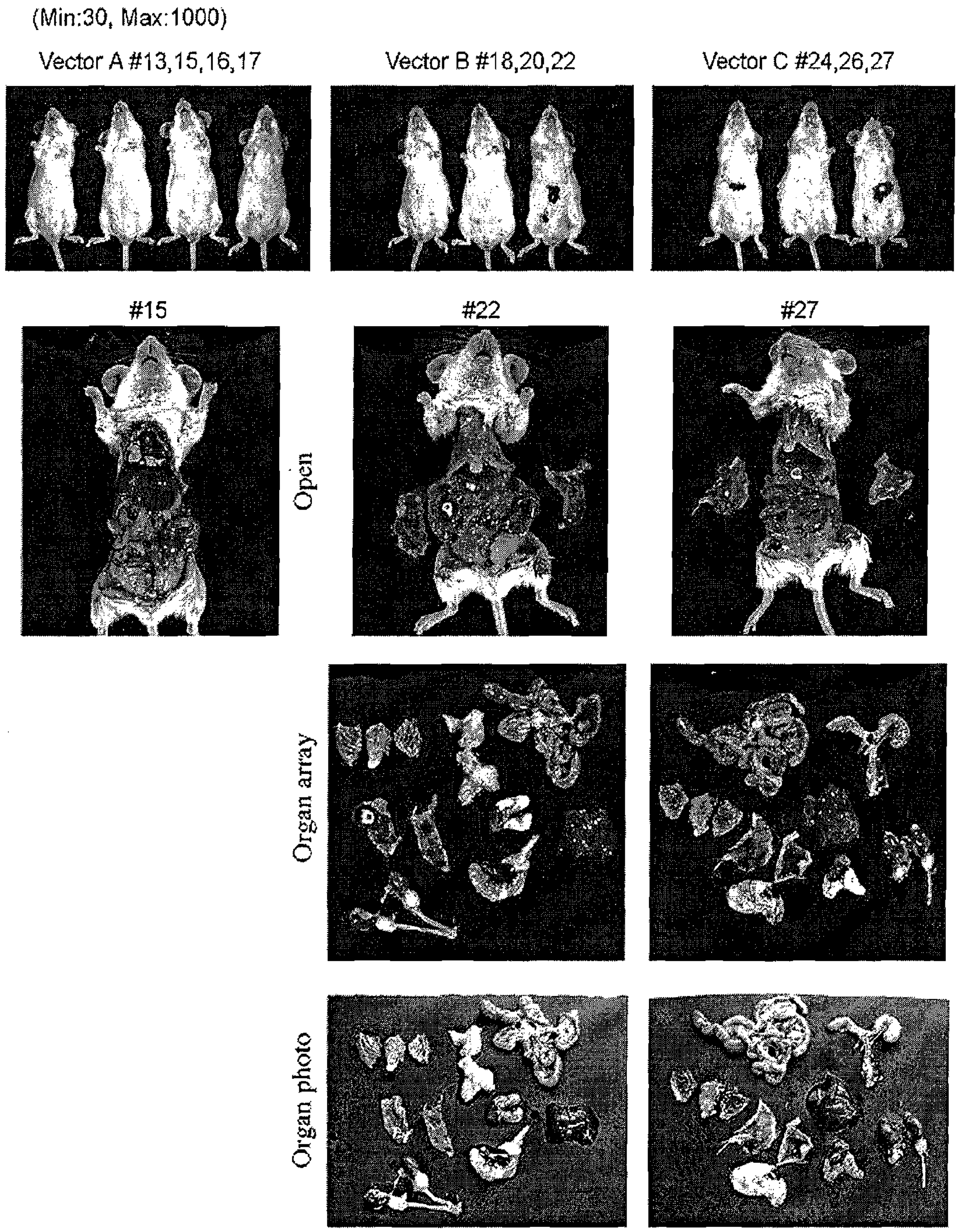

To analyze tissues or organs targeted by the Ar-339 strain, new chimeric vectors were made with firefly luciferase (Fluc) as the reporter gene, since its stronger bioluminescent signal allows the study of vectors in animal organs. Each vector was tested in two groups of 5 SCID female mice: tumor-free and 5 day ES-2 metastasis induced mice. To assess which part of the C vector was responsible for the chest bioluminiscence, three Fluc chimeric vectors were made: A(JT-BB/SP6-RFluc), B(SP6-H/JT-RepFluc) and C (JT-BB/JT-RepFluc). As previously, vectors were titered in ES-2 cells. Tumor free mice received one dose of vector ($10^4$ TU/mL) at day 0 and were IVIS® imaged next day (FIG. 7A). All three groups showed a low background signal in fat tissue. Two out of five vector B mice and one of five mice in vector C group showed some additional bioluminescent signal in the chest, as previously observed in the colocalization experiment. To investigate if vectors were infecting organs in these mice, intraperitoneal cavity and harvested organs were also IVIS® imaged. The chest signal observed corresponded to connective tissue in the ribs, while organs had no background signal. To study if repeated doses of these vectors could lead to accumulative infection in tumor-free mice, a second dose was i.p. injected on day 2 and the image repeated on day 3. The results (FIG. 7B) showed low background signal in fat tissue for vectors B and C and no signal at all for vector A, indicating that the background is transient and shouldn't affect the target effectiveness of Ar-339 vectors in repeated treatment.

Figure 8A:
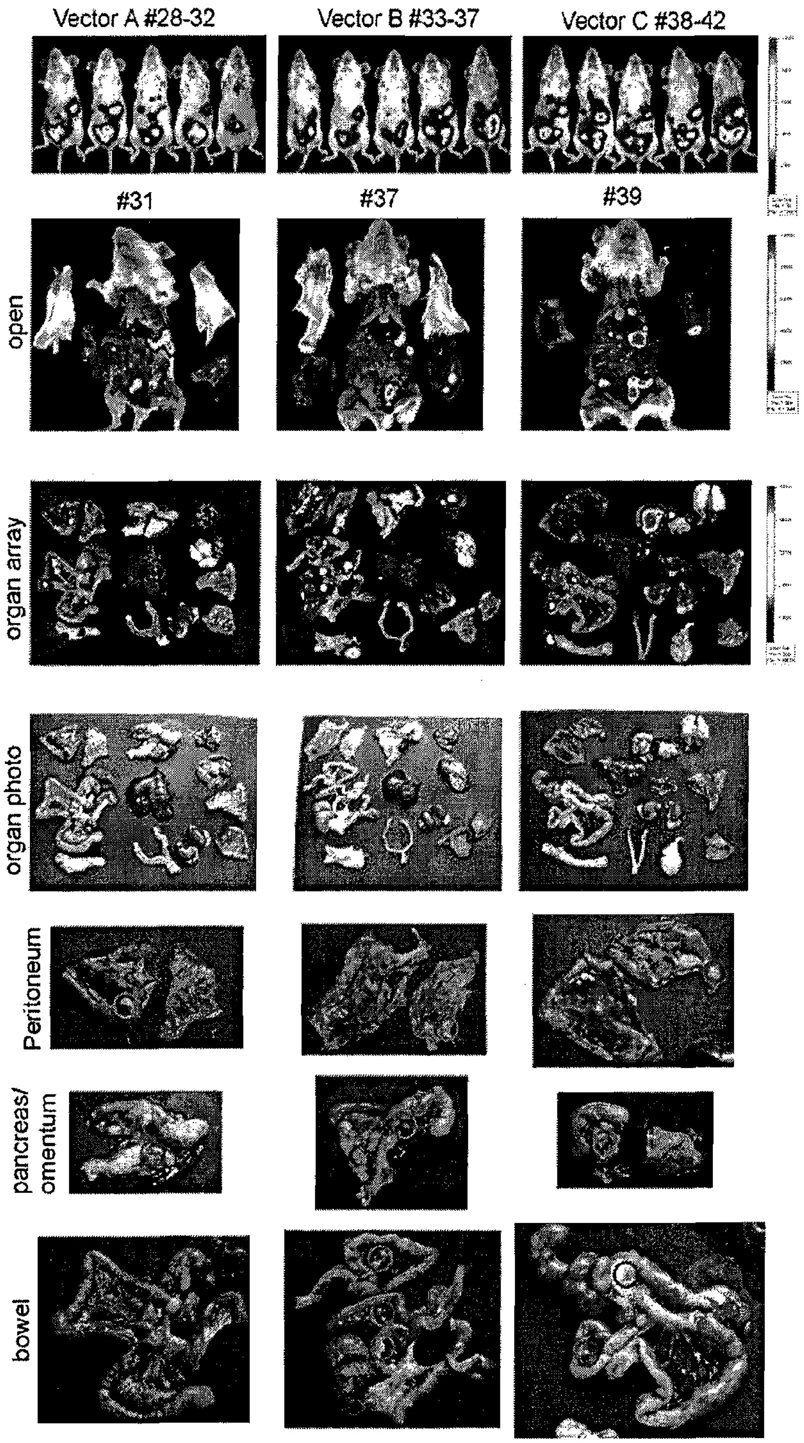
Figure 8B:
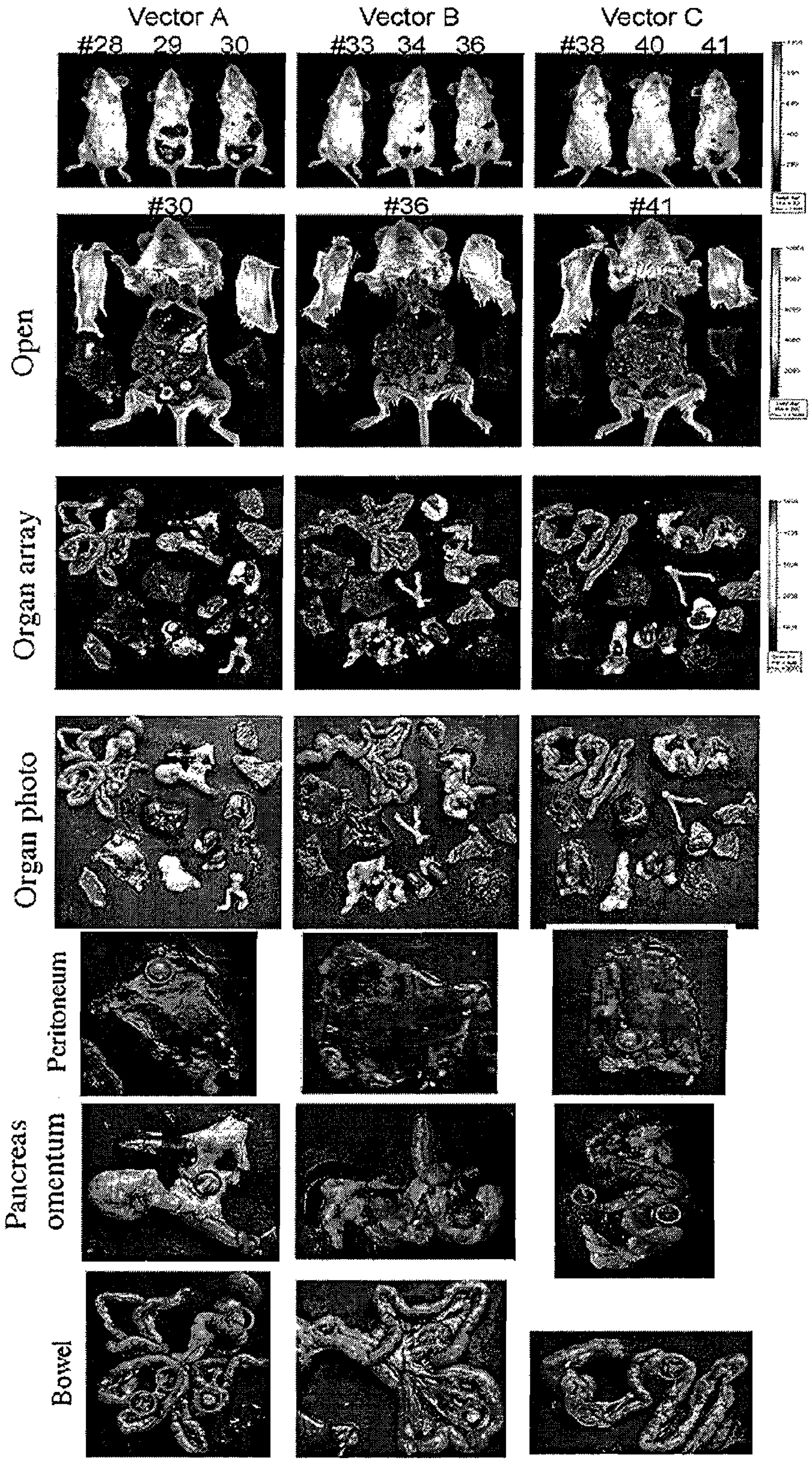
Figure 9A:
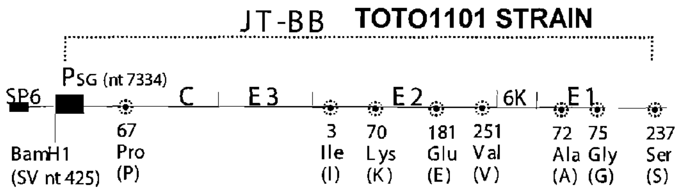
Figure 9B:
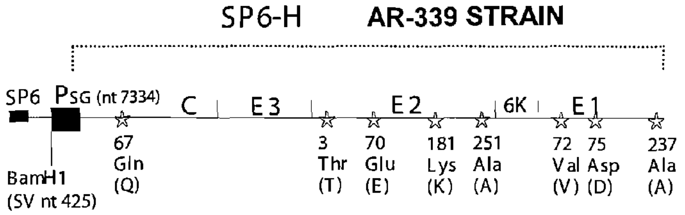
Figure 9C:
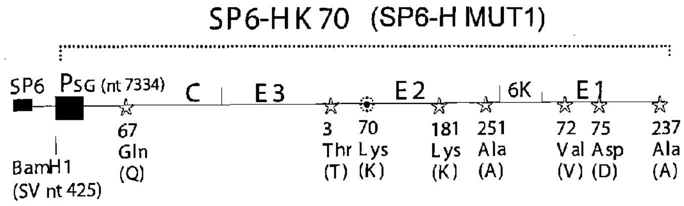
Figure 9D:
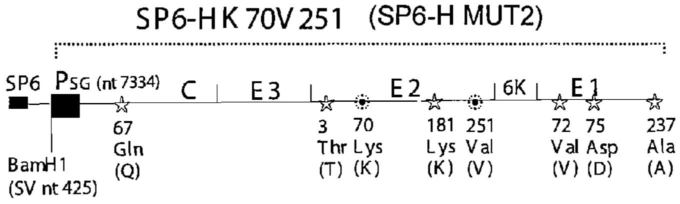
Figure 9E:
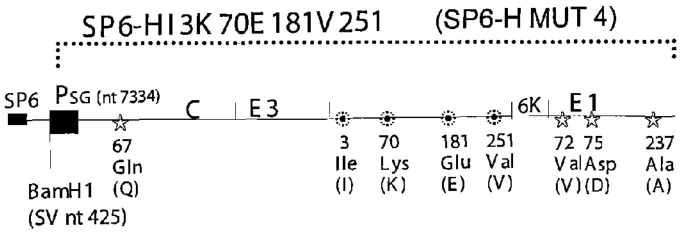

Previous studies of JT/Fluc vector in 5 day ES-2 tumor induced mice, showed that the vector specifically targets metastasized ES-2 cells after one injection and also in a second dose two days later (Tseng et al. 2004). To study if the difference between sequences could affect the specificity of Ar-339 vector, these 3 chimeric vectors were tested in the same model. Mice injected with $2\times10^6$ ES-2 cells on day 0, received one i.p. dose of vectors on day 5 and were IVIS® imaged on day 6. The peritoneal cavity and organs of two mice per group were imaged. As is shown in FIG. 8A for all vectors, bioluminescence correlated with ES-2 metastatic implants. At day 7 two mice per group received a second i.p. dose of vector and one mouse was not injected to serve as a luciferase background signal control (FIG. 8B). Vector A showed a similar signal compared with previous doses, but vectors carrying Ar-339 structural proteins, B and C, showed decreased bioluminescence signals in tumors compared with the first injection. The difference in reinfection suggests that amino acid changes in structural proteins could play an important role in targeting metastases by repetitive treatment with vector.

In order to determine which mutations were critical for the vector properties, a chimeric vector was generated, QE2, that contains E2 from JT-BB and the remaining structural proteins from Ar-339. When we compared with Ar-339 vector in the same IVIS® animal model as in the previous experiment, in tumor free animals, a low background in fat tissue with the first dose was observed and no signal in a second dose. In ES-2 5 day induced tumor mice, vector QE2 targeted tumor and was able to re-infect animals, though the bioluminescent signal was not as strong as for Ar-339 vector (data not shown). This indicates that Ar-339 sequence in the E2 envelope protein was primarily responsible for the targeting pattern, though the optimal amino acid pattern was still not clear. To address this question site directed mutagenesis was performed on the Ar-339 E2 envelope protein.

E2 Mutants

The E2 envelope has been described as the protein that is primarily responsible for cell tropism and infectivity of Sindbis virus. More specifically, Lys 70 is implicated in BHK-21 specificity (McNight K et al, 1996) and also residues 69 to 72 have been related to targeting vertebrate cells (Ohno K et al. 1997; Dubuisson J and Rice C M, 1993). As the Ar-339 strain has a Glu in this position, 3 point mutants were generated that contain Lys at position 70 (FIG. 9). In Mut-1 only Ar-339 Glu 70 was changed to Lys. Amino acid 251 of E2 is highly conserved between different Sindbis isolates (Sammels L M et al. 1999) and mutation to Valine at this position has been related with host range phenotype (Li M L et al. 1999). To explore the influence of this amino acid in vector targeting, Mut-2 was produced that has Lys70 and also Ar-339 Ala 251 mutated to Val. Residues at positions 3 and 181 are located in the external leaf-like domain of the E2 protein and 181 is in the receptor binding domain. To assess if the combination of these 4 amino acid changes in the E2 is responsible for the difference in infection of Ar-339 vectors, mutant Mut-4 was produced with Lys 70, and Val 251 plus changes in Ar-339 Thr 3 to Ile and Ar-339 Lys 181 to Glu (FIG. 9). The mutants were tested in tumor-free and ES-2 5 day induced tumor mice as previously described for vectors A, B and C. To assure that the difference in signals were due to the E2 mutations, all five vectors tested carried the same replicase SP6-RFluc: vector A (JT-BB/SP6-RFluc), C (SP6-H/SP6-RFluc), Mut-1 (SP6-H-K70/SP6-RFluc) Mut-2 (SP6-H-K70-V251/SP6-RFluc) and Mut-4 (SP6-H-I3-K70-E181-V251/SP6-RFluc).

Vectors were titered in BHK-21 cells and in ovarian cell lines ES-2 and Mosec (Table VIII (Appendix A)). Mutants showed a greater difference between A and C when titered in BHK-21 than in ovarian cell lines.

Figure 10A:
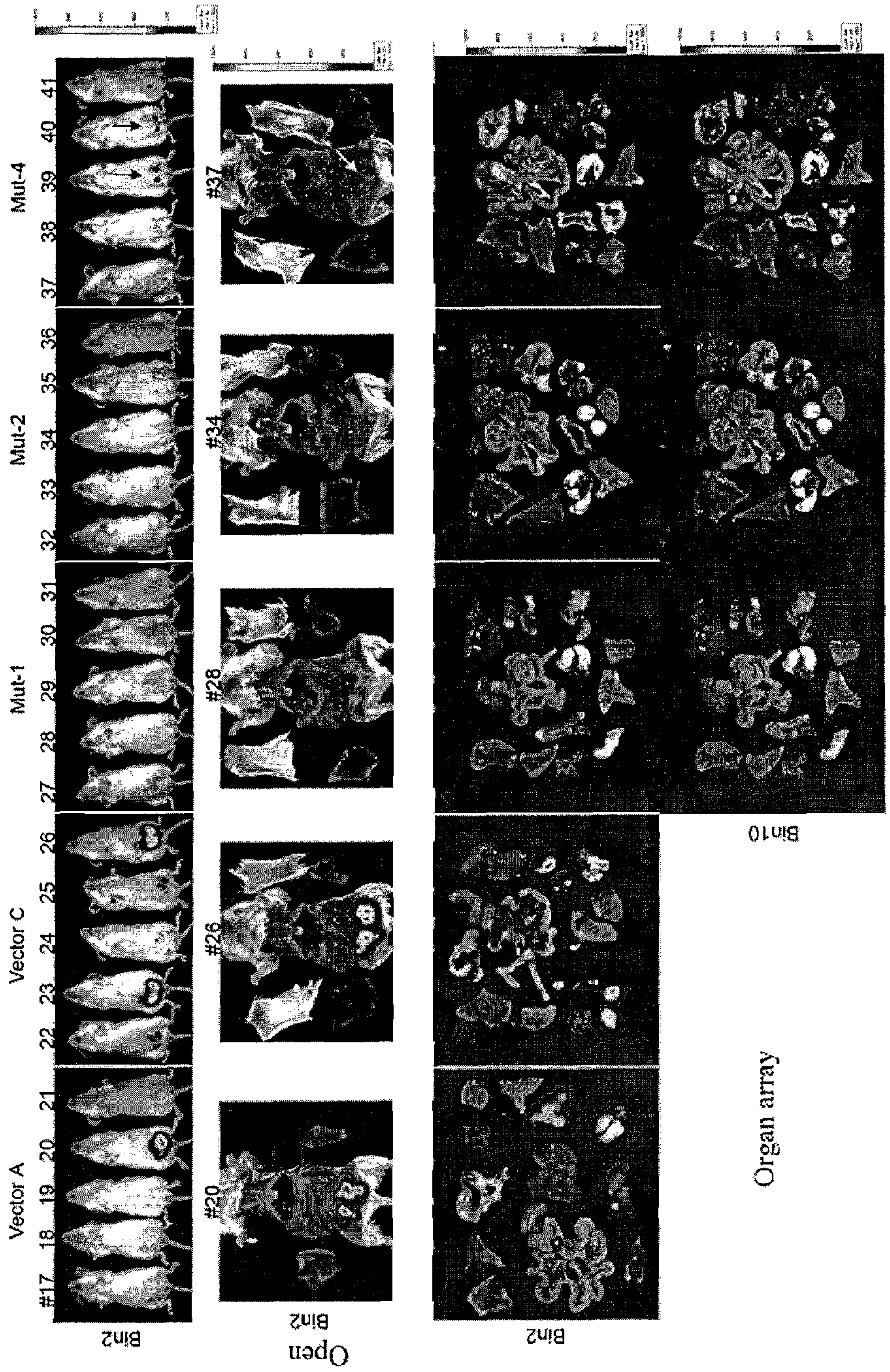
Figure 10B:
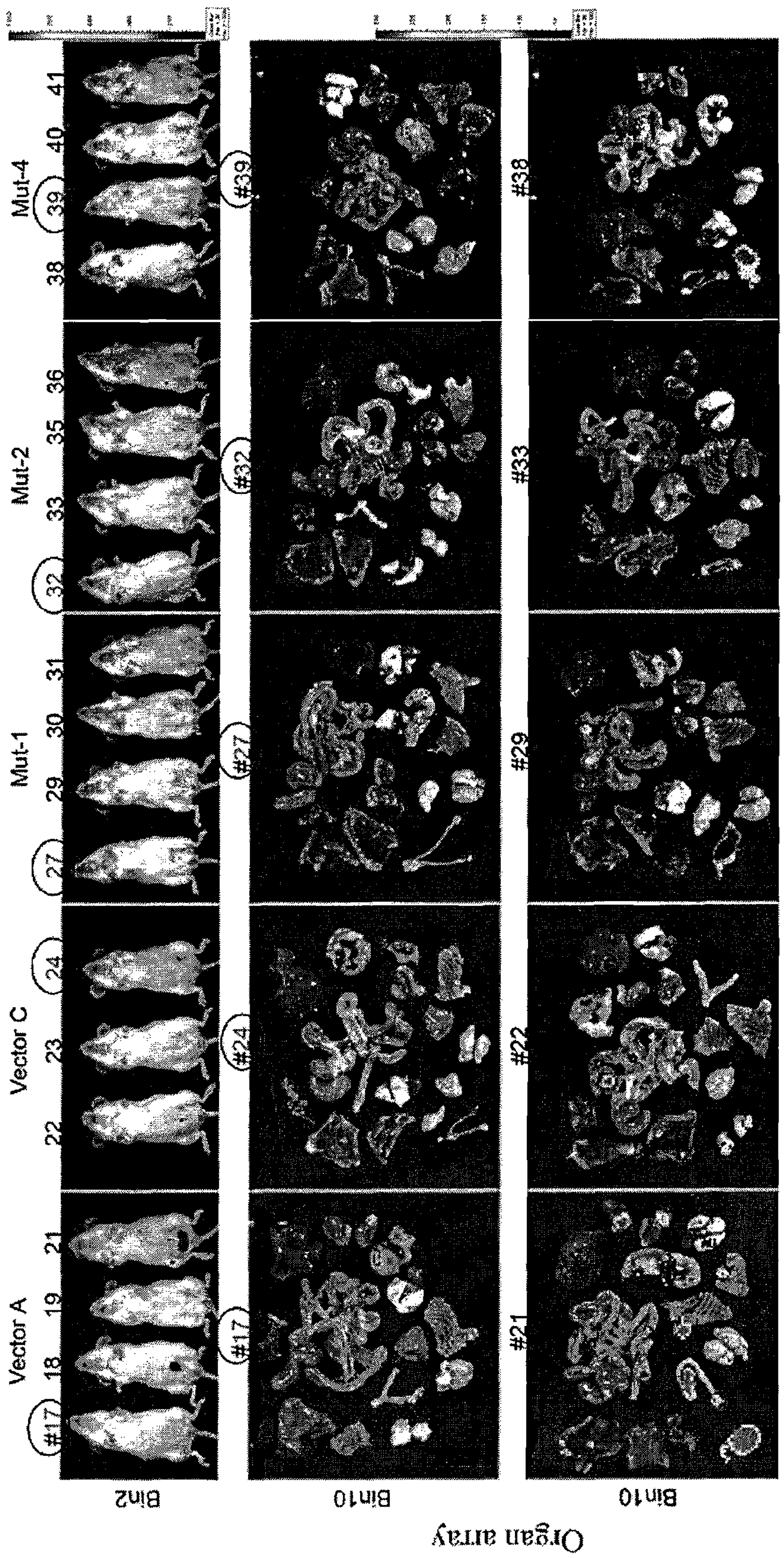

In tumor-free mice vectors A and C gave background in some of the animals. Only one out of the five vector C mice showed a low bioluminescent signal in the ribs (FIG. 10A). In second doses of these vectors the background was even less noticeable (FIG. 10B). Mut-1 and Mut-2 did not produce background bioluminescent signal in either dose. Mut-4 showed barely detectable signal in fat tissue, much less intense than vectors A and C.

In ES-2 tumor induced mice (FIG. 11A) mice #79 in A and #88 in C vector groups did not show bioluminescence; these mice did not develop ES-2 metastatic implants in the peritoneal cavity (these mice are not shown in the Figure).

This result showed a dramatic decrease in the infectivity of mutants Mut-1 and Mut-2 and an important reduction in Mut-4 after the first and second dose (FIG. 11). The change of only one amino acid in Ar-339 E2 at position 70 makes vector C lose the specificity in targeting ES-2 tumor metastases in vivo. The double mutant with Valine at position 251, Mut-2, doesn't revert the vector tropism. Mut-4 combines vector A E2 with Ar-339 E1, E3 and capsid sequences. The fact that Mut-4 could not revert to fall infectivity indicates that the interaction between E2 and E1 in the vector spike could also play an important role in vector targeting.

EXAMPLE 4

Suppression of Disease Progression by Ar-339, Mut-4 and JT Vectors

In previous mouse experiments Vector C showed background infections in some of the animals treated. Although this effect was transient and vector C was efficient in suppression of disease progression, it would be preferable for gene therapy to use a viral vector that does not cause background tissue infections. In tumor targeting experiments of SP6-HE2 mutants, vector Mut-4 showed tumor targeting although with less intensity than vector C (FIG. 11) and did not show background infection (compare FIG. 10A and 10B). With the aim of improving this vector system, the ability of Mut-4 in tumor reduction was studied and vector-tumor colocalization analyzed, using the same model described for vectors A, B, C and D as in previous experiments.

Materials and Methods

Animal models. All animal experiments were done in accordance with NIH and institutional guidelines. To determine the therapeutic effects of Sindbis virus vectors, SCID mice (female, 6-8 week old; Taconic, Germantown, N.Y.) were i.p. injected with $1.5\times10^6$ ES-2/Fluc cells/mouse on day 0 and imaged with the IVIS® system the next day (day 1) to confirm the presence of tumor cells. Then on day 4, 10 mice/vector received i.p. treatment with vectors carrying the *Renilla luciferase*: Mut-4 (SP6-HI3K70E181V251/SP6-RHRluc), C (SP6-H/SP6-RhRluc) and D (JT-BB/JT-RephR-luc). All vectors had the same titer in ES-2/Fluc cells, and mice were i.p. injected daily with $\sim10^6$ TU in 0.5 ml Opti-MEM I/mouse. Control mice (n=5) received no Sindbis vector treatment. Disease progression was later determined by IVIS® imaging on days 1, 5, 9 and 13.

Survival curves were compared with log rank test. All the P values presented in this study are two-tailed.

For colocalization experiments, two SCID mice/vector were i.p. inoculated with $1.5\times10^6$ ES-2/Fluc cells on day 0 and received one i.p. treatment of vector Mut-4 ($\sim10^6$ TU in 0.5 mL of OptiMEM I) on day 5. The next day (day 6), mice were i.p. injected with 0.3 mL of 0.2 mg/mL coelenterazine (Biotium, Inc., Hayward, Calif.) followed by IVIS® imaging for *Renilla luciferase* activity. 30 minutes later, the same mice were i.p. injected with 0.3 mL of 15 mg/mL D-luciferin (Biotium, Inc) and a second IVIS® imaging for Firefly luciferase activity was performed.

Results

Colocalization. To measure the degree and specificity of Mut-4 Sindbis infection of tumor cells, IVIS® imaging studies were performed that measured independent bioluminescent signals from tumor cells and vector Mut-4 (SP6-HI3K70E181V251/SP6-RhRluc). The ES-2/Fluc cells expressed the Firefly luciferase gene, that uses D-luciferin as a substrate, and the vector carried a different luciferase gene cloned from soft coral *Renilla renifomis* (hRluc) that uses coelenterazine to generate bioluminescence. The two luciferases are highly substrate specific and do not cross-react (Bhaumik, S. and Gambhir, S. S. 2002). Each anesthetized mouse was first treated with coelenterazine and the image was collected (FIG. 12A, left panel), then treated with D-luciferin for sequential IVIS® imaging of ES-2/Fluc cells (FIG. 12A, right panel). The bioluminescence signals generated in the same animal from vector and ES-2/Fluc were quantitated using Living Image software. The images of Rluc and Fluc signals were grided (12×8, 96 boxed regions), and the corresponding regions were analyzed for statistical correlation (FIG. 12B). A highly significant correlation was established ($P<0.0001$) indicating that a single i.p. delivery of Mut-4 Sindbis vector leads to very efficient infection of the metastasized tumor cells throughout the peritoneal cavity.

Disease progression. In order to compare the ability of Sindbis vectors Ar-339 and Mut-4 in targeting and suppression of disease, vectors were constructed and tested in the ES-2/Fluc mouse metastatic ovarian cancer model described previously. Ten female SCID mice per vector group were injected i.p. with $1.5\times10^6$ ES-2/Fluc cells (day 0) and IVIS® imaged the next day to verify the presence of ES-2/Fluc cells in the mice. Cells were left to grow for four days before daily treatment with vectors was started. There were four groups of animals, one of which did not receive vector treatment, the remaining 4 were injected daily with $10^6$ TU/ml doses of vectors carrying Renilla luciferase reporter gene: C (SP6-H/SP6-RhRluc), Mut-4 (SP6-HI3K70E181V251/SP6-RhRluc). and D (JT-BB/JT-RephRluc).

Total whole body photon counts were determined by IVIS® imaging on days 1, 5, 13, and 19 to determine disease progression of ES-2/Fluc metastases. Survival curves were also compared (FIG. 13). Mice treated with vectors C and Mut-4 showed similar photo count reduction and survival proportions. These data suggest that vector Mut-4 (SP6-HI3K70E181V251/SP6-RHRluc) has similar in vivo efficiency in tumor reduction as vector C (SP6-H/SP6-RhRluc) and so can also be used in gene therapy. Both vectors, C and Mut-4, showed significantly improved tumor reduction and mouse survival compared to vector D.

PAPER EXAMPLE 1

Production of C6/36 Packaging Cell Line with Rederived Ar-339 Plasmids

Plasmids SP6-H and SP6-R can be used to engineer insect plasmids to generate a mosquito C6/36-derived packaging cell line producing Ar-339 Sindbis vectors. Three plasmids with the Opal2 mosquito promoter (described in Theilmann et al., J. Virology, 1995, 69(12):7775-7781) are required to constitutively express viral sequences in mosquito cells. The replicon plasmid (pIZ-Ar339-R) will have the replicase, subgenomic promoter and gene of interest and the other two will contain the split helper sequences, one with capsid protein only (PIB-Ar339-C) and the second one with E1, E2, E3 and K6 envelope proteins (pIZ-Ar339-H). In a first step the C6/36 cell line (available from the American Type Culture Collection, ATCC, Manassas, Va. as ATCC CRL 1660) will be transfected with replicon plasmid (pIZ-Ar339-R) and clones will be selected. In a second step the previous clones containing the replicon will be transfected with the capsid plasmid (PIB-Ar339-C) and replicon and capsid positive clones selected. In the last step, the 2$^{nd}$ helper plasmid (pIZ-Ar339-H) will be transfected into the previously isolated clones to generate the packaging cell line that express all three plasmids.

1.—Cloning of SP6-R Rreplicase into PIZ/V5-His Plasmid

In order to clone the Ar-339 replicase in PIZ/V5-His (Invitrogen, San Diego, Calif.) it is necessary to introduce a SacI RE site before the SP6 promoter.

1.1—PCR Reactions will be performed on SP6-R#406 plasmid using primers SacI_SP6F/cDNA-1R, and then the 2340 bp band will be cloned in pcr4blunt_topo vector (Invitrogen, San Diego, Calif.). The new plasmids TOPO-Rep1

Primer Sequences:

```
SacI_SP6F GGCTAGAGCTCATTTAGGTGACA (SacI)

cDNA-1R GTAACAAGATCTCGTGCCGTGACA
```

1.2.—The SP6-R#406 plasmid will be digested with BglII/NotI and cloned the 5776 bp band into BglII/NotI TOPO-Rep1 to make new plasmid TOPO-Ar339-R 1.3.—The 8085 bp SacI/NotI TOPO-Ar339-R band will be cloned into SacI/NotI PIZ/V5-His to generate pIZ-Ar339-R. 2.—Cloning of Ar-339 Helper P In order to minimize the presence of recombinant replicative competent virus, the helper genome will be split into two plasmids: PIB-Ar339-C and pIZ-Ar339-H.

2.1 Construction of pIB-Ar339-C

The Ar-339 Capsid DNA sequence will be cloned into pIB-V5-His (Invitrogen, San Diego, Calif.) at the BamHI/SpeI site of the vector. PCR will be performed on plasmid SP6-H#432 using primers C1-F and C1-R to obtain the Ar-339 capsid 1133bp DNA band.

```
C1-F GGA TCT CCG GAT CCC CTG AAA AGG (BamHI)

C1-R GTG ACC AGT GGA CTA GTG GAC CAC TCT TC (SpeI)
```

The band will be digested and cloned into the pIB-V5-His vector at the BamHI/SpeI site to make the new plasmid pIB-Ar-339-C.

2.2 Construction of pIZ-Ar339-H

The first step is to clone the 5' end of Ar-339 (from nt 425 to 692) into pIZ/V5-His. PCR reactions will be performed on SP6 #432 plasmid with primers 416B-F and 676NB-R.

Restriction sites will be included in this no coding sequence to allow further cloning of helper sequence.

```
416B-F
GGA TCT CCG GAT CCC CTG AAA AGG CTG T (BamHI)

676NB-R
GAT GAA AGG ATC CTC GCG AAC TAT TTA GGA CCA CCG
(BamHI/NruI)
```

The 296 bp band will be digested with BamHI and cloned in the BamHI site of pIZ/V5-His to make pIZ-5END plasmid.

In a second step SP6-H#432 plasmid will be digested with NruI and XhoI and the 3435 bp band will be cloned into the NruI/XhoI site of the pIZ-5END plasmid.

REFERENCES

Bhaumik S, Gambhir S S. Optical imaging of *Renilla luciferase* reporter gene expression in living mice. Proc Natl Acad Sci USA 2002; 99:377-82.

Burge B W, Pfefferkorn E R. "Complementation between temperature-sensitive mutants of Sindbis virus". Virology. 1966 October; 30(2):214-23.

Dubuisson J, Rice C M. "Sindbis virus attachment: isolation and characterization of mutants with impaired binding to vertebrate cells." J Virol. 1993 June; 67(6):3363-74.

Frolova E, Frolov I, Schlesinger S. "Packaging signals in alphaviruses." J Virol. 1997 January; 71(1):248-58.

Frothingham (1955). "Tissue culture applied to the study of Sindbis virus." Am. J. Trop. Med. Hyg. 4: 863-871.

Geigenmuller-Gnirke U, Nitschko H, Schlesinger S. "Deletion analysis of the capsid protein of Sindbis virus: identification of the RNA binding region." J Virol. 1993 March; 67(3):1620-6.

Hurlbut, H. S. (1953). "The experimental transmission of coxsackie-like viruses by mosquitoes." J. Egypt. Med. Assoc. 36: 495-498.

Lee H, Brown D T. "Mutations in an exposed domain of Sindbis virus capsid protein result in the production of noninfectious virions and morphological variants." Virology. 1994 July; 202(1):390-400.

Levy-Mintz P, Kielian M. "Mutagenesis of the putative fusion domain of the Semliki Forest virus spike protein." J Virol. 1991 August; 65(8):4292-300.

Li M L, Liao H J, Simon L D, Stollar V. "An amino acid change in the exodomain of the E2 protein of Sindbis virus, which impairs the release of virus from chicken cells but not from mosquito cells." Virology. 1999 Nov. 10; 264(1):187-94.

McKnight K L, Simpson D A, Lin S C, Knott T A, Polo J M, Pence D F, Johannsen D B, Heidner H W, Davis N L, Johnston R E. "Deduced consensus sequence of Sindbis virus strain AR339: mutations contained in laboratory strains which affect cell culture and in vivo phenotypes." J Virol. 1996 March; 70(3):1981-9.

Myles K M, Pierro D J, Olson K E. "Deletions in the putative cell receptor-binding domain of Sindbis virus strain MRE16 E2 glycoprotein reduce midgut infectivity in Aedes aegypti." J Virol. 2003 August; 77(16):8872-81.

Ohno K, Sawai K, Iijima Y, Levin B, Meruelo D. "Cell-specific targeting of Sindbis virus vectors displaying IgG-binding domains of protein A". Nat Biotechnol. 1997 August; 15(8):763-7.

Owen K. E. and. Kuhn. R. J. "Identification of a region in the Sindbis virus nucleocapsid protein that is involved in specificity of RNA encapsidation". J. of Virology, May 1996, p2757-2763.

Rice C M, Levis R, Strauss J H, Huang H V "Production of infectious RNA transcripts from Sindbis virus cDNA clones: mapping of lethal mutations, rescue of a temperature-sensitive marker, and in vitro mutagenesis to generate defined mutants." J Virol. 1987 December; 61(12):3809-19.

Rikkonen M, Peranen J, Kaariainen L. "ATPase and GTPase activities associated with Semliki Forest virus nonstructural protein nsP2." J Virol. 1994 September; 68(9): 5804-10.

Rozanov M N, Koonin E V, Gorbalenya A E. "Conservation of the putative methyltransferase domain: a hallmark of the 'Sindbis-like' supergroup of positive-strand RNA viruses." J Gen Virol. 1992 August; 73 (Pt 8):2129-34.

Sammels L M, Lindsay M D, Poidinger M, Coelen R J, Mackenzie J S. "Geographic distribution and evolution of Sindbis virus in Australia." J GenVirol. 1999 March; 80 (Pt 3):739-48.

Strauss E G, Rice C M, Strauss J H. "Complete nucleotide sequence of the genomic RNA of Sindbis virus." Virology. 1984 February; 133(1):92-110.

Strauss, J. H. and Strauss, E. G. "The alphaviruses: gene expression, replication, and evolution" Microbiol Rev. 1994 September; 58(3): 491-562.

Taylor, R M and H S Hurlbut (1953). "Isolation of coxsackie-like viruses from mosquitoes." J. Egypt. Med. Assoc. 36: 489-494.

Taylor, R M, H S Hurlbut, T H Work, J R Kingsbury and T E Frothingham (1955). "Sindbis virus: A newly recognized arthropod-transmitted virus." Am. J. Trop. Med. Hyg. 4: 844-846.

Tseng J C, Levin B, Hirano T, Yee H, Pampeno C, Meruelo D. In vivo antitumor activity of sindbis viral vectors. J Natl Cancer Inst (Bethesda) 2002;94: 1790-802.

Tseng J C, Levin B, Hurtado A, et al. Systemic tumor targeting and killing by Sindbis viral vectors. Nat Biotechnol 2004a ;22:70-7.

Tseng J C, Hurtado A, Yee H, Levin B, Boivin C, Benet M, Blank S V, Pellicer A, Meruelo D. "Using sindbis viral vectors for specific detection and suppression of advanced ovarian cancer in animal models." Cancer Res. 2004 Sep. 15; 64(18):6684-92.

Wang H L, O'Rear J, Stollar V. "Mutagenesis of the Sindbis virus nsP1 protein: effects on methyltransferase activity and viral infectivity." Virology. 1996 Mar. 15; 217(2):527-31.

Weiss B, Geigenmuller-Gnirke U, Schlesinger S. "nteractions between Sindbis virus RNAs and a 68 amino acid derivative of the viral capsid protein further defines the capsid binding site." Nucleic Acids Res. 1994 Mar. 11; 22(5):780-6.

Zhang W, Mukhopadhyay S, Pletnev S V, Baker T S, Kuhn R J, Rossmann M G "Placement of the structural proteins in Sindbis virus." J Virol. 2002 November; 76(22): 11645-58.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

TABLE I

Primers used for Sindbis cDNA cloning.

| PRIMER | SEQUENCE (5'→3') | | SV NT | cDNA bp |
|---|---|---|---|---|
| cDNA-1F | ATTGACGGCGTAGTACAC | (SEQ ID NO:7) | 1-20 | cDNA-1 |
| cDNA-1R | GTAACA**AGATCT**CGTGCCGTGACA (Bgl II) | (SEQ ID NO:8) | 2299-2276 | 2276 bp |
| cDNA-2F | GGCACG**AGATCT**TGTTACCAGC (Bgl II) | (SEQ ID NO:9) | 2281-2303 | cDNA-2 |
| cDNA-2R | CTTTCTTT**CCTAGG**CACACAGTCATTCTT (Avr II) | (SEQ ID NO:10) | 4265-4293 | 2012 bp |
| cDNA-3F | GACTGTGTG**CCTAGG**AAAGAAAGTG (Avr II) | (SEQ ID NO:11) | 4271-4295 | cDNA-3A |
| SV-6932R | CACACCCAGGTCCTCCAAGATC | (SEQ ID NO:12) | 6932-6953 | 2682 bp |
| SV-6882F | GCATCATTCGACAAAAGCCAAG | (SEQ ID NO:13) | 6882-6903 | cDNA-3B |
| SV-C3R | CTCT**TCTAGA**GGTGGTGGTGTTGTAGTATT (XbaI) | (SEQ ID NO:14) | 7626-7656 | 774 bp |
| cDNA-4F | **GGATCC**CCTGAAAAGGCTGTTTAAG (BamHI) | (SEQ ID NO:15) | 7334-7359 | cDNA-4 |
| cDNA-4R | TCATGTC**TGATCA**AGTCCGGTGA (BcII) | (SEQ ID NO:16) | 9370-9348 | 2014 bp |
| cDNA-5F | GGACT**TGATCA**GACATGACGACCA (BcII) | (SEQ ID NO:17) | 9353-9376 | CDNA-5 |
| cDNA-5R | TTTTTGAAATGTTAAAAACAAAATTTTGTTG | (SEQ ID NO:18) | 11678-11703 | 2350 bp |

The restriction endonuclease recognition sites are underlined. Sindbis virus nucleotide numbers follow Strauss et al (1984) sequence (Accession# NC_001547.1)

TABLE II

Primers used to generate vector polylinkers.

| PRIMER (RE) | SEQUENCE 5'→3' | |
|---|---|---|
| Poly1-T7(+) (AflIII) | CCC**ACATGT**GGGAGGCTAGAGTAC TTAATACGACTCACTATAGGATTG ACGGCGTAGTACACACT**ATTGAAT CAAACAGCCGACC** | (SEQ ID NO:19) |
| Poly1-SP6(+) (AflIII) | CCC**ACATGT**GGGAGGCTAGAGTAC ATTTAGGTGACACTATAGAAATTG ACGGCGTAGTACACACT**ATTGAAT CAAACAGCCGACC** | (SEQ ID NO:20) |
| Poly-2(-) (XbaI) | GGCGCGCC**TCTAGA**CTAGCCTAGG TATGGAAGATCTTCCGCGGATCCG CCTAGTGCAAT**TGGTCGGCTGTTT GATTCAAT** | (SEQ ID NO:21) |
| Poly-3(+) (XbaI) | AGGCTAG**TCTAGA**GGCGCGCCGAT CTCACGTGAGCATGCGTTTAAACT GGGCCCAATGTTA**ACATTTCAAAA AAAAAAAAAAAAA** | (SEQ ID NO:22) |
| Poly-4(-) (AatII) | GGTGATG**ACGTC**CTCGAGGCGGCC GCTTAATTAATTTAAATTTTTTTT **TTTTTTTTTTTTTTTTTTTTTTTT TTTTTTGAAATGT** | (SEQ ID NO:23) |
| PCRPoly-1F (AflIII) | ATATATATCCC**ACATGT** | (SEQ ID NO:24) |
| PCRPoly-2R | GCGCGCCTCTAGA | (SEQ ID NO:25) |
| PCRPoly-3F | AGGCTAGTCTAGAGGC | (SEQ ID NO:26) |
| PCRPoly-4R (AatII) | GGTGATG**ACGTC**CT | (SEQ ID NO:27) |

Restriction endonuclease recognition sites (RE) are underlined. Overlapping sequences are shown in bold.

TABLE III

PRIMERS USED IN SITE-DIRECTED MUTAGENESIS OF E2 GENE.

| PRIMER | SEQUENCE 5'→3' | RE |
|---|---|---|
| E2-I3-F | GCAAAAGAAGCGTCA**TC**GA**T**GACTTTACCCTGAC CAGC (SEQ ID NO:28) | ClaI |
| E2-I3-R | GCTGGTCAGGGTAAAGTC**A**TC**GA**TGACGCTTCTT TTGC (SEE ID NO:29) | ClaI |
| E2-K70-F | CTACATGTCGCTT**A**AGCAGGATCACACCGTTAA AG (SEQ ID NO:30) | Afl II |
| E2-K70-R | CTTTAACGGTGTGATCCTGCT**T**AAGCGACATGT AG (SEQ ID NO:31) | Afl II |
| E2-E181-F | CGGG**C**CCGCACGCTTATACATCCTACCTG**G**AAGA ATCATC (SEQ ID NO:32) | Sma I |
| E2-E181-R | GATGATTCTT**C**CAGGTAGGATGTATAAGCGTGCG G**G**CCCG (SEQ ID NO:33) | Sma I |
| E2-V251-F | GACTTGATC**C**GACATGACGACCACACGG**T**CCAAG GG (SEQ ID NO:34) | Mme I |
| E2-V251-R | CCCTTGG**A**CCGTGTGGTCGTCATGTC**G**GATCAAG TC (SEQ ID NO:35) | Mme I |

Nucleotides changed are underlined and the new restriction sites generated are indicated (RE)

TABLE IV

Nucleotide differences between Ar-339, JT vectors and Sindbis virus Strauss sequence (Strauss et al. 1984)

| nt | Protein (a.a.) | JT | Strauss | Ar-339 | Codon Strauss □ Ar339 | Codon Strauss □ JT | Codon JT □ Ar339 |
|---|---|---|---|---|---|---|---|
| 353 | nsP1 (98) | C | C | T | UAC(Tyr)_UAU(Tyr) | UAC(Tyr)_UAC(Tyr) | UAC(Tyr)_UAU(Tyr) |
| 1380-1 | nsP1 (441) | TG | TG | AT | **UGC(Cys)_AUC(Ile)** | UGC(Cys)_UGC(Cys) | **UGC(Cys)_AUC(Ile)** |
| 2992 | nsP2 (438) | T | C | T | **CCC(Pro)_CUC(Leu)** | **CCC(Pro)_CUC(Leu)** | CUC(Leu)_CUC(Leu) |
| 3579 | nsP2 (634) | G | A | G | **AAA(Lys)_GAA(Glu)** | **AAA(Lys)_GAA(Glu)** | GAA(Glu)_GAA(Glu) |
| 3698 | nsP2 (673) | A | G | G | AAG(Lys) AAG(Lys) | AAG(Lys) AAA(Lys) | AAA(Lys)_AAG(Lys) |
| 5702 | nsP3 (534) | T | A | A | CCA(Pro)_CCA(Pro) | CCA(Pro)_CCU(Pro) | CCU(Pro)_CCA(Pro) |
| 7337 | nsP4 (529) | T | T | C | GAU(Asp)_GAC(Asp) | GAU(Asp)_GAC(Asp) | GAU(Asp)_GAC(Asp) |
| 7846 | C (67) | C | C | A | **CCG(Pro)_CAG(Gln)** | CCG(Pro)_CCG(Pro) | **CCG(Pro)_CAG(Gln)** |
| 8009 | C (121) | A | G | G | GAG(Glu)_GAG(Glu) | GAG(Glu)_GAA(Glu) | GAA(Glu)_GAG(Glu) |
| 8345 | C (233) | C | C | A | GGC(Gly)_GGA(Gly) | GGC(Gly)_GGC(Gly) | GGC(Gly)_GGA(Gly) |
| 8638 | E2 (3) | T | T | C | **AUU(Ile)_ACU(Thr)** | AUU(Ile)_AUU(Ile) | **AUU(Ile)_ACU(Thr)** |
| 8698 | E2 (23) | A | T | A | **GUA(Val)_GCA(Ala)** | **GUA(Val)_GCA(Ala)** | GCA(Ala)_GCA(Ala) |
| 8838 | E2 (70) | A | A | G | **AAG(Lys)_GAG(Glu)** | AAG(Lys)_AAG(Lys) | **AAG(Lys)_GAG(Glu)** |
| 9144 | E2 (172) | G | A | G | **AGA(Arg)_GGA(Gly)** | **AGA(Arg)□GGA(Gly)** | GGA(Gly)_GGA(Gly) |
| 9171 | E2 (181) | G | G | A | **GAA(Glu)_AAA(Lys)** | GAA(Glu)_GAA(Glu) | **GAA(Glu)_AAA(Lys)** |
| 9382 | E2 (251) | T | C | C | GCC(Ala)_GCC(Ala) | **GCC(Ala)_GUC(Val)** | **GUC(Val)_GCC(Ala)** |
| 10279 | E1 (72) | C | C | T | **GCU(Ala)_GUU(Val)** | GCU(Ala)_GCU(Ala) | **GCU(Ala)_GUU(Val)** |
| 10288 | E1 (75) | G | A | A | GAC(Asp)_GAC(Asp) | **GAC(Asp)_GGC(Gly)** | **GGC(Gly)_GAC(Asp)** |
| 10392 | E1 (109) | T | T | C | UUG(Leu)_CUG(Leu) | UUG(Leu)_UUG(Leu) | UUG(Leu)_CUG(Leu) |
| 10469 | E1 (133) | T | T | A | AUU(Ile)_AUA(Ile) | AUU(Ile)_AUU(Ile) | AUU(Ile)_AUA(Ile) |
| 10773 | E1 (237) | T | T | G | **UCA(Ser)_GCA(Ala)** | UCA(Ser)_UCA(Ser) | **UCA(Ser)_GCA(Ala)** |

Nucleotide numbers follow the Strauss et al sequence. (Accession # NC_001547.1)

TABLE V

Nucleotide differences between JT vectors and Strauss sequence

| nt | Protein (a.a.) | Codon Strauss □ JT | Plasmid |
|---|---|---|---|
| 2992 | nsP2 (438) | **CCC(Pro)_CUC(Leu)** | Replicon |
| 3579 | nsP2 (634) | **AAA(Lys)_GAA(Glu)** | Replicon |
| 3698 | nsP2 (673) | AAG(Lys) AAA(Lys) | Replicon |
| 5702 | nsP3 (534) | CCA(Pro)_CCU(Pro) | Replicon |
| 7337 | nsP4 (529) | GAU(Asp)_GAC(Asp) | Replicon |
| 8009 | Capsid (121) | GAG(Glu)_GAA(Glu) | Helper |
| 8698 | E2 (23) | **GUA(Val)_GCA(Ala)** | Helper |
| 9144 | E2 (172) | **AGA(Arg)_GGA(Gly)** | Helper |
| 9382 | E2 (251) | **GCC(Ala)_GUC(Val)** | Helper |
| 10288 | E1 (75) | **GAC(Asp)_GGC(Gly)** | Helper |

Strauss et al 1984 sequence. (Accession # NC_001547.1)

TABLE VI

Summary of amino acid differences between JT and Ar-339 vectors

| nt | Protein (a.a.) | Codon JT □ Ar339 | Plasmid |
|---|---|---|---|
| 1380/1381 | nsP1 (441) | **UGC(Cys)_AUC(Ile)** | Replicon |
| 7846 | Capsid (67) | **CCG(Pro)_CAG(Gln)** | Helper |
| 8638 | E2 (3) | **AUU(Ile)_ACU(Thr)** | Helper |
| 8838 | E2 (70) | **AAG(Lys)_GAG(Glu)** | Helper |
| 9171 | E2 (181) | **GAA(Glu)_AAA(Lys)** | Helper |
| 9382 | E2 (251) | **GUC(Val)_GCC(Ala)** | Helper |
| 10279 | E1 (72) | **GCU(Ala)_GUU(Val)** | Helper |
| 10288 | E1 (75) | **GGC(Gly)_GAC(Asp)** | Helper |
| 10773 | E1 (153) | **UCA(Ser)_GCA(Ala)** | Helper |

TABLE VII

TITER OF CHIMERIC VIRAL VECTORS.

| VIRAL VECTOR | BHK-21 cells (TU/mL) | ES-2/Fluc cells (TU/mL) | Mosec cells (TU/mL) |
|---|---|---|---|
| JT-BB/SP6-ARepLacZ | $3 \times 10^6$ | $3 \times 10^4$ | $3 \times 10^4$ |
| SP6-AH/JT-RepLacZ | $3 \times 10^4$ | $3 \times 10^3$ | $3 \times 10^3$ |
| SP6-AH/SP6-ARepLacZ | $3 \times 10^4$ | $3 \times 10^3$ | $3 \times 10^3$ |
| JT-BB/JT-RepLacZ | $3 \times 10^6$ | $3 \times 10^4$ | $3 \times 10^4$ |

Vectors were titered in BHK-21, ES-2/Fluc and Mosec cell lines.

TU transducing units

TABLE VIII

TITERS OF E2 MUTANT VECTORS.

| VIRAL VECTOR | BHK-21 (TU/mL) | ES-2/Fluc (TU/mL) | Mosec (TU/mL) |
|---|---|---|---|
| A (JT-BB/SP6-RFluc) | $10^7$ | $10^5$ | $10^6$ |
| C (SP6-H/SP6-RFluc) | $10^5$ | $10^3$ | $10^4$ |
| Mut-1 (SP6H-K70/SP6-RFluc) | $10^4$ | $10^3$ | $10^5$ |
| Mut-2 (SP6H-K70-V251/SP6-RFluc) | $10^5$ | $10^4$ | $10^2$ |
| Mut-4 (SP6H-I3-K70-E181-V251/SP6-RFluc) | $10^6$ | $10^4$ | $10^5$ |

Vectors were titered in BHK-21, ES-2/Fluc and Mosec cell lines.

TU transducing units

What is claimed is:

1. A purified, isolated nucleic acid comprising a nucleotide sequence consisting of the sequence as set forth in SEQ ID NO. 39 (SP6-H-I3-K70-E181-Val 251).

2. A purified, isolated nucleic acid comprising a nucleotide sequence consisting of the sequence as set forth in SEQ ID NO. 36 (SP6-R).

3. A method for producing defective Sindbis viral vectors comprising the steps of (a) providing a linearized replicon plasmid comprising a nucleotide sequence consisting of the sequence as set forth in SEQ ID NO: 36 and a linearized Helper plasmid comprising a nucleotide sequence consisting of the sequence as set forth in SEQ ID NO: 39;

(b) transcribing said replicon plasmid and said Helper plasmid to produce RNA;

(c) collecting the RNA transcribed in step (b) from said replicon plasmid and said Helper plasmid and transfecting cells with said RNA;

(d) incubating said transfected cells for a time and at a temperature effective for producing defective Sindbis viral vectors; and (e) collecting said defective Sindbis viral vectors from the medium of said transfected.

* * * * *

UNITED STATES PATENT AND TRADEMARK OFFICE

CERTIFICATE OF CORRECTION

PATENT NO. : 7,303,898 B2
APPLICATION NO. : 11/392926
DATED : December 4, 2007
INVENTOR(S) : Alicia Hurtado and Daniel Meruelo It is certified that error appears in the above-identified patent and that said Letters Patent is hereby corrected as shown below:

In the Specification

Column 1, Lines 15-20 should read:
--This invention was made with government support under grant numbers R01 CA022247 and R01 CA068498 awarded by The National Institutes of Health and under grant number DAMD17-01-1-0728 awarded by the Department of Defense. The government has certain rights in the invention.--

Signed and Sealed this
Twenty-ninth Day of November, 2022

Katherine Kelly Vidal
*Director of the United States Patent and Trademark Office*